US006555329B2

(12) United States Patent
Jenuwein et al.

(10) Patent No.: US 6,555,329 B2
(45) Date of Patent: Apr. 29, 2003

(54) METHOD FOR IDENTIFYING COMPOUNDS ALTERING HIGHER-ORDER CHROMATIN-DEPENDENT CHROMOSOME STABILITY

(75) Inventors: Thomas Jenuwein, Vienna (AT); Stephen Rea, Headford (IE); Frank Eisenhaber, Vienna (AT); Dónal O'Carroll, Greystones (IE)

(73) Assignee: Boehringer Ingelheim International GmbH (DE)

( * ) Notice: Subject to any disclaimer, the term of this patent is extended or adjusted under 35 U.S.C. 154(b) by 0 days.

(21) Appl. No.: 09/876,221

(22) Filed: Jun. 8, 2001

(65) Prior Publication Data

US 2002/0081638 A1 Jun. 27, 2002

Related U.S. Application Data

(60) Provisional application No. 60/224,220, filed on Aug. 9, 2000.

(30) Foreign Application Priority Data

Jun. 9, 2000 (EP) .............................. 00112345
Jun. 9, 2000 (EP) .............................. 00112479

(51) Int. Cl.[7] ........................... C12Q 1/48; G01N 33/53
(52) U.S. Cl. ......................... 435/15; 435/7.1; 435/7.72
(58) Field of Search ....................... 435/6, 4, 7.1, 7.71, 435/7.72, 7.8, 7.92, 15, 40.5, 69.2, 183, 193, 5, 196

(56) References Cited

U.S. PATENT DOCUMENTS 5,972,608 A * 10/1999 Peterson et al. ................ 435/5

OTHER PUBLICATIONS

Park et al (Abstract only), Int J Biochem 1988:20(2):183–7.*
Pending Non–Provisional U.S. patent application No. 09/589,892, Jenuwein et al., filed Jun. 9, 2000.
Aagard, L., et al., "Functional mammalian homologues of the Drosophila PEV–modifier Su(var) 3–9 encode centromere–associated proteins which complex with the heterochromatin component M31," *The EMBO Journal* 18:1923–1938, European Molecular Biology Organization (1999).
Aagard, L., et al., "Mitotic phosphorylation of SUV39H1, a novel component of active centronomes, coincides with transient accumulation at mammalian centromeres," *J. Cell Sci.* 113:817–829, The Company of Biologists Limited (Mar. 2000).
Aasland, R. and Stewart, A.F., "The chromo shadow domain, a second chromo domain in heterochromatin–binding protein 1, HP1," *Nucleic Acids Res.* 23:3168–3173, Oxford University Press (1995).

Adams, R.R., et al., "INCENP binds the Aurora–related kinase AIRK2 and is required to target it to chromosomes, the central spindle and cleavage furrow," *Curr. Biol.* 10:1075–1078, Elsevier Science Ltd. (Sep. 2000).
Ainsztein, A.M., "INCENP Centromere and Spindle Targeting: Identification of Essential Conserved Motifs and Involvement of Heterochromatin Protein HP1," *J. Cell Biol.* 143:1763–1774, The Rockefeller University Press (1998).
Allshire, R.C., et al., "Mutations derepressing silent centromeric domains in fission yeast disrupt chromosome segregation," *Genes Dev.* 9:218–233, Cold Spring Harbor University Press (1995).
Baksa, K., et al., "Mutations in the Protein Phosphatase 1 Gene at 87B Can Differentially Affect Suppression of Position–Effect Variegation and Mitosis in *Drosophila melanogaster*," *Genet.* 135:117–125, The Genetics Society of America (1993).
Ball, L.J., et al., "Structure of the chromatin binding (chromo) domain from mouse modifier protein 1," *The EMBO Journal* 16:2473–2481, Oxford university Press (1997).
Bannister, A.J., et al., "Selective recognition of methylated lysine 9 on histone H3 by the HP1 chromo domain," *Nature* 410:120–124, Nature Publishing Group (Mar. 2001).
Baudat, F., et al., "Chromosome Synapsis Defects and Sexually Dimorphic Meiotic Progression in Mice Lacking Spoll," *Mol. Cell* 6:989–998, Cell Press (Nov. 2000).
Bernard, P., et al., "Fission Yeast Bub1 Is a Mitotic Centromere Protein Essential for the Spindle Checkpoint and the Preservation of Correct Ploidy through Mitosis," *J. Cell Biol.* 143:1775–1787, The Rockefeller University Press (1998).
Burgoyne, P.S., "Genetic Homology and Crossing Over in the X and Y Chromosomes of Mammals," *Hum. Genet.* 61:85–90, Springer–Verlag (1982).
Chen, D., et al., "Regulation of Transcription by a Protein Methyltransferase," *Science* 284:2174–2177, American Association for the Advancement of Science (1999).
Cléard, F., et al., "SU (VAR) 3–7, a Drosphila heterochromatin–associated protein and companion of HP1 in the genomic silencing of position–effect variegation," *The EMBO Journal* 16:5280–5288, Oxford University Press (1997).
Cobb, J., et al., "Meiotic events at the centromeric heterochromatin: histone H3 phosphorylation, topoisomerase IIα localization and chromosome condensation," *Chromosoma* 108:412–425, Springer–Verlag (1999).

(List continued on next page.)

*Primary Examiner*—Mary E. Mosher
*Assistant Examiner*—Misook Yu
(74) *Attorney, Agent, or Firm*—Sterne, Kessler, Goldstein & Fox, P.L.L.C.

(57) ABSTRACT

A method for identifying compounds that alter higher order chromatin dependent chromosome stability is based on determining the compounds' ability to modify a methyltransferase with Suv39h–like methyltransferase activity. The identified compounds are useful in therapy, in particular the therapy of human cancer and for contraception.

12 Claims, 42 Drawing Sheets

OTHER PUBLICATIONS

Cortez, D. and Elledge, S.J., "Conducting the mitotic symphony," *Nature 406*:354–356, Nature Publishing Group (Jul. 2000).

Csink, A.K. and Henikoff, S., "Genetic modification of heterochromatic association and nuclear organization in Drosophila," *Nature 381*:529–531, Nature Publishing Group (1996).

Cutts, S.M., et al., "Defective chromosome segregation, microtubule bundling and nuclear bridging in inner centromere protein gene (Incenp) –disrupted mice," *Hum. Mol. Genet. 8*:1145–1155, Oxford University Press (1999).

Dernburg, A.F., et al., "Perturbation of Nuclear Architecture by Long–Distance Chromosome Interactions," *Cell 85*:754–759, Cell Press (1996).

Dernberg, A.F., et al., "Direct Evidence of a Role for Heterochromatin in Meiotic Chromasome Segregation," *Cell 86*:135–146, Cell Press (1996).

De Rubertis, F., et al., "The histone deacetylase RPD3 counteracts genomic silencing in Drosophila and yeast," *Nature 384*:589–591, Nature Publishing Group (1996).

de Vries, S.S., et al., "Mouse MutS–like protein Msh5 is required for proper chromosome synapsis in male and female meiosis," *Genes & Development 13*:523–531, Cold Spring Harbor University Press (1999).

Eissenberg, J.C., et al., "The Heterochromatin–Associated Protein HP-1 Is an Essential Protein in Drosophila With Dosage–Dependent Effects on Position–Effect Variegation," *Genetics 131*:345–352, The Genetics Society of America (1992).

Ekwall, K., et al., "Mutations in the fission yeast silencing factors clr4+ and rik1+ disrupt the localisation of the chromo domain protein Swi6p and impair centromere function," *J. Cell Sci. 109*:2637–2648, The Company of Biologists Limited (1996).

Ekwall, K., et al., "Transient Inhibition of Histone Deacetylation Alters the Structural and Functional Imprint at Fission Yeast Centromeres," *Cell 91*:1021–1032, Cell Press (1997).

Foon, K.A. and Gale, R.P., "Chronic Lymphoid Leukemias," in *Blood: Principles and Practice of Hematology*, Handin, R.I., et al., eds., J.B. Lippincott Company, Philadelphia, PA, pp. 783–811 (1995).

Grunstein, M., "Yeast Heterochromatin: Regulation of Its Assembly and Inheritance by Histones," *Cell 93*:325–328, Cell Press (1998).

Hawley, R.S., et al., "There Are Two Mechanisms of Achiasmate Segregation in Drosophila Females, One of Which Requires Heterochromatic Homology," *Developmental Genetics 13*:440–467, Wiley–Liss, Inc. (1993).

Hendzel, M.J., et al., "Mitosis–specific phosphorylation of histone H3 initiates primarily within pericentromeric heterochromatin during G2 and spreads in an ordered fashion coincident with mitotic chromosome condensation," *Chromosoma 106*:348–360, Springer–Verlag (1997).

Henikoff, S., "Position–effect Variegation in Drosophila: Recent Progress," in *Epigenetic Mechanisms of Gene Regulation*, Russo, V.E.A., et al., eds., Cold Spring Harbor Laboratory Press, Cold Spring Harbor, NY, pp. 319–334 (1996).

Hsu, J.–Y., et al., "Mitotic Phosphorylation of Histone H3 Is Governed by Ipl1/aurora Kinase and Glc7/PP1 Phosphatase in Budding Yeast and Nematodes," *Cell 102*:279–291, Cell Press (Aug. 2000).

Ivanova, A.V., et al., "The chromo and SET domains of the Clr4 protein are essential for silencing in fission yeast," *Nat. Genet. 19*:192–195, Nature Publishing Group (1998).

Jacobson, S. and Pillus, L., "Modifying chromatin and concepts of cancer," *Curr. Opin. Genet. Dev. 9*:175–184, Current Biology Publications (1999).

Jenuwein, T., et al., "SET domain proteins modulate chromatin domains in eu– and heterochromatin," *Cell. Mol. Life Sci. 54*:80–93, Berkhäuser Verlag (1998).

Jenuwein, T., "Re–SET–ting heterochromatin by histone methyltransferases," *TRENDS Cell Biol. 11*:266–273, Elsevier Science (Jun. 2001).

Jones, D.O., et al., "Mammalian chromodomain proteins: their role in genome organisation and expression," *BioEssays 22*:124–137, John Wiley & Sons, Inc. (Feb. 2000).

Kaitna, S., et al., "Incenp and an Aurora–like kinase form a complex essential for chromosome segregation and efficient completion of cytokinesis," *Curr. Biol. 10*:1172–1181, Current Biology Publications (Oct. 2000).

Karpen, G.H., et al., "Centric Heterochromatin and the Efficiency of Achiasmate Disjunction in Drosophila Female Meiosis," *Science 273*:118–122, American Association for the Advancement of Science (1996).

Karpen, G.H. and Allshire, R.C., "The case for epigenetic effects on centromere identity and function," *TIG 13*:489–498, Elsevier Science Ltd (1997).

Klein, R.R. and Houtz, R.L., "Cloning and developmental expression of pea ribulose–1,5–bisphosphate carboxylase/oxygenase large subunit N–methyltransferase," *Plant Mol. Biol. 27*:249–261, Kluwer Academic Publishers (1995).

Koonin, E.V., et al., "The chromo superfamily: new members, duplication of the chromo domain and possible role in delivering transcription regulators to chromatin," *Nucleic Acids Res. 23*:4229–4233, Oxford University Press (1995).

Lachner, M., et al., "Methylation of histone H3 lysine 9 creates a binding site for HP1 proteins," *Nature 410*:116–120, Nature Publishing Group (Mar. 2001).

Laible, G., et al., "Mammalian homologues of the Polycomb–group gene *Enhancer of zeste* mediate gene silencing in Drosphila heterochromatin and at *S. cerevisiae* telomeres," *The EMBO Journal 16*:3219–3232, Oxford University Press (1997).

Lamb, D.J. and Niederberger, C.S., "Animal Models That Mimic Human Male Reproductive Defects," *Male Infertility 21*:377–387, W.B. Saunders Company (1994).

Lammers, J.H.M., et al., "A change in the phosphorylation pattern of the 30000–33000 $M_r$ synaptonemal complex proteins of the rat between early and mid–pachytene," *Chromosoma 104*:154–163, Springer–Verlag (1995).

Larsson, J., et al., "Mutations in the *Drosophila melanogaster* Gene Encoding S–adenosylmethionine Suppress Position–Effect Variegation,"*Genetics 143*:887–896, The Genetics Society of America (1996).

Lengauer, C., et al., "Genetic instability in colorectal cancers," *Nature 386*:623–627, Nature Publishing Group (1997).

Martzen, M.R., et al., "A Biochemical Genomics Approach for Identifying Genes by the Activity of Their Products," *Science 286*:1153–1155, Nature Publishing Group (1999).

Melcher, M., et al., "Structure–Function Analysis of SUV39H1 Reveals a Dominant Role in Heterochromatin Organization, Chromosome Segregation, and Mitotic Progression," *Mol. Cell Biol. 20*:3728–3841, American Society for Microbiology (May 2000).

Motzkus, D., et al., "M31, a murine homolog of Drosophila HP1, is concentrated in the XY body during spermatogenesis," *Cytogenet. Cell Genet.* 86:83–88, S. Karger AG, Basel (1999).

Nakayama, J., et al., "Role of Histone H3 Lysine 9 Methylation in Epigenetic Control of Heterochromatin Assembly," *Science* 292:110–113, American Association for the Advancement of Science (Apr. 2001).

O'Carroll, D., et al., "Isolation and Characterization of Suv39h2, a Second Histone H3 Methyltransferase Gene That Displays Testis–Specific Expression," *Mol. Cell. Biol.* 20:9423–9433, American Society for Microbiology (Dec. 2000).

Offenberg, H.H., et al., "Tissue distribution of two major components of synaptonemal complexes of the rat," *Chromosoma* 101:83–91, Springer–Verlag (1991).

Pardue, M.L. and Gall, J.G., "Chromosomal Localization of Mouse Satellite DNA," *Science* 168:1356–1358, American Association for the Advancement of Science (1970).

Peters, A.H.F.M., et al., "A drying–down technique for the spreading of mammalian meiocytes from the male and female germline," *Chromosome Res.* 5:66–71, Rapid Science Publishers (1997).

Peters, A.H.F.M., et al., "Meiosis in carriers of heteromorphic bivalents: sex differences and implications for male fertility," *Chromosome Res.* 5:313–324, Rapid Science Publishers (1997).

Pehrson, J.R. and Fried, V.A., "MacroH2A, a Core Histone Containing a Large Nonhistone Region," *Science* 257:1398–1400, American Association for the Advancement of Science (1992).

Platero, J.S., et al., "Functional analysis of the chromo domain of HP1," *The EMBO Journal* 14:3977–3986, Oxford University Press (1995).

Rea, S., et al., "Regulation of chromatin structure by site–specific histone H3 methyltransferases," *Nature* 406:593–599, Nature Publishing Group (Aug. 2000).

Reuter, G. and Spierer, P., "Position Effect Variegation and Chromatin Proteins," *BioEssays* 14:605–612, The Company of Biologists Limited (1992).

Rice, J.C. and Allis, C.D., "Histone methylation versus histone acetylation: new insights into epigenetic regulation," *Curr. Opin. Cell Biol.* 13:263–273, Elsevier Science Limitexd (Jun. 2001).

Sassone–Corsi, P., et al., "Requirement for Rsk–2 for Epidermal Growth Factor–Activated Phosphorylation of Histone H3," *Science* 285:886–891, American Association for the Advancement of Science (1999).

Scherthan, H., et al., "Centromere and Telomere Movements during Early Meiotic Prophase of Mouse and Man Are Associated with the Onset of Chromosome Pairing," *J. Cell. Biol.* 134:1109–1125, The Rockefeller University Press (1996).

Schotta, G. and Reuter, G., "Controlled expression of tagged proteins in Drosophila using a new modular P–element vector system," *Mol. Gen. Genet.* 262:916–920, Springer–Verlag (Jan. 2000).

Solari, A.J., "The Behavior of the XY Pair in Mammals," *International Review of Cytology* 38:273–317, Academic Press (1974).

Stassen, M.J., et al., "The *Drosophila trithorax* proteins contain a novel variant of the nuclear type DNA binding domain and an ancient conserved motif found in other chromosomal proteins," *Mech. Dev.* 52:209–223, Elsevier Science Ireland Ltd. (1995).

Strahl, B.D. and Allis, C.D., "The language of covalent histone modifications," *Nature* 403:41–45, Nature Publishing Group (Jan. 2000).

Strahl, B.D., et al., "Methylation of histone H3 at lysine 4 is highly conserved and correlates with transcriptionally active nuclei in Tetrahymena," *PNAS* 96:14967–14972, National Academy of Sciences of the United States of America (1999).

Sullivan, K.F., et al., "Human CENP–A Contains a Histone H3 Related Histone Fold Domain That Is Required for Targeting to the Centromere," *J. Cell Biol.* 127:581–592, The Rockefeller University Press (1994).

Tachibana, M., et al., "SET Domain–containing Protein, G9a, Is a Novel Lysine–preferring Mammalian Histone Methyltransferase with Hyperactivity and Specific Selectivity to Lysines 9 and 27 of Histone H3," *J. Biol. Chem.* 276:25309–25317, The American Society for Biochemistry and Molecular Biology, Inc. (Jul. 2001).

Tkachuk, D.C., et al., "Involvement of a Homolog of Drosophila Trithorax by 11q23 Chromosomal Translocations in Acute Leukemias," *Cell* 71:691–700, Cell Press (1992).

Tschiersch, B., et al., "The protein encoded by the Drosophila position–effect variegation suppressor gene Su (var) 3–9 combines domains of antagonistic regulators of homeotic gene complexes," *The EMBO Journal* 13:3822–3831, Oxford University Press (1994).

Turner, B.M., "Histone acetylation as an epigenetic determinant of long–term transcriptional competence," *Cell. Mol. Life Sci.* 54:21–31, Birkhäuser Verlag (1998).

Turner, J.M.A., et al., "Analysis of male meiotic 'sex body' proteins during XY female meiosis provides new insights into their functions," *Chromosoma* 109:426–432, Springer–Verlag (Aug. 2000).

Vigil, P. and Bustos–Obregon, E., "Alkylating Agents and Mouse Spermatogenesis: Effects of a Single Dose of Cyclophosphamide," *andrologia* 17:276–282, Grosse–Verlag (1985).

Wallrath, L.L., "Unfolding the mysteries of heterochromatin," *Curr. Opin. Genet. Dev.* 8:147–153, Current Biology Ltd. (1998).

Wei, Y., et al., "Phosphorylation of Histone H3 Is Required for Proper Chromosome Condensation and Segregation," *Cell* 97:99–109, Cell Press (1999).

Weinbauer, G.F., et al., "Quantitative Analysis of Spermatogenesis and Apoptosis in the Common Marmoset (*Callithrix jacchus*) Reveals High Rates of Spermatogonial Turnover and High Spermatogenic Efficiency," *Biol. Reprod.* 64:120–126, The Society for the Study of Reproduction, Inc. (Jan. 2001).

Working, P.K., "Male Reproductive Toxicology: Comparison of the Human to Animal Models," *Environ. Health Perspect.* 77:37–44, U.S. Department of Health and Human Services (1988).

Wreggett, K.A., et al., "A mammalian homologue of Drosophila heterochromatin protein 1 (HP1) is a component of constitutive heterochromatin," *Cytogenet. Cell Genet. 66*:99–103, S. Karger AG (1994).

Xu, X., et al., "Centrosome Amplification and a Defective $G_2$–M Cell Cycle Checkpoint Induce Genetic Instability in BRCA1 Exon 11 Isoform–Deficient Cells," *Mol. Cell 3*:389–395, Cell Press (1999).

Xu, Y., et al., "Targeted disruption of ATM leads to growth retardation, chromosomal fragmentation during meiosis, immune defects, and thymic lymphoma," *Genes Dev. 10*:2411–2422, Cold Spring Harbor Laboratory Press (1996).

Yoshida, K., et al., "The Mouse RecA–like Gene Dmc1 Is Required for Homologous Chromosome Synapsis during Meiosis," *Mol. Cell 1*:707–718, Cell Press (1998).

Yuan, L., et al., "The Murine SPC3 Gene Is Required for Synaptonemal Complex Assembly, Chromosome Synapsis, and Male Fertility," *Mol. Cell 5*:75–83, Cell Press (Jan. 2000).

Zheng, Q., et al., "Expression, Purification, and Characterization of Recombinant Ribulose–1,5–Bisphosphate Carboxylase/Oxygenase Large Subunit $N^\epsilon$—Methyltransferase," *Protein Express. Purif. 14*:104–112, Academic Press (1998).

Co–pending U.S. application No. 09/876,224, Jenuwein, T. et al., filed Jun. 8, 2001.

\* cited by examiner

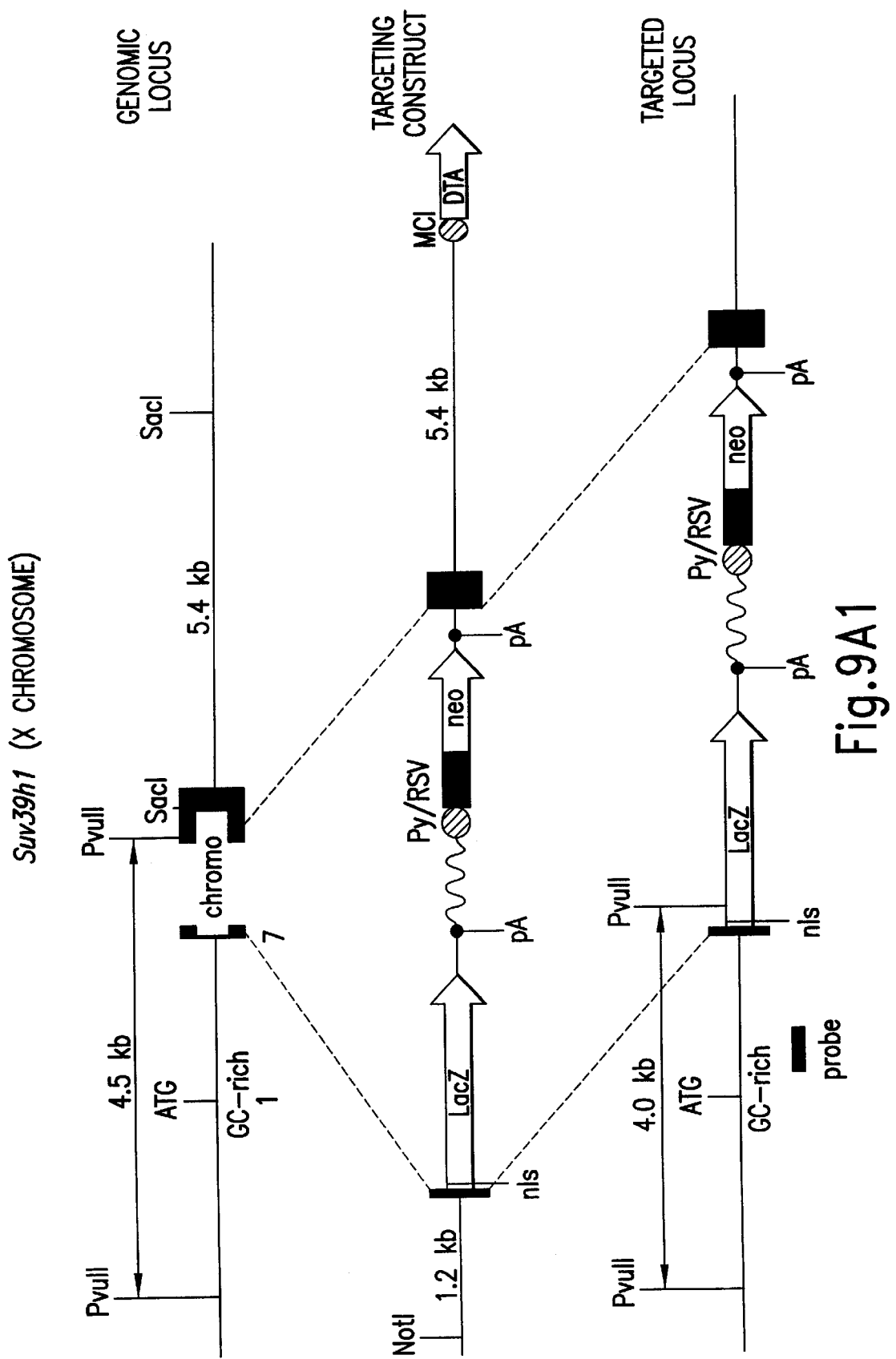
Fig.9A1

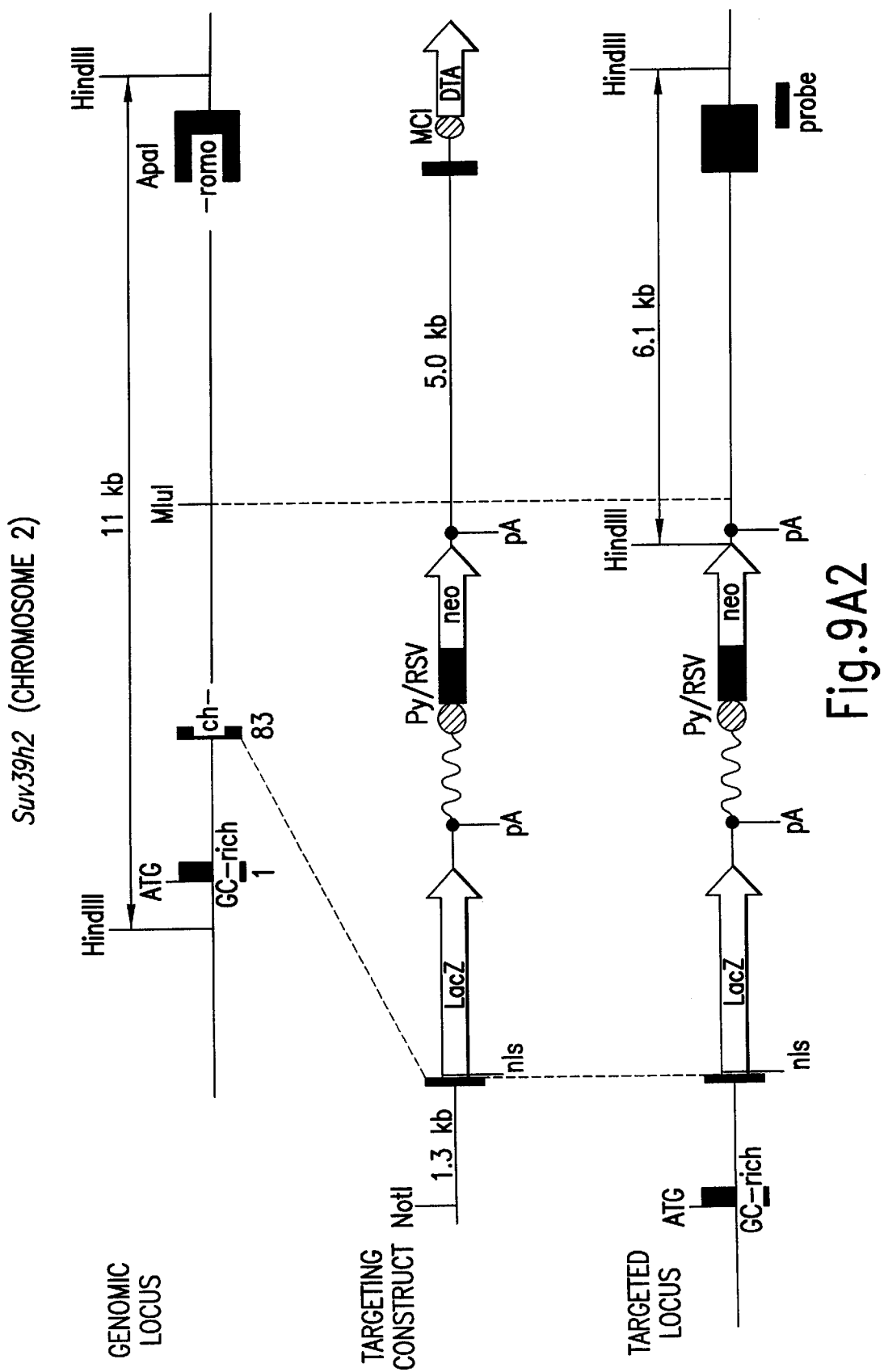
Fig.9A2

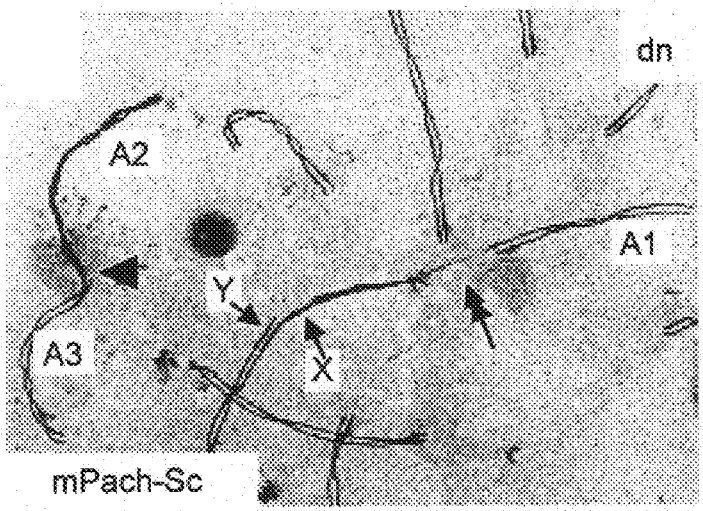
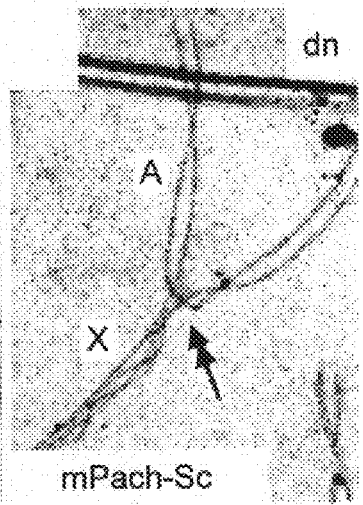
Fig.14D  Fig.14E
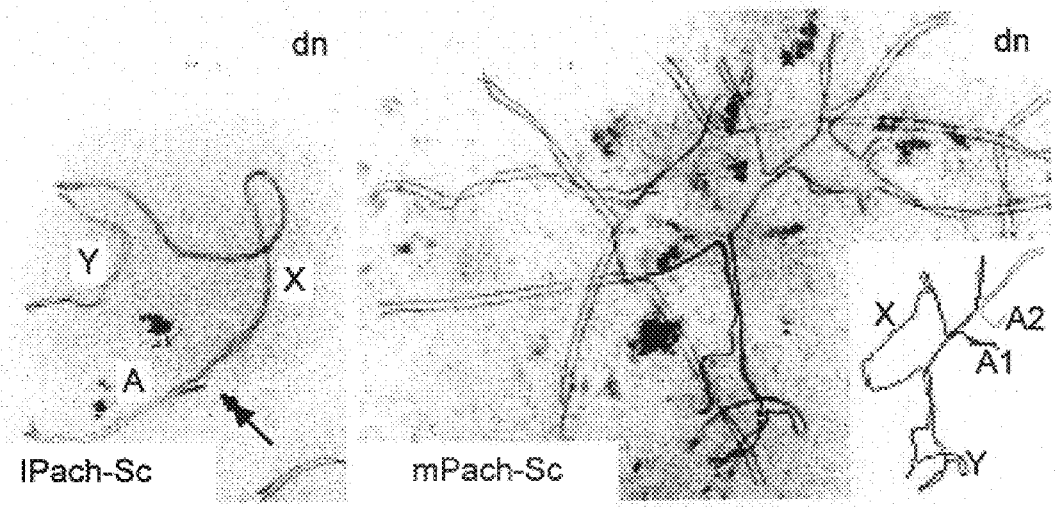
Fig.14F  Fig.14G

METHOD FOR IDENTIFYING COMPOUNDS ALTERING HIGHER-ORDER CHROMATIN-DEPENDENT CHROMOSOME STABILITY

CROSS REFERENCE TO RELATED APPLICATIONS

This application claims priority benefit of U.S. Provisional Application No. 60/224,220, filed Aug. 9, 2000, which is hereby incorporated by reference in its entirety.

BACKGROUND OF THE INVENTION

1. Field of the Invention

The invention relates to a method for identifying compounds influencing chromosome dynamics in eukaryotic cells. In particular, the invention relates to the treatment and prevention of human conditions by modulating higher order chromatin dependent chromosome stability during mitosis and meiosis.

2. Related Art

Higher-order chromatin is essential for epigenetic gene control and for the functional organisation of chromosomes. Differences in higher-order chromatin structure have been linked with distinct covalent modifications of histone tails which regulate transcriptional 'on' or 'off' states (Grunstein, 1998; Turner, 1998; Strahl and Allis, 2000) and influence chromosome condensation and segregation (Karpen and Allshire, 1997; Wei et al., 1999).

Histones constitute a highly conserved family of proteins (H3, H4, H2A, H2B, H1) which are the major components of eukaryotic chromatin structure. Histones compact genomic DNA into basic repeating structural units, the nucleosomes. In addition to their DNA packaging function, histones have been proven to be integral components of the molecular machinery that regulates gene expression.

Post-translational modifications of histone N-termini, particularly of H4 and H3, are well documented and have functionally been characterised as changes in acetylation (Grunstein, 1998; Turner, 1998; Strahl and Allis, 2000), phosphorylation (Wei et al., 1999) and, most recently, methylation (Chen et al., 1999; Strahl et al., 1999). In contrast to the large number of described histone acetyltransferases (HATs) and histone deacetylases (HDACs), genes encoding enzymatic activities that regulate phosphorylation (Sassone-Corsi et al., 1999; Hsu et al., 2000) or methylation (Chen et al., 1999) of histone N-termini are only beginning to be identified. Moreover, the interdependence of the different histone tail modifications for the integration of transcriptional output or higher-order chromatin organisation is currently not understood.

Overall, there is increasing evidence that the regulation of normal and aberrant cellular proliferation is not only affected on the transcriptional level, but that also a higher level of regulation is involved, i.e. the organisation of chromatin structure through the modification of histone molecules. The determination of the proteins and the molecular mechanisms involved in histone modification will contribute to the understanding of the cellular proliferation program and will thus shed led light on the mechanisms involved in aberrant proliferation occurring in tumour formation and progression (Jacobson and Pillus, 1999).

Genetic screens for suppressors of position effect variegation (PEV) in Drosophila (Reuter and Spierer, 1992) and S. pombe (Allshire et al., 1995) have identified a subfamily of approximately 30–40 loci which are referred to as Su(var)-group (Wallrath, 1998) genes. Interestingly, several histone deacetylases (De Rubertis et al., 1996), protein phosphatase type 1 (Baksa et al., 1993) and S-adenosyl methionine synthetase (Larsson et al., 1996) have been classified as Su(var)s. In contrast, Su(var)2-5 (which is allelic to HP1) (Eissenberg et al., 1992), Su(var)3-7 (Cléard et al., 1997) and Su(var)3-9 (Tschiersch et al., 1994; Schotta and Reuter, 2000) encode heterochromatin-associated proteins. Su(var) gene function thus suggests a model, in which modifications at the nucleosomal level may initiate the formation of defined chromosomal subdomains that are then stabilised and propagated by heterochromatic SU(VAR) proteins (Henikoff, 1997).

Su(var)3-9 is dominant over most PEV modifier mutations (Tschiersch et al., 1994), and mutants in the corresponding S. pombe clr4 gene (Ivanova et al., 1998) disrupt heterochromatin association of other modifying factors and result in chromosome segregation defects (Ekwall et al., 1996). Recently, human (SUV39H1) and murine (Suv39h1 and Suv39h2) Su(var)3-9 homologues have been isolated (Aagaard et al., 1999). It has been shown that they encode heterochromatic proteins which associate with mammalian HP1 (Aagaard et al., 1999). The SU(VAR)3-9 protein family combines two of the most evolutionarily conserved domains of 'chromatin regulators': the chromo (Aasland and Stewart, 1995; Koonin et al., 1995) and the SET (Tschiersch et al., 1994; Jenuwein et al., 1998) domain. Whereas the 60 amino acids chromo domain represents an ancient histone-like fold (Ball et al., 1997) that directs eu- or heterochromatic localisations (Platero et al., 1995), the molecular role of the 130 amino acids SET domain has remained enigmatic. Overexpression studies with human SUV39H1 mutants indicated a dominant interference with higher-order chromatin organisation that, surprisingly, suggested a functional relationship between the SET domain and the distribution of phosphorylated (at serine 10) histone H3 (Melcher et al., 2000).

SUMMARY OF THE INVENTION

It was an object of the invention to gain further insight into the molecular pathways leading to histone modifications and higher-order chromatin organisation in order to harness these findings for interfering with aberrant gene expression and genomic instability through chromosome mis-segregation and thus provide new cancer therapies.

In particular, it was an object of the invention to investigate the function of members of the SU(VAR)3-9 protein family with the view to develop novel strategies to affect higher-order chromatin dependent chromosome stability. Such strategies can be employed in therapies for the treatment of conditions in which aberrant gene expression and genomic instability through chromosome mis-segregation are causally involved. (The term "chromosome stability" implies successful segregation of chromosomes resulting in the maintenance of a stable karyotype).

Examples 1 to 7 of the present invention show that mammalian SU(VAR)3-9 related proteins (human SUV39H1, murine Suv39h1 and murine Suv39h2) are SET domain-dependent H3-specific histone methyltransferases which selectively methylate lysine 9 ("K9") of the H3 N-terminus. Methylation of K9 negatively regulates phosphorylation of adjacent serine 10 and reveals a 'histone code' that appears intrinsically linked to the organisation of higher-order chromatin. (In the following, histone methyltransferases are termed "HMTases" or, more generally, "MTases").

After having identified Suv39h1 and Suv39h2 as mammalian histone H3 lysine 9 specific histone methyltransferases (Suv39h HMTases), it was shown that these HMTases are heterochromatin-enriched enzymes which transiently accumulate at centromeres during mitosis (Aagaard et al., 1999; Aagaard et al., 2000). Moreover, it was shown that methylation of histone H3 at lysine 9 (H3-K9) creates a high-affinity binding site for HP1 proteins (Lachner et al., 2001; Bannister et al., 2001), thereby defining the SUV39H1-HP1 methylation system as a crucial regulatory mechanism for the assembly and propagation of heterochromatin (Jenuwein, 2001). Overexpression of human SUV39H1 induces ectopic heterochromatin and results in chromosome mis-segregation in mammalian cell lines (Melcher et al., 2000). In addition to the essential mitotic functions described above, heterochromatin is also crucial for the dynamic reorganization of meiotic chromosomes. Meiosis is initiated by chromosomal movements from the nuclear lumen to the nuclear envelope, where chromosomes cluster via their pericentric satellite sequences (Hawley et al., 1992; Scherthan et al., 1996). At meiotic prophase, chromosomes condense, followed by homolog pairing and recombination (at pachytene) between maternal and paternal chromosomes. The onset of the meiotic divisions is preceded by desynapsis, further chromosome condensation and histone H3 phosphorylation at pericentric heterochromatin (Cobb et al., 1999). In particular for male germ cells, the haploid genome content is finally organized into one heterochromatic block in elongating spermatids. In Drosophila, heterochromatin and its associated satellite sequences have been proposed to assist in the initial meiotic chromosome movements and in homolog pairing by orienting chromosomes along a similar higher-order structure (Hawley et al., 1992; Karpen et al., 1996; Dernburg et al., 1996b). In germ cells of mammals, a pachytene checkpoint (de Vries et al., 1999) monitors mis-aligned and unpaired chromosomes and arrests cells in meiotic prophase, thereby preventing the production of aneuploid gametes.

It was a further object of the invention to analyse the role of Suv39h1 and Suv39h2 in embryonic development and in spermatogenesis in view of utilizing these proteins as drug targets for conditions involving fertility, in particular male fertility.

To solve the problems underlying the present invention, in a first step bioinformatics techniques were applied. Using the SET domains of the SU(VAR)3-9 protein family as a starting alignment, significant sequence and secondary structure similarities (see Methods) to six plant protein methyltransferases were detected.

To investigate whether the SET domain of human SUV39H1 has enzymatic activity, histones were tested as possible substrates for in vitro methylation. The obtained results demonstrate that SUV39H1 harbors an intrinsic histone methyltransferase activity and suggest that this HMTase activity resides in the C-terminal SET domain.

Using recombinant proteins, both murine GST-Suv39h1 (82–412) and the corresponding human SUV39H1 fusion protein [GST-SUV39H1(82–412)] were shown to be catalytically active. Short internal deletions were introduced into the two conserved regions of the SET domain core in GST-SUV39H11(82–412), and additional mutants lacking the C-terminal tail (ΔC-tail) or the SET-associated cysteine-rich region (Δcys) were generated. All mutant proteins failed to demonstrate HMTase activity.

Although these results suggest a significant contribution by the cysteine-rich regions, their apparent absence in the plant methyltransferases does not prevent catalytic activity. To investigate enzyme function of the SET domain in more detail, point mutations were introduced into the most highly conserved motif. In vitro HMTase assays indicated that all point mutations, with the exception of one, abolished enzymatic activity. Surprisingly, the latter mutation resulted in an hyperactive enzyme with approximately 20-fold increased activity. The data obtained define the $_{320}$H$\phi\phi$NHSC$_{326}$ motif in the SET domain as an important catalytic site.

Because the SET domain is one of the most conserved protein motifs in chromatin regulators (Stassen et al., 1995; Jenuwein et al., 1998), it was next analysed whether SU(VAR)3-9 family members or other SET domain proteins contain HMTase activity. GST-fusion products of the extended SET domains of S. pombe CLR4 (Ivanova et al., 1998), human EZH2 (Laible et al., 1997) and human HRX (Tkachuk et al., 1992) were generated that would correspond to GST-SUV39H1(82–412). Interestingly, GST-CLR4 (127–490) displayed pronounced HMTase activity at three- to five-fold increased levels as compared to the recombinant SUV39H1 product, consistent with CLR4 carrying an arginine at the hyperactive position. The results obtained from this analysis show, in agreement with the mutational analysis of SUV39H1, that HMTase activity towards free histones appears to require the combination of the SET domain with adjacent cysteine-rich regions, which is a quality found in only a restricted number of SET domain containing proteins.

These experiments indicated that the HMTase activity of mammalian SU(VAR)3-9 related proteins is selective for histone H3 under the chosen assay conditions. To examine this finding in more detail, in vitro methylation reactions were performed with individual histones. It could be shown that H3 is specifically methylated by GST-Suv39h1 (82–412), whereas no signals are detected with H2A, H2B or H4. Methylation of H3 has been shown to occur predominantly at lysine 4 in a wide range of organisms, as well as at lysine 9 in HeLa cells, although the responsible HMTase(s) have yet to be defined (Strahl et al., 1999). To investigate the site utilisation profile of Suv39h1, unmodified peptides comprising the wild-type H3 N-terminus and a mutant K9L peptide were tested as substrates. Additionally, insulin and peptides comprising the N-termini of CENP-A (Sullivan et al., 1994), macroH2A (Pehrson and Fried, 1992) were included. These in vitro assays revealed selective methylation of the wild-type H3 peptide. The data obtained also suggested that the H3 N-terminus is a preferred residue for Suv39h1 dependent HMTase activity.

To more definitively determine this site preference, the wild-type H3 N-terminal peptide was in vitro methylated by GST-Suv39h1(82–412), using S-adenosyl-[methyl-$^3$H]-L-methionine. The labelled peptide, purified by reverse-phase HPLC, was then directly microsequenced, and $^3$H-incorporation associated with each individual amino acid was analysed. The results confirmed selective transfer of methyl-label to lysine 9, demonstrating that Suv39h1 is a highly site-specific HMTase for the H3 N-terminus in vitro.

Murine Suv39h genes are encoded by 2 loci, Suv39h1 and Suv39h2. To investigate the in vivo significance of Suv39h function and Suv39h dependent K9 H3 methylation, mouse strains deficient for both Suv39h1 and Suv39h2 were generated. Suv39h1 and Suv39h2 deficient strains were intercrossed to produce Suv39h double deficient mice. Double mutant mice were born in sub-Mendelian ratios. Some double null embryos exhibited severe growth retardation and exencephaly. In addition surviving double mutants were growth retarded, suggesting a role for Suv39h in cell proliferation.

In order to determine whether the embryonic phenotypes in Suv39h null mice can be attributed to mitotic defects, PMEFs (primary mouse embryonic fibroblasts) derived from Suv39h double mice were analysed. Suv39h double null PMEFs display a reduced G1-index and an increased proportion of cells with aberrant nuclear morphologies, reminiscent of division defects during mitosis. Furthermore, double null cells also show genomic instabilities and readily become aneuploid. The severity of these aneuploidies increases with higher passage numbers. The inability of Suv39h double null cells to maintain a stable karyotype may underlie the Suv39h embryonic phenotype.

Phosphorylation at serine 10 (phosH3) in the N-terminal tail of H3 has been shown to be required for condensation and subsequent segregation of chromosomes (Wei et al., 1999). During the cell cycle, phosH3 initiates within pericentric heterochromatin in late G2 and then progresses along the entire chromosomes during mitosis (Hendzel et al., 1997). It was found that in wild-type PMEFs, approximately 7% of the cells stain positive for the characteristic, heterochromatin-associated phosH3 foci. In contrast, this number is increased by a factor of about 3-fold in Suv39h double null PMEFs. This result suggested that the overall levels of phosH3 may be enhanced in Suv39h double null PMEFs. This was confirmed biochemically. Together, the obtained data are most consistent with a model in which Suv39h-mediated methylation of lysine 9 in H3 negatively regulates phosphorylation of serine 10.

Together, these data clearly demonstrate crucial roles for Suv39h during cell division. Loss of Suv39h function impairs K9 histone H3 metylation and induces defective cell division resulting in genome instabilities. Segregation defects/genome instability underlies the aetiology of many human cancers (Lengauer et al., 1997) and are often a prerequisite for tumour progression. These observations make Suv39h an excellent candidate for novel therapeutic approaches for tumour therapies.

In additon, a set of experiments of the present invention provides in vivo evidence that the absence of Suv39h HMTase activities impairs development and viability of mutant mice, and directly correlates with a nearly complete lack of H3-K9 methylation at pericentric heterochromatin. Notably, Suv39h-deficient mice display chromosomal instabilities in both somatic and meiotic cells that are further evidenced by an increased risk for development of B-cell lymphomas and perturbed chromosome interactions during male meiosis. These in vivo data assign a fundamental role for H3-K9 methylation at pericentric heterochromatin and suggest that the Suv39h HMTases regulate a 'heterochromatic competence' which protects chromosome stability during mitosis and meiosis.

Single gene disruptions for either Suv39h1 or Suv39h2 allow for normal mouse development and do not appear to affect viability and fertility of mutant mice. This apparent redundancy in gene function would be consistent with the overlapping expression profile of the two Suv39h genes during mouse embryogenesis (O'Carroll et al., 2000). By contrast, combined disruption of both genes in Suv39h double null (dn) mice results in severly impaired perinatal viability ($\approx$33%; Table I), growth retardation and hypogonadism in males. Both Suv39h dn males and are infertile. Although Suv39h dn fetuses appear to develop normally until day E12.5, they then display smaller body sizes and frequently are resorbed during late gestation. These in vivo analyses indicate an important role(s) for the Suv39h genes during mammalian development and for overall viability. Since the absence of Suv39h HMTase activities induces genomic instabilities, the high lethality of Suv39h dn fetuses could mainly be a consequence of perturbed chromosome segregation which would significantly impair the proliferation and differentiation programmes of the developing embryo.

Although Suv39h enzymes are the major HMTases for H3-K9 methylation at pericentric heterochromatin in somatic cells (see FIG. 12) and in early meiotic cells (see FIG. 13B), there are $\leq 15$ unique gene sequences in the mouse genome that contain the evolutionarily highly conserved SET domain and which are likely to encode additional enzymes with putative HMTase activity (Jenuwein, 2001). At least one of these SET domain containing proteins can indeed also methylate H3 at lysine Tachibana et al., 2001 Thus, the $\approx$33% viability of Suv39h dn mice could be dependent on the compensating activity of other HMTases that may be expressed to varying degrees in the mixed genetic background, in which the Suv39h dn mice have been analyzed.

Absence of Suv39h HMTase activities triggers genomic instabilities in a variety of cell types, including mouse embryonic fibroblasts (PMEFs) (see FIG. 10), fetal liver and bone marrow cells and in spermatogonia (see FIG. 14C). In agreement with the aneuploidies observed in these cellular systems, Suv39h-deficient mice display an increased risk for tumorigenesis, resulting in late-onset B-cell lymphomas in 33% of Suv39h dn mice (see FIG. 11). B-cell lymphomas also develop upon reduced Suv39h gene dosage in compound mutant mice that contain gene disruptions of Suv39h1 (see Table II). Intriguingly, the Suv39h-induced aneuploidies are mainly characterized by segregation failure of the nearly complete set of the chromosomes, resulting in hypo-tetraploid or even hypo-octaploid cells (see FIG. 10). These data suggest a general impairment of chromosome segregation, consistent with the lack of H3-K9 methylation around all acrocentric centromeres in Suv39h dn cells (see FIG. 12).

Distinct modifications of histone N-termini, such as acetylation (Ekwall et al., 1997) and phosphorylation (Wei et al., 1999) have been shown to be required for correct chromosome segregation in *S. pombe* and Tetrahymena, presumably by inducing a specialised chromatin structure at pericentric heterochromatin that facilitates the establishment of a functional centromere. Because H3-K9 methylation restricts H3 phosphorylation mediated by the Ipl1/aurora kinase (Hsu et al., 2000) and is also interdependent with histone acetylation (Rea et al., 2000), the absence of Suv39h HMTase activities is likely to perturb this distinct histone modification pattern. Second, in addition to altering nucleosome arrangements, histone modifications can generate specific interaction affinities for chromatin-associated proteins (Rice and Allis, 2001). Although the localisation of CENP epitopes appears unaltered, heterochromatic enrichment of HP1 proteins is largely lost in Suv39h dn somatic cells (Lachner et al., 2001). Notably, HP1 interacts in vitro with INCENP (Ainsztein et al., 1998) which forms a complex with aurora-B (Adams et al., 2000; Kaitna et al., 2000). Mutation of INCENP induces severe mitotic abnormalities including macronuclei and internuclear bridges, and results in nearly complete chromosome mis-segregation and cytokinesis failure (Cutts et al., 1999; Adams et al., 2000; Kaitna et al., 2000). These intriguing parallels suggest a possible in vivo link between Suv39h-mediated H3-K9 methylation and aurora-B dependent phosphorylation, and could categorize Suv39h genes as novel tumour suppressor genes.

The Suv39h-mediated chromosomal instabilities only affect a sub-population of cells and do not appear to trigger pronounced apoptosis (see FIG. 10B), consistent with similar analyses of clr4 mutants in *S.pombe* (Ekwall et al., 1996;

Ivanova et at., 1998). These data suggest that the Suv39h-induced defects in somatic cells are not under strict surveillance of known checkpoint controls (Cortez and Elledge, 2000; but see Bernard et al., 1998) and may be caused by rather late segregation problems duting mitosis. Indeed, a fraction of Suv39h dn cells contain chromosomes that lag at anaphase. Since Suv39h dn PMEFs are characterized by hypo-tetraploid and hypo-octaploid karyotypes (see FIG. 10D) and tumor cells contain 'butterfly' chromosomes (see FIG. 11C), a model is proposed (FIGS. 16A,B), in which the absence of H3-K9 methylation would allow stronger or more persistent pericentric associations between aligned metaphase chromosomes. Although a role for the Suv39h HMTases in centromeric cohesion remains to be determined, it provides an attractive mechanism to explain possible cytokinesis failure and mis-segregation of the entire chromosome complement without activating known checkpoint controls.

In contrast to somatic cells, Suv39-mediated defects in male meiosis induce pronounced apoptosis of stage V-VI spermatocytes during the transition from mid to late pachytene (see FIG. 13A). Activation of programmed cell death at this stage has also been observed in mouse mutants that are impaired in DNA damage control (Xu et al., 1996), meiotic recombination (Yoshida et al., 1998; de Vries et al., 1999; Baudat et al., 2000) and synaptonemal complex formation (Yuan et al., 2000). In Suv39h dn spermatocytes, pericentric H3-K9 methylation is specifically reduced at the pre-leptotene stage but, surprisingly, appears as a wild-type staining during later meiotic stages (see FIG. 13B, bottom panel). Thus, in analogy to the increased centromeric associations discussed above, it is proposed that impairment of H3-K9 methylation at the onset of meiosis induces aberrant centromere clustering that can no longer be 'rescued' by the hypothetical activity of additional H3-K9 HMTases during mid-pachytene. This model (see FIGS. 16A, B) would characterize Suv39h-dependent H3-K9 methylation as one of the earliest requirements to ensure successful meiosis and to prevent illegitimate heterochromatic interactions. Because non-homologous interactions will result in delayed synapsis or even complete pairing failure (see FIG. 14A), they trigger apoptosis by activating the pachytene checkpoint (de Vries et al., 1999), thereby protecting the male germ line from accumulating aneuploidies.

In Suv39h dn mice, spermatogenic failure is promoted by illegitimate chromosomal interactions, synaptic delay, unpaired sex chromosomes and bivalent mis-segregation at meiosis I (see FIGS. 14–15). Notably, a major fraction of these 'forbidden' interactions comprises physical contacts between the sex chromosomes and autosomes that are largely mediated through centromeric regions (see FIGS. 14D and 14J). These data suggest that the impairment of H3-K9 methylation may allow pericentric heterochromatin to form a more relaxed configuration which is prone to become engaged in random associations. Cytological and genetic studies in Drosophila demonstrated the intrinsic potential of heterochromatin to restrict inter- and intrachromosomal interactions (Dembrug et al., 1996a; Csink and Henikoff, 1996). Moreover, pericentric heterochromatin has been shown to initiate and maintain alignment and pairing of achiasmate chromosomes until meiosis I (Karpen et al., 1996; Dernburg et al.,1996b), suggesting a role for heterochromatin in defining a 'self-complementary' higher-order chromosome structure that would ensure partner recognition of homologous chromosomes (Karpen et al., 1996). The in vivo data on the function of the Suv39h HMTases would be consistent with these proposed roles of heterochromatin and reveal the first evidence that impaired definition of meiotic heterochromatin can affect chromosome identity in a mammalian organism.

Finally, Suv39h deficiency induces uni-valency of the sex chromosomes at pachytene and at diakinesis (see FIG. 15). Intriguingly, HP1β (Motzkus et al., 1999; Turner et al., 2000) and the Suv39h2 HMTase (O'Carroll et al., 2000) localise to the specialised chromatin structure of the sex chromosomes in the XY body. Although XY body formation appears normal in early/mid pachytene of Suv39h dn spermatocytes, Suv39h deficiency prolonges H3-K9 methylation (see arrows in FIG. 13B) and induces hypo-condensation of the Y chromosome (see FIG. 15E). These results involve the Suv39h HMTase activities in the definition of the heterochromatic identity of the Y chromosome and suggest that Suv39h-mediated H3-K9 methylation may indirectly promote or stabilise homolog pairing of the heteromorphic sex chromosomes.

Heterochromatin has been first described more than 70 years agao (Heitz, 1928). Because of its stable appearance in the cell nucleus, it has been proposed to serve crucial functions for the inheritance of cell type identities and the fidelity of chromosome segregation. The discoveries of the first HMTases (Rea et al., 2000; O'Carroll et al., 2000) and their mechanistic link to generate a heterochromatic affinity through H3-K9 methylation and recruitment of HP1 proteins (Lachner et al., 2001; Bannister et al., 2001; Nakayama et al., 2001) has now defined an entry point to start dissecting some of the basic roles of heterochromatin.

The experiments of the present invention have provided in vivo evidence that H3-K9 methylation at pericentric heterochromatin is indeed a crucial requirement to ensure mammalian development and to protect chromosome stability in both somatic cells and male germ cells. Because Suv39h deficiency impairs chromosome function in mitosis and meiosis, the data assign a fundamental role for H3-K9 methylation in directing a 'heterochromatic competence' for overall chromosome dynamics and identity—and reveal some of the direct biological functions of the enigmatic entity called heterochromatin.

In a first aspect, the results obtained in the experiments of the present invention show that members of the SU(VAR) 3-9 protein family have HMTase activity which identifies them as novel targets for the therapy of proliferative disorders, in particular cancer.

Furthermore, the experiments of the invention demonstrate that the Suv39h HMTases are important for embryonic development and spermatogenesis.

Combined disruption of both Suv39h HMTase genes abolishes H3-K9 methylation at pericentric heterochromatin and induces chromosomal instabilities with an increased risk for tumorigenesis.

In addition, Suv39h double null male mice display complete spermatogenic failure that is largely caused by non-homologous chromosome associations and delayed synapsis, resulting in apoptosis of meiotic prophase cells. Together, these results establish histone H3-K9 methylation as a crucial determinant for pericentric heterochromatin and provide a direct role for the Suv39h HMTases in maintaining a 'heterochromatic competence' that protects chromosome stability during mitosis and meiosis.

The identification of members of the SU(VAR)3-9 protein family, exemplified by human SUV39H1, murine Suv39h1 and murine Suv39h2, as K9 specific histone H3 MTases is the prerequisite for designing assay methods that allow for finding compounds altering, in particular interfering with, higher order chromatin dependent chromosome stability, which is the basis for novel approaches in cancer therapy. (In the following, if not otherwise stated, the term "Suv39h" refers to both the murine and the human protein).

Due to the role of Suv39h1 or Suv39h2 in spermatogenesis, compounds modulating the MTase activitiy of these proteins and thus modulating spermatogenesis may also be used in the treatment of male infertility (using compounds that enhance Suv39h MTase activity) and for reversible male contraception (using compounds that inhibit Suv39h MTase activity).

The present invention relates to a method for identifying a compound that alters higher order chromatin dependent chromosome stability during mitosis and meiosis, said method comprising incubating a substrate for a methyltransferase, in the presence of a methyl donor, with a MTase with Suv39h-like MTase activity, in the presence or absence of a test compound and determining whether the compound modulates the MTase activity.

The group of MTases with Suv39h-like MTase activity (in the following also termed "Suv39h-like MTases") encompasses enzymes which display histone H3 K9 MTase activity or methyltransferase activity for other yet to be identified substrates.

The term "histone H3 K9" is not limited to the human SUV39H or mouse Suv39h substrate (i.e. the methylation site of histone H3 at lysine 9), but is meant to encompass any substrate of the histone or histone variant-type of protein, the methylation of which results in the below-defined epigenetic signal.

Additional members of the group of MTases can be identified by bioinformatic/biochemical techniques and tested biochemically. By way of example, in a first step, by searching data bases for similarities, as described in Example 1. Next, an identified candidate can be verified as a MTase with Suv39h-like MTase activity in biochemical assays similar to or identical with those described in the Examples.

This group of Suv39h-like MTases also encompasses MTases with specificities for other histone H3 residues than K9 or for substrates other than histone H3, which are, like the Suv39h K9 histone H3 HMTase activity observed in the present invention, required for higher order chromatin dependent chromosome stability. This epigenetic signal may be a consequence of histone methylation at lysine 9 on H3 alone; however, it cannot be excluded that MTase activity on undefined substrates or a combination of substrate methylation and other covalent modifications, such as phosphorylation or acetylation, at other histone residues are involved.

In the experiments of the present invention, Suv39h variants with point mutations in the SET domain were shown to confer hyperactive HMTase activity to the protein, these Suv39h variants may be advantageously used in the method of the invention.

In a preferred embodiment, the MTase is mouse Suv39h1 or Suv39h2, most preferably, the MTase is human SUV39H1 or SUV39H2.

Since it has been shown in the present invention that recombinant Suv39h retains HMTase activity, most preferably, a recombinant MTase is employed. Suv39h or Suv39h variants can be produced recombinantly according to standard methods by expression in suitable hosts, e.g. bacteria, yeast, insect or eukaryotic cells and purified, e.g. on glutathione-agarose columns if it has been tagged with GST.

The Suv39h1 and SUV39H1 cDNA sequences are known from the literature (Aagaard et al., 1999), the Suv39h2 cDNA sequence is shown in SEQ ID NO:1; the human SUV39H2 cDNA is defined by the ESTs as shown in SEQ ID NO:3–6.

In the case of testing the compounds for their effect on Suv39h activity, the assay comprises, as its essential features, incubating a histone H3 protein or a histone H3 N-terminal fragment including K9, a methyl donor, e.g. methionine or S-adenosyl-L-methionine, with a preparation containing a Suv39h MTase activity and determining MTase activity in the presence or absence of a test substance.

MTase substrates useful in the method of the invention may be those equivalent to or mimicking the naturally occurring substrates, e.g. biochemically purified histone H3, recombinantly produced histone H3, or a histone H3 peptide that contains the K9 methylation site, or other yet to be identified proteins which act as substrates for Suv39h MTases. Novel Suv39h substrates can be identified by bioinformatic and biochemical techniques and tested using the biochemical assays described in the Examples of the present invention. For example, novel Suv39h substrates can be identified by co-immunoprecipitation techniques. Suv39h proteins or tagged versions of Suv39h proteins can be immunoprecipitated with specific antisera and interacting proteins identified by mass spectroscopy techniques. A yeast two hybrid screen using Suv39h proteins or portions of Suv39h proteins as a bait can also be employed to identify novel interacting protein from a variety of cDNA libraries.

In a preferred embodiment, the histone H3 fragment ARTKQTARKSTGGKAPRKQL (SEQ ID NO:7) is employed. Alternatively, a modified peptide may be used for which the MTase has increased affinity/activity. Such peptides can be designed by exchanging and/or adding and/or deleting amino acids and testing the substrate in serial experiments for MTase affinity/activity.

The methyl group of the methyl donor preferably carries a detectable label, e.g. a radioactive or a chromogenic label, which can be quantified upon transfer to the substrate.

Preferably, the methyl donor is radioactively labelled methionine or S-adenosyl-L-methionine.

Alternatively to using a labelled methyl donor, the substrate, upon methylation by the enzyme, is used to serve as an epitope which can be recognised by a specific antibody and hence be quantified by standard immunoassay techniques, e.g. ELISAs. Antibodies useful in this type of assay can be obtained by using the methylated substrate, preferably a small peptide, e.g. the peptide with the sequence shown in SEQ ID NO:7, as an antigen and obtaining polyclonal or monoclonal antibodies according to standard techniques. The generation and purification of a methyl-specific antibody against the histone H3 lysine 9 position is described in the Materials and Methods section. A suitable H3-K9 methyl antibody was also described by Nakayama et al., 2001.

For small scale applications, the screening method can be based on an assay as described in Example 2, 3 or 4.

In an alternative embodiment, the screening method of the invention utilizes the fact that the methylation of histone H3 at lysine 9 (H3-K9) creates a high-affinity binding site for HP1 proteins. In this embodiment, the substrate, upon methylation, is allowed to bind to HP1 and then incubated with a labelled anti-HP1 antibody. The difference in label intensity between the reaction in the absence or presence of the test compound is indicative for the compound's modulating effect on MTase activity.

HP1 is preferably used in recombinant form. Based on the information of the HP1 cDNA sequence (Jones et al., 2000;

Accession No. BC006821), HP1 is produced recombinantly according to standard technology. The recombinant protein or fragments thereof are used to generate polyclonal or monoclonal antibodies that are employed in this assay format.

In a preferred embodiment, the method of the invention is performed on a high-throughput scale. For this embodiment, the major assay components, in particular Suv39h, are employed in recombinant form.

For the high throughput format, the screening methods of the invention to identify MTase inhibitors, are carried out according to standard assay procedures. Such assays are based on the catalytic transfer, mediated by Suv39h or a Suv39h variant, of a methyl group from a donor to a substrate, e.g. a histone H3 peptide. To achieve this, the substrate, e.g. histone H3 or a variant or fragment thereof, is immobilised on a carrier, usually a microtiter plate, and incubated with recombinant Suv39h or a Suv39h variant and a methyl donor.

The methyl group of the methyl donor carries a label, preferably a chromogenic or radioactive label.

Fluorescent or radioactive labels and the other reagents for carrying out the enzymatic reaction on a high-throughput scale are commercially available and can be employed according to the supplier's instructions (e.g. Molecular Probes, Wallac). Examples for suitable fluorescent labels are coumarin derivatives, e.g., 7-amino-4-methylcoumarin or 7-amino-4-trifluoromethylcoumarin. The radioactive label may be a $^{14}C$ or a $^{3}H$ atom. Upon transfer of the methyl group to the substrate by Suv39h, in the case of a chromogenic reagent, the methyl donor changes colour which can be quantified. In the case of using a radioactive methyl donor, the methyl group is transferred to the substrate and can be directly quantified.

The specific assay design depends on various parameters, e.g. on the size of the substrate used. In the the case of using a short peptide, the fluorescence quenching or the fluorescence resonance energy transfer methods are examples for suitable assay technologies, as described below.

The substrate may be tagged, e.g. with biotin, the reaction is then carried out in solution and then transferred to streptavidin coated microtiter plates, e.g. in the case of a radioactive methyl group, "flash" plates, the material of which contains the scintillant, or plates which are coated with scintillant. Thus the level of methylation of the substrate can be quantified in a suitable scintillation machine/reader. Alternatively, the assay can be carried out in the streptavidin coated "flash" plates with the biotinylated substrate already bound to the plates. This type of assay may also be conducted in the form of a so-called "homogenous assay" (an assay type which does not require intermediate transfer and washing steps) e.g. by using microbeads that are coated with scintillant and streptavidin, to which the biotinylated substrate is bound.

Similarly to biotin, other commonly used tags, e.g. Flag, Myc, HA, GST, that are suitable to immobilize the substrate to the plate that is coated with the tag-specific antibody, may be used in the above-described assays.

In a variant, this assay is conducted in the format ELISA type assay; in this case, a methyl-specific antibody is used to detect the amount of methylated substrate bound to the plate.

Alternatively, the plate is coated with an antibody against the methylated substrate to capture the methylated substrate; the substrate is also either tagged or chromogenically labeled and the amount of bound methylated tagged/labeled substrate can be quantified either by a tag-specific antibody or by measuring the level of chromogenic label. By way of example, the substrate is a linear or a branched peptide, e.g. [TARKST]$_4$-K$_2$-K-cys) that is labeled with a chromogenic label, e.g. europium, and upon methylation by a Suv39h-like MTase becomes an epitope for a Lys9-methyl specific antibody (see materials and methods) immobilised on a carrier (e.g. microtiter plate). The non-captured substrate is washed away, the europium label is then cleaved and its fluorescence enhanced and the level of fluorescence is calculated by time resolved fluorescence. The level of fluorescence is directly related to the level of methylated substrate (FIG. 17).

An alternative embodiment is based on the principle that methylation of the peptide may alter its sensitivity to cleavage by a protease. Utilizing this principle, the fluorescence quenching (Resonance Energy Transfer "RET") assay may be employed to determine the amount of methylation of peptidic substrates. In a first step, a Suv39h peptidic substrate, which contains the methylation site and a recognition/cleavage site for a defined protease, that is sensitive to modification (in the particular case, methylation of the lysine) of the recognition/cleavage site, e.g. trypsin or LysC. The peptide carries a fluorescent donor near one end and an acceptor near the other end. In the uncleaved substrate, the fluorescence of the substrate is quenched by the persisting intramolecular RET between donor and acceptor. Upon cleavage of the (unmethylated) substrate by the protease, the cleavage products are released from RET quenching and a fluorescence signal is generated. Methylation of the substrate abolishes the ability of the protease to cleave the substrate. Thus, abolishment of the protease activity (which is proportional to methylation) is reflected by signal repression, in case of total protease inhibtion, total signal repression to the basal level.

An assay of this type may be carried out as follows: the solution of the labeled substrate (e.g. the peptide labeled with 4-[[4'-(dimethylamino)phenyl]azo]benzoic acid (DABCYL) at the one end and with 5-[(2'-aminoethyl) amino]naphtalenesulfonic acid (EDANS) at the other end or labeled with benzyloxycarbonyl at the one end and with 4-aminomethylcoumarin at the other end) in assay buffer is transferred into each well of black 96-well microtiter plates. After addition of the test substances in the defined concentration, the MTase and the methyldonor are added to the wells. After incubation under reaction conditions and for a period of time sufficient for the methylation reaction, e.g. for 40 min at room temperature, the protease, e.g. trypsin, is added and allowed to react under suitable conditions, finally, the fluorescence is measured in a fluorometer at the excitation wavelength, e.g. at 340 nm, and at the emission wavelength, e.g. at 485 nm.

In the case of using the FRET assay, the following commercially availabe labeling pairs are suitable for the method of the invention: Europium (Eu) and Allophycocyanin (APC), Eu and Cy5, Eu and PE (Wallac, Turku, Finland). If a test substance is a modulator of the MTase activity, there will be, depending on the detection system and depending on whether the test substance has an inhibiting or an activating effect, a decrease or an increase in the detectable signal as compared to a control sample in the absence of a test substance. In the high-throughput format, compounds with a modulating effect Suv39h MTase activity can be identified by screening test substances from compound libraries according to known assay principles, e.g. in an automated system on microtiter plates.

By providing a method to identify compounds which exert their effect by directly modulating, in particular by inhibiting, a Suv39h-like MTase, the present invention provides a basis for inhibiting the proliferation of rapidly dividing animal cells, in particular tumour cells.

The compounds identified in the above methods, which are also subject of the invention, have the ability to interfere with chromosome stability and high fidelity chromosome segregation by modulating the MTase activity of Suv39h.

In a preferred embodiment, the compounds of the invention are inhibitors of Suv39h HMTase activity.

Preferably, the compounds are specific modulators of Suv39h, in particular Suv39h1 or Suv39h2.

The present invention also relates to compounds, which act as modulators of a Suv39h-like MTase activity, in particular modulators of Suv39h, for use in human therapy, in particular cancer therapy.

Compounds inhibiting Suv39h HMTase activity result in decreased genome stability and can be used in therapy for targeting dividing cells, in particular highly proliferative tumour cells. They are preferably administered in combination with other genome destabilising agents, e.g. mitose inhibitors like tubulin binders (taxanes, e.g. taxol, Paclitaxel; or epithelones). SUV39H inhibitors may also be used jointly with or before the application of conventional tumour therapies, e.g. radiotherapy or chemotherapy, in particular DNA damaging agents, in order to pre-sensitize the tumour cells. By destabilizing the cell's genome, the SUV39H inhibitors make the cell more susceptible to the parallel/subsequent treatment.

The SUV39H inhibitors will preferably be used in a combination therapy and applied in consecutive and transient treatments. Since the development of B-cell lymphomas in Suv39h double null mice only occurs with a late onset (i.e. after 9 months of age), transient treatments with SUV39H inhibitors should not induce an immediate increase in tumor risk but rather weaken overall genomic stabilities of highly proliferating cells.

Likewise, agents which enhance Suv39h HMTase activity can be used to stabilise the genome of inherently unstable cells, rendering them less prone to acquiring proliferation promoting mutations. A model for Suv39h function and effects of inhibition or enhancement of Suv39h enzymes is shown in FIG. 8.

The efficacy of compounds identified as Suv39h modulators can be tested for in vivo efficacy in mammalian cells with Suv39h double null cells serving as a positive control. Compounds effective in cancer therapy should interfere with chromosome stability and segregation, which can be measured by karyotyping, e.g. by analysing the DNA content by FACS or standard cytological techniques. Substances whose potential for therapeutic use has been confirmed in such secondary screens can be further tested for their effect on tumour cells. To test the inhibition of tumour cell proliferation, primary human tumour cells are incubated with the compound identified in the screen and the inhibition of tumour cell proliferation is tested by conventional methods, e.g. bromo-desoxy-uridine or $^3$H thymidine incorporation. Compounds that exhibit an anti-proliferative effect in these assays may be further tested in tumour animal models and used for the therapy of tumours.

Compounds intended for male fertility applications can be tested in animal models described by Vigil et al., 1985, in animal models developed for experimental studies of human spermatogenesis, as described by Weinbauer et al., 2001, or in animal models that mimic human male reproductive defects, as described by Lamb and Niederberger (1994). Guidance for a valid application of animal data to the assessment of human reproductive disorders is given by Working, 1988.

Toxicity and therapeutic efficacy of the compounds identified as drug candidates by the method of the invention can be determined by standard pharmaceutical procedures, which include conducting cell culture and animal experiments to determine the $IC_{50}$, $LD_{50}$, the $ED_{50}$. The data obtained are used for determining the human dose range, which will also depend on the dosage form (tablets, capsules, aerosol sprays, ampules, etc.) and the administration route (oral, buccal, nasal, paterental, rectal or, in the case of temporary male contraceptive applications, local sustained release form applications, e. g. slow-releasing micropellets that are implanted into or adjacent to the gonads). A pharmaceutical composition containing the compound as the active ingredient can be formulated in conventional manner using one or more physiologically active carriers and excipients. Methods for making such formulations can be found in manuals, e.g. "Remington Pharmaceutical Sciences".

As Suv39h is required to maintain a stable karyotype, it can be considered as a tumour suppressor gene. If SUV39H mutations also prove to be a factor underlying cellular transformation events in humans, which is strongly indicated by the analysis of Suv39h double null mice in developing B-cell lymphomas, it can be expected that the re-introduction of a wild type Suv39h gene by gene therapy results in increased genomic stability delaying or inhibiting cancer progression.

For gene therapy, the Suv39h DNA molecules may be administered, preferably contained on a plasmid in recombinant form, directly or as part of a recombinant virus or bacterium. In principle, any method of gene therapy may be used for applying Suv39h recombinant DNA, both in vivo and ex vivo.

Examples of in vivo administration are the direct injection of "naked" DNA, either by intramuscular route or using gene guns. Examples of recombinant organisms are vaccinia virus or adenovirus. Moreover, synthetic carriers for nucleic acids such as cationic lipids, microspheres, micropellets or liposomes may be used for in vivo administration of nucleic acid molecules coding for the Suv39h polypeptide.

Since it has been shown in the present invention that Suv39h mediates dynamic transitions in higher-order mammalian chromatin largely through its intrinsic HMTase activity, histone H3-K9 methylation (H3-K9 Me) represents an important epigenetic imprint for chromosome dynamics during cell division. Hence, antibodies specific for H3-K9 Me can be used to screen cells/patients for heterochromatin based genome instabilities. In essence, H3-K9 methylation specific antibodies can be used as a diagnostic tool for human diseases associated with aberrant gene expression and genomic instability through chromosome mis-segregation or with aberrant definition or organisation of heterochromatin.

BRIEF DESCRIPTION OF THE DRAWINGS/FIGURES

FIGS. 1A,B: HMTase activity of transfected and recombinant SUV39H1 and Suv39h1 proteins.

FIGS. 2A–C: Specific HMTase activity of the SET domain of mammalian SU(VAR)3-9 related proteins.

FIGS. 3A–C: Histone H3 lysine 9 is the major site for in vitro methylation by recombinant Suv39h1.

FIGS. 4A–C: Targeting of Suv39h1 and Suv39h2 in the mouse germline.

FIGS. 5A,B: Analys is of Suv39h double null PMEFs.

FIGS. 6A,B: Aberrant mitoses in Suv39h double null PMEFs.

FIGS. 7A,B: Increased phosH3 phosphorylation in Suv39h double null PMEFs.

FIG. 8: Model for Suv39h HMTase function.

FIGS. 9A1, 9A2, 9B–9D: Generation and genotyping of Suv39h1- and Suv39h2- deficient mice.

FIGS. 10A–D: Chromosomal instabilities in Suv39h dn PMEFs.

FIGS. 11A–C: Development of B-cell lymphomas in Suv39h mutant mice.

FIGS. 12A,B: Suv39h-dependent H3-K9 methylation at pericentric heterochromatin.

FIGS. 13A,B: Spermatogenic failure and H3-K9 methylation in germ cells of Suv39h dn mice.

FIGS. 14A–K: Illegitimate associations and delayed synapsis of Suv39h dn meiotic chromosomes.

FIGS. 15A–F: Aberrant function of the Y chromosome during meios of Suv39h dn spermatocytes.

FIGS. 16A,B: Model for a 'heterochromatic competence' in protecting chromosome stability.

FIGS. 17A,B: Schematic illustration of a screening method for identifying Suv39h modulators.

DETAILED DESCRIPTION OF THE INVENTION

Materials and Methods a) Sequence alignments and secondary structure predictions The SET domains of human SUV39H1 (Aagaard et al., 1999), Drosophila SU(VAR)3-9 (Tschiersch et al., 1994) and *S. pombe* CLR4 (Ivanova et al., 1998) were used as a multiple starting alignment for database similarity searches using Profile (Birney et al., 1996), hidden Markov (Eddy, 1998) and position-specific iterative BLAST (Altschul et al., 1997) methods (representative listings are available from the SET domain page of the SMART WWW-server (Schultz et al., 2000). These searches revealed significant similarities to six plant proteins (accession numbers Q43088, 065218, P94026, 080013, AAC29137 and AC007576 12) described as putative lysine N-methyltransferases. For example, a PSI-BLAST search with the *S. pombe* hypothetical protein SPAC3c7.09 as query identified these plant sequences and well-known SET domain sequences within ten rounds using an E-value inclusion threshold of 0.001. The same search also revealed the presence of a SET domain in YHR109w, which is known to encode a cytochrome c MTase (Martzen et al., 1999), within three rounds. Consensus secondary structures were predicted by described algorithms (Frishman and Argos, 1997).

b) Epitope-tagged SUV39H1 proteins in HeLa cells

The HeLa cell lines overexpressing full-length (myc)3-SUV39H1 (aa 3–412) or (myc)3-Nchromo (aa 3–118) have been described (Aagaard et al., 1999; Melcher et al., 2000). Nuclear extracts were immunoprecipitated with anti-myc antibody beads (Aagaard et al., 1999), and approximately 1–3 µg of matrix-bound (myc)3-tagged SUV39H1 proteins were used for in vitro HMTase assays.

c) Generation and purification of GST-fusion proteins

The GST-Suv1(82–412) product expressed from the pGEX-2T vector (Pharmacia) as a glutathione-S-transferase (GST) fusion protein has been described (Aagaard et al., 1999). Additional GST constructs were generated by transferring BamHI-EcoRI PCR amplicons into pGEX-2T, encoding in-frame fusions for Suv39h1(7–221), SUV39H1 (82–412), SUV39H1(82–378) ΔC-tail, SUV39H1(255–412) Δcys, Suv39h2(157–477) (O'Carroll et al., 2000), CLR4 (127–490) (Ivanova et al., 1998), EZH2(382–747) (Laible et al., 1997) and HRX(3643–3969) (Tkachuk et al., 1992). Short internal deletions ($\Delta$NHSCDPN$_{323-329}$ and $\Delta$GEELTFDY$_{358-365}$) or point mutations within the -$_{320}$H$\phi\phi$NHSC$_{326}$-motif were directly engineered in the GST-SUV39H1(82–412) plasmid by double PCR mutagenesis. All constructs were confirmed by sequencing.

Recombinant proteins were expressed in 11 cultures of *E.coli* strain BL21 and solubilized in 10 ml RIPA buffer (20 mM Tris pH 7.5, 500 mM NaCl, 5 mM EDTA, 1% NP-40, 0.5% sodium deoxycholate) containing a full set of protease inhibitors (Boehringer Mannheim) and lysozyme (5 mg/ml; Sigma) by freeze-thawing in liquid N2, followed by sonication. Soluble proteins were cleared by centrifugation, purified with 800 µl glutathione Sepharose beads (Pharmacia) and washed twice in RIPA buffer. Protein concentration was determined by Coomassie staining of SDS-PAGE gels. Matrix-bound fusion proteins were used immediately for in vitro HMTase assays or stored at 4° C.

d) In vitro histone methyltransferase (HMTase) assay

In vitro HMTase reactions were modified based on described protocols (Strahl et al., 1999) and carried out in a volume of 50 µl of methylase activity buffer (MAB: 50 mM Tris pH 8.5, 20 mM KCl, 10 mM MgCl$_2$, 10 mM β-ME, 250 mM sucrose), containing 10 µg of free histones (mixture of H1, H3, H2B, H2A and H4; Boehringer Mannheim) as substrates and 300 nCi S-adenosyl-[methyl-$^{14}$C]-L-methionine (25 µCi/ml) (Amersham) as methyl donor. 10 µg of matrix-bound GST-fusion proteins were routinely used to assay for HMTase activity. After incubation for 60 min. at 37° C., reactions were stopped by boiling in SDS loading buffer, and proteins were separated by 15% or 18% SDS-PAGE and visualised by Coomassie staining and fluorography.

HMTase assays with individual histones (Boehringer Mannheim), insulin (Sigma) or N-terminal peptides were performed with 5 µg of substrate. The following peptides were used: wild-type N-terminus of human histone H3 (ARTKQTARKSTGGKAPRKQL) (SEQ ID NO:7) and mutant peptide which changes lysine 9 (bold) to leucine; N-terminus of human CENP-A (MGPRRRSRKPEAPRRRSPSP) (SEQ ID NO:8) (Sullivan et al., 1994); N-terminus of rat macro-H2A (MSSRGGKKKSTKTSRSAKAG) (SEQ ID NO:9) (Pehrson and Fried, 1992).

Peptide microsequencing of the in vitro methylated wild-type H3 N-terminal peptide and determination of $^3$H-incorporation of individual amino acids by scintillation counting was done as described (Strahl et al., 1999). Targeting of the Suv39h1 and Suv39h2 gene loci in embryonic stem cells Partial genomic clones of the Suv39h1 locus (X chromosome) and of the Suv39h2 locus (chromosome 2) (O'Carroll et al., 2000) were used to generate short and long arms of homology, in a strategy to produce in-frame fusion proteins of the first 40 amino acids of Suv39h1 or of the first 113 amino acids of Suv39h2 with β-galactosidase (LacZ) modified with a nuclear localization signal (nls). For targeting, a 1.2 kb Pfu PCR amplicon and a 5.4 kb SacI DNA fragment were derived from the genomic subclone gSuv39h1 #18, and a 1.3 kb Pfu PCR amplicon and a 5.0 kb MluI/ApaI DNA fragment were prepared from the genomic subclone gSuv39h2 #28 (see FIGS. 9A1,A2). The pGNA-derived targeting cassettes contained an RSV-neomycin (neo) gene for positive selection and two polyadenylation sites. The diphtheria toxin A (DTA) gene under the control of the MCI promoter was used to select against random integration and was inserted 3' of the long arms of homoloy. After linearisation with NotI, Suv39h1 and Suv39h2 targeting constructs were electroporated into feeder-dependent R1 and E14.1 (129/Sv) embryonic stem (ES) cells.

After selection, G418-resistant ES cell colonies were screened for homologous recombination by nested PCR using primers external to the short arms of Suv39h1 (PCR1: 5'-ATGGGGGCAGGGTTTTCGGGTAGAC, SEQ ID NO:10; PCR2: 5'-AAATGGTATTTGCAGGCCAC-TTCTTG, SEQ ID NO:11) or of Suv39h2 (PCR1: 5'-GAAAAGGTTGTTCTCCAGCTC, SEQ ID NO:12; PCR2: 5'-GGATGGGATGGTGG-AATGGTTTTTAT, SEQ ID NO:13) and primers within the lacZ gene (lacZ-PCR1: 5'-AACCCGTCGGATTCTCCGTGGGAAC, SEQ ID NO:14; lacZ-PCR2: 5'-CTCAGGAA-GATCGCACTCCAGCC, SEQ ID NO:15).

Successful targeting was confirmed by Southern blot analysis of PvuII-digested ES cell DNA with a ≈500 bp external Suv39h1 intron probe, generated with the primers g24r (5'-GACTGC-CTAGTCTGGCACTGAACT, SEQ ID NO:16) and g13 (5'-GATCACTGCGTACATATAC-ACTGAT, SEQ ID NO:17), or of HindIII-digested ES cell DNA with a ≈500 bp external Suv39h2 exon/intron probe, generated with the primers Plf (5'-TAGACTT-CTACTACATTAACG, SEQ ID NO:18) and Plr (5'-GATGTCAGTGGCTATGAATG, SEQ ID NO:19). These DNA probes detect a 4.5 kb fragment from the wildtype Suv39h1 allele and a 4.0 kb fragment from the targeted allele, or 11 kb and 6.1 kb fragments from the Suv39h2 wildtype and targeted alleles (see FIG. 9B).

f) Generation and genotyping of Suv39h1- and Suv39h2- deficient mice

Several independently targeted ES cell clones gave rise to chimaeric mice which passed the mutations through the germline. Suv39h1−/− and Suv39h2−/− mice were intercrossed to produce compound Suv39h mutant mice (e.g. Suv39h1−/−, Suv39h2+/−; null1/het2), which were then mated to generate Suv39h double null (dn) mice. All mice described in this study were maintained on a mixed genetic background of 129/Sv and C57B1/6J origin.

Genotyping of mutant mice was done by Southern blot analysis as described above. Protein blot analysis of nuclear extracts from mouse testes with α-Suv39h1 and α-Suv39h2 antibodies was performed as described previously (O'Carroll et al., 2000).

g) Generation and analysis of Suv39h double null primary mouse embryonic fibroblasts (PMEFs)

PMEFs were derived from day E12.5 Suv39h double null embryos obtained after intercrossing Suv39h1$^{-/-}$/Suv39h2$^{+/-}$compound mutant mice. As controls, PMEFs were prepared from wild-type embryos of the same genetic background. For cell cycle profiles and growth curve analysis, passage 2 PMEFs were analyzed as described (Xu et al., 1999). Staining of PMEF interphase chromatin with α-phosH3 (Hendzel et al., 1997) antibodies was done in unpermeabilized cells as described (Melcher et al., 2000). For the biochemical analysis, total nuclear extracts were precalibrated by Ponceau staining, immuno-blotted with α-H3 (Upstate Biotechnology) and α-phosH3 (Hendzel et al., 1997) antibodies and visualised by peroxidase staining using Enhanced ChemiLuminescence (ECL) (Amersham).

h) Growth curves and FACS analyses of PMEFs

To analyze the proliferative potential of wild-type and mutant cells, PMEFs were seeded onto 10 cm² dishes. Over the next 30 passages, $3 \times 10^5$ cells were continually reseeded every third day onto a new 10 cm² dish (3T3 protocol), and their doubling rates determined. The DNA profiles of passage 3 and passage 8 PMEF cultures were obtained by FACS of ethanol-fixed and propidium-iodide stained cells, using chicken erythrocyte nuclei (Becton Dickinson) as an internal standard.

i) Bone marrow culture and FACS analysis of B-cell lymphoma cells

Bone marrow cells from wt and Suv39h dn mice were cultivated for two weeks in StemPro-34 SFM medium (Life Technologies) supplemented with IL-3 (10 ng/ml), IL-6 (5 ng/ml), SCF (100 ng/ml), FLT 3 ligand (20 ng/ml), GM-CSF (1 ng/ml) (all from R&D Systems), 10 μM dexamethasone (Sigma) and IGF-1 (40 ng/ml) (Sigma). Cultures were grown at densities of ≈$3 \times 10^6$ cells per ml, and purified from differentiated and dead cells by Ficoll-Paque gradient centrifugation (Pharmacia).

Primary lymphoma cells were obtained from spleen and lymph nodes using a 70 μm Nylon Cell Strainer (Becton Dickinson), and cultivated in Iscove's modified Dulbecco's medium (IMDM) supplemented with 5% heat-inactivated fetal calf serum, 2 mM glutamine and 1% penicillin-streptomycin (all Gibco-BRL). Single cells suspensions were grown O/N in medium additionally containing 50 μM β-mercaptoethanol and 5% conditioned supernatant from rIL-7 producing J558L cells.

The identity of the tumor cells was determined by FACS analyses using antibodies (all from Pharmingen) that detect specific cell surface markers. All tumor cells were double positive for the B-cell markers B220-low (RA3-6B2) and CD19 (1D3), but negative for the T-cell markers CD3 (145-2C11), CD4 (RM4-5), CD8 (53–6.7), or for the granulocyte/ macrophage markers Gr-1 (RB6-8C5), Mac-1 (M1/70) and for a marker of the eythroid lineage, Ter-119. The majority of the B-cell lymphoma cells were also double positive for CD43 (S7) and IgM (R6-60.2), while some clonal cultures displayed reactivity towards CD5 (53-7.3). These FACS profiles characterize the Suv39h-mediated tumors as being similar to chronic lymphoid leukemia in humans (Foon and Gale, 1995).

j) Chromosome spreads and karyotype analyses

PMEF and tumor cell karyotypes were analyzed on colchicine-arrested and Giemsa-stained metaphase chromosome spreads.

Metaphase spreads of spermatogonia and spermatocytes were prepared from isolated seminiferous tubule fragments which had been hypotonically swollen with 1% sodium citrate for 10 min. at RT and fixed O/N at 4° C. with Carnoy's solution (75% methanol, 25% acetic acid). After incubation of seminiferous fragments in 60% acetic acid for 2 min., a single cell suspension was generated by repeated pipetting, transferred onto a pre-heated (60° C.) glass slide, and cells were spread by mechanical shearing with a glass hockey stick.

k) Generation and purification of α-methH3-K9 antibodies

To generate methyl-specific antibodies against the histone H3 lysine 9 position, a hexameric peptide was generated, -TARK(Me)$_2$ST-cys, containing a di-methylated lysine (Bachem) and a terminal cysteine. To increase the antigenicity and immunogenicity, a 'branched' peptide that consists of four -TARK(Me)2ST-'fingers' which are linked at their C-termini via lysine residues was also synthesized. The sequence of this 'branched' peptide is [TARK(Me)$_2$ST]$_4$-K$_2$-K-cys. Peptides were coupled to KLH and rabbit polyclonal antisera were raised, indicating that the 'branched' peptide was much more immunogenic than the linear peptide.

Crude antisera from two positive rabbits (#2233 and #2236) were batch-absorbed against a 'branched', but unmodified control peptide, followed by affinity purification against the di-methylated 'branched' antigen that had been crosslinked to a Poros™ column (Lachner et al., 2001). Bound antibodies were eluted with 100 mM glycine pH 2.5 and neutralised with ⅒ vol. of 2 M Hepes pH 7.9. The methyl-specificity of the antibodies was confirmed on slot-blots presenting unmodified or K9-dimethylated histone H3 peptides and on protein blots containing nuclear extracts from wt or Suv39h dn PMEFs. The affinity-purified α-methH3-K9 antibodies (concentration ≈0.6 mg/ml) can be used at a 1:1,000 dilution for protein blot analysis or at 1:1,000 to 1:5,000 dilutions for indirect immunofluorescence.

l) Immunofluorescence of interphase chromatin and metaphase chromosomes

Passage 6 PMEFs were fixed with 2% p-FA for 10 min. on ice, washed, incubated with blocking solution (PBS, 2.5% BSA, 10% goat serum and 0.1% Tween20) for 30 min at RT and stained O/N at 4° C. with the α-methH3-K9 antibodies. After several washes with PBS containing 0.2% BSA and 0.1% Tween20, the primary antibodies were detected with Alexa Fluor488-conjugated goat αrabbit antibodies (Molecular Probes). DNA was counterstained with 4',6'-diamidino-2-phenylindole (DAPI), and samples were embedded in Vectashield (Vector Laboratories).

For preparation of metaphase chromosomes, bone marrow cells or primary tumor cells were arrested by colchicine treatment (0.5 mg/ml) (Sigma) for 2.5 hrs., followed by hypotonic swelling in 0.6% KCl or RBS buffer (10 mM TrisHCl pH 7.4; 10 mM NaCl; 5 mM $MgCl_2$) for 15 min. at 37° C. and centrifugation for 8 min. at 2000 rpm in a Cytospin (Shandon). Spreaded cells were immediately fixed with icecold 2% p-FA in PBS for 15 min., washed twice and stained with the (α-methH3-K9 antibodies as described above.

m) Testes histology

Testes were dissected from adult mice, fixed in Bouins fluid (75% saturated picric acid, 5% glacial acetic acid, 9.3% formaldehyde) and stained with haematoxylin/eosine. Staging of the seminiferous tubules was performed according to Oakberg (1956) and Russell et al. (1990). FISH analyses with mouse major satellite DNA probes were done as recently described (Scherthan et al., 1996), and Tunel assays were performed using the DeadEnd apoptosis detection system (Promega). In addition, testis cryosections (O'Carroll et al., 2000) were also analyzed by immunohistochemistry with α-Scp, α-Hp1β, α-phosH3 and α-meth H3-K9 antibodies.

n) Immunofluorescence of germ cells and meiotic chromosome spreads

Chromosome spreads of spermatogenic cells were prepared according to Peters et al. (1997a) with some minor modifications. A single germ cell suspension was obtained in DMEM medium by mechanical disruption of isolated seminiferous tubules. After serveral washes and hypotonic swelling in hypobuffer (30 mM TrisHCl pH 8.2, 50 mM sucrose, 17 mM sodium citrate) for 10 min. at RT, cells were resuspended in 100 mM sucrose, 15 mM TrisHCl pH 8.2 and spreaded on precleaned slides covered by a thin film of 1% p-FA containing 5 mM borate pH 9.2 and 0.15% TritonX-100. Slides were dried slowly in a humid chamber for ≈2 hrs and stored at −80° C. Classification of meiotic sub-stages was performed according to the changing morphology of autosomes and sex chromosomes as described (Peters et al., 1997b).

Double-labelling immunofluorescence of these germ cell preparations was performed by sequential incubation with rabbit polyclonal (α-methH3-K9 antibodies and with goat α-rabbit Alexa568-conjugated secondary antibodies. After a brief fixation in 1% p-FA, samples were incubated with rabbit polyclonal α-Scp3 antibodies (Lammers et al., 1995) that were visualized with goat α-rabbit Alexa488-conjugated secondary antibodies. In addition, co-stainings were also done with α-Scp3 and α-Scp1 (Offenberg et al., 1991) (see FIGS. 14A–C), and α-Scp3 and α-HP1β, (Wreggett et al., 1994), and α-Scp3 and α-phosH3 (Hendzel et al., 1997) antibodies.

o) EM analysis

Preparation and silver staining of SC complexes from spreaded germ cells (see above) was performed according to Peters et al. (1997a), and samples were analyzed on a Jeol 1200 EKII transmission electron microscope.

EXAMPLE 1

Sequence Similarity of SET Domains with Plant Methyltransferases

Using the SET domains of the SU(VAR)3-9 protein family as a starting alignment, significant sequence and secondary structure similarities (see Methods) to six plant protein methyltransferases were detected. Although some of these plant sequences have been classified as potential histone lysine N-methyltransferases, only one had been functionally characterised but was found to lack HMTase activity (Klein and Houtz, 1995; Zheng et al., 1998).

Detected were amino acid and secondary structure [β-sheet (b) or αhelix (h)] similarities of the C-terminal halves of SET domain sequences from human SUV39H1 (Aagaard et al., 1999) (AF019968), murine Suv39h1 (Aagaard et al., 1999) (AF019969), murine Suv39h2 (O'Carroll et al., 2000), (AF149205), Drosophila SU(VAR) 3-9 (Tschiersch et al., 1994) (P45975), a *C. elegans* SU(VAR)3-9-like ORF C15H11.5 (CAB02737), *S. pombe* CLR4 (Ivanova et al., 1998) (O74565), human EZH2 (Laible et al., 1997) (Q15910), the human trithorax homologue HRX (Tkachuk et al., 1992) (Q03164), and MTases from *P. sativum* (rubisco 1s-MT; Q43088) (Klein and Houtz, 1995; Zheng et al., 1998) and *A.thaliana* (O065218). The plant MTase sequences contain an insertion of approximately 100 amino acids in the middle of the SET domain.

EXAMPLE 2

HMTase Activity of Transfected and Recombinant SUV39H1 and Suv39h1 Proteins

To investigate whether the SET domain of human SUV39H1 has enzymatic activity, histones were tested as possible substrates for in vitro methylation. Using HeLa cell lines 'stably' expressing triple myc-tagged full-length SUV39H1 (aa 3–412), the ectopic protein was enriched from nuclear extracts by immunoprecipitation with anti-myc beads (see FIG. 1A, arrowhead top panel) and probed for activity to transfer a labeled methyl group from S-adenosyl-[methyl-$^{14}$C]-L-methionine to free histones according to described conditions (Strahl et al., 1999). Reaction products were separated by SDS-PAGE and visualised by fluorography, indicating selective transfer of the methyl-label to H3 (FIG. 1A, lower panel). By contrast, no signals were detected with extracts from a HeLa cell line that expresses only the N-terminal third of SUV39H1 (aa 3–118) or with extracts from HeLa control cells. To confirm that the HMTase activity is an intrinsic property of SUV39H1 and not mediated by a SUV39H1-associated factor, the in vitro HMTase reactions was repeated with recombinant products that were purified as GST-fusion proteins from *E.coli* (see FIG. 1B, arrowheads top panel). For this analysis, murine Suv39h1, which is 95% identical to human SUV39H1 (Aagaard et al., 1999) was used. A purified GST-product comprising aa 82–412 maintained HMTase activity (although at a reduced level as compared to transfected SUV39F1), whereas a purified GST-product comprising aa 7-221 proved negative, even at higher protein concentrations (FIG. 1B, lower panel). These results suggest that the HMTase activity resides in the C-terminal SET domain.

In FIG. 1A, triple myc-tagged full-length human SUV39H1 (aa 3–412) or a C-terminally truncated SUV39H1 protein (aa 3–118) were immunoprecipitated from 'stably' transfected HeLa cell lines with anti-myc antibody beads and used in in vitro HMTase reactions with free histones as substrates and S-adenosyl-[methyl-$^{14}$C]-L-methionine as methyl donor. The Coomassie stain (top panel) shows purified proteins by arrowheads and free histones by dots. Fluorography (bottom panel, FIG. 1A) indicates HMTase activity of (myc)3-SUV1(3–412).

In the experiments shown in FIG. 1B, recombinant GST-fusion proteins encoding different domains of murine Suv39h1 were used in increasing protein concentrations for in vitro HMTase reactions as described above.

EXAMPLE 3 a) Definition of a catalytic motif in the SET domain of human SUV39H1

Similar to the recombinant murine GST-Suv39h1 (82–412) product, the corresponding human SUV39H1 fusion protein [GST-SUV39H1(82–412)] is catalytically active (see FIG. 2). Short internal deletions (ΔNHSCDPN$_{323-329}$; ΔNHSC and ΔGEELTFDY$_{358-365}$; ΔGEEL) were introduced into the two conserved regions of the SET domain core in GST-SUV39H11(82–412) and, in addition, mutants that lack the C-terminal tail (ΔC-tail) or the SET-associated cysteine-rich region (Δcys) were also generated. All mutant proteins failed to demonstrate HMTase activity (see FIGS. 2/1A). To investigate enzyme function of the SET domain in more detail, point mutations were introduced into the most highly conserved motif. In vitro HMTase assays indicated that all point mutations, with the exception of one, abolished enzymatic activity. Surprisingly, the latter mutation (H320R) resulted in an hyperactive enzyme with approximately 20-fold increased activity. The data obtained define the $_{320}$HϕϕNHSC$_{326}$ motif in the SET domain as an important catalytic site.

b) Specific HMTase activity of the SET domain of mammalian SU(VAR)3-9 related proteins Because the SET domain is one of the most conserved protein motifs in chromatin regulators (Stassen et al., 1995; Jenuwein et al., 1998), it was next analyzed whether SU(VAR)3–9 family members or other SET domain proteins contain HMTase activity. GST-fusion products of the extended SET domains of *S.pombe* CLR4 (Ivanova et al., 1998), human EZH2 (Laible et al., 1997) and human HRX (Tkachuk et al., 1992) were generated that would correspond to GST-SUV39H1(82–412) (see FIG. 2B). Interestingly, (GST-CLR4(127–490) displayed pronounced HMTase activity at three- to five-fold increased levels (see FIG. 2C) as compared to the recombinant SUV39H1 product, consistent with CLR4 carrying an arginine at the hyperactive position. By contrast, both GST-EZH2(382–747) and GST-HRX(3643–3966) had undetectable HMTase activity towards free histones (FIG. 2C), whereas a comparable GST product generated from the recently isolated murine Suv39H2 gene (O'Carroll et al., 2000), GST-Suv39h2 (157–477), was as active as GST-SUV39H1(82–412). EZH2 lacks the C-terminal cysteines, and HRX does not contain the SET associated cysteine-rich region (FIG. 2B). Both of these cysteine domains are present in CRL4, Suv39h2 and SUV39H1. In agreement with the mutational analysis of SUV39H1, it thus appears that HMTase activity towards free histones requires the combination of the SET domain with adjacent cysteine-rich regions, and is a quality found in only a restricted number of SET domain containing proteins.

In FIG. 2A, approximately 10 μg of the indicated fusion proteins encoding GST-SUV1(82–412) (=human SUV39H1) and seven SET domain mutants were used in in vitro HMTase reactions with free histones as outlined in FIG. 1. For the hyperactive H320R mutant, only 1 μg (10%) of the corresponding fusion product was used. FIG. 2 shows a diagram representing the domain structures of CLR4, Suv39h2, SUV39H1, EZH2 and HRX proteins, with the arrowheads demarcating the N-terminal fusion to GST. Cysteine-rich regions are indicated by grey stippling.

In FIG. 2C, approximately 10 μg of the indicated fusion proteins encoding *S. pombe* CLR4 [GST-CLR4(127–490)], murine Suv39h2 [GST-Suv2(157–477)], human EZH2 [GST-EZH2(382–747)], human HRX [GST-HRX (3643–3969)] and human SUV39H1 [GST-SUV1(82–402)] were used in in vitro HMTase reactions with free histones as outlined in FIG. 1.

EXAMPLE 4

Lysine 9 of the H3 N-terminus is the Major Site for in Vitro Methylation by Recombinant Suv39h1

The above Examples indicated that the HMTase activity of mammalian SU(VAR)3–9 related proteins is selective for H3 under the chosen assay conditions. To examine this finding in more detail, in vitro methylation reactions were performed with individual histones, using GST-Suv39h1 (82–412) as an enzyme. As shown in FIG. 3A, H3 is specifically methylated by GST-Suv39h1(82–412), whereas no signals are detected with H2A, H2B or H4. A weak signal is present if H1 was used as the sole substrate; the significance of H1 methylation remains to be determined. Methylation of H3 has been shown to occur predominantly at lysine 4 in a wide range of organisms, as well as at lysine 9 in HeLa cells, although the responsible HMTase(s) have yet to be defined (Strahl et at., 1999). To investigate the site utilisation profile of Suv39h1, unmodified peptides comprising the wild-type H3 N-terminus (aa 1–20) and a mutant K9L peptide, changing lysine 9 to leucine were tested as substrates. Additionally insulin and peptides comprising the N-termini CENP-A (Sullivan et al., 1994) and macroH2A (Pehrson and Fried, 1992) were included. Peptides were in vitro methylated by GST-Suv39h1(82–412), and reaction products were separated by high percentage SDS-PAGE and visualised by fluorography. These in vitro assays revealed selective methylation of the wild-type H3 peptide, whereas no signals were detected with the CENP-A or macroH2A peptides, or with insulin (see FIG. 3B). Importantly, the mutated H3 (K9L) peptide was not a substrate, suggesting that lysine 9 of the H3 N-terminus is a preferred residue for Suv39h1-dependent HMTase activity.

To more definitively determine this site preference, the wild-type H3 N-terminal peptide was in vitro methylated by GST-Suv39h1(82–412), using S-adenosyl-[methyl-$^3$H]-

L-methionine. The labelled peptide, purified by reverse-phase HPLC, was then directly microsequenced, and $^3$H-incorporation associated with each individual amino acid was analysed by scintillation counting. The results confirmed selective transfer of methyl-label to lysine 9 (see FIG. 3C), demonstrating that Suv39h1 is a highly site-specific HMTase for the H3 N-terminus in vitro.

EXAMPLE 5

Targeting the Suv39h1 and Suv39h2 Loci in the Mouse Germline

Figure 4A:
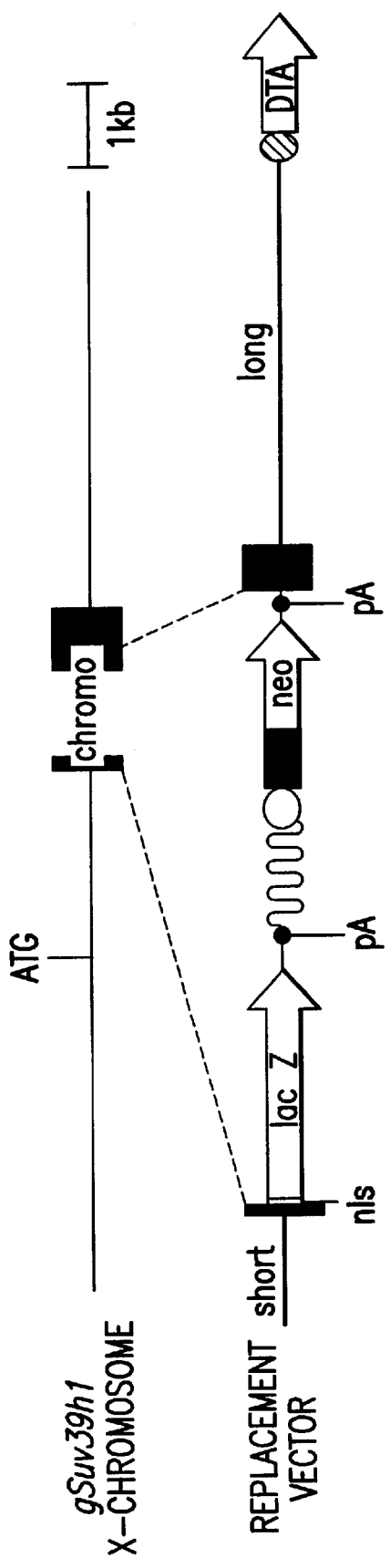
Figure 4B:
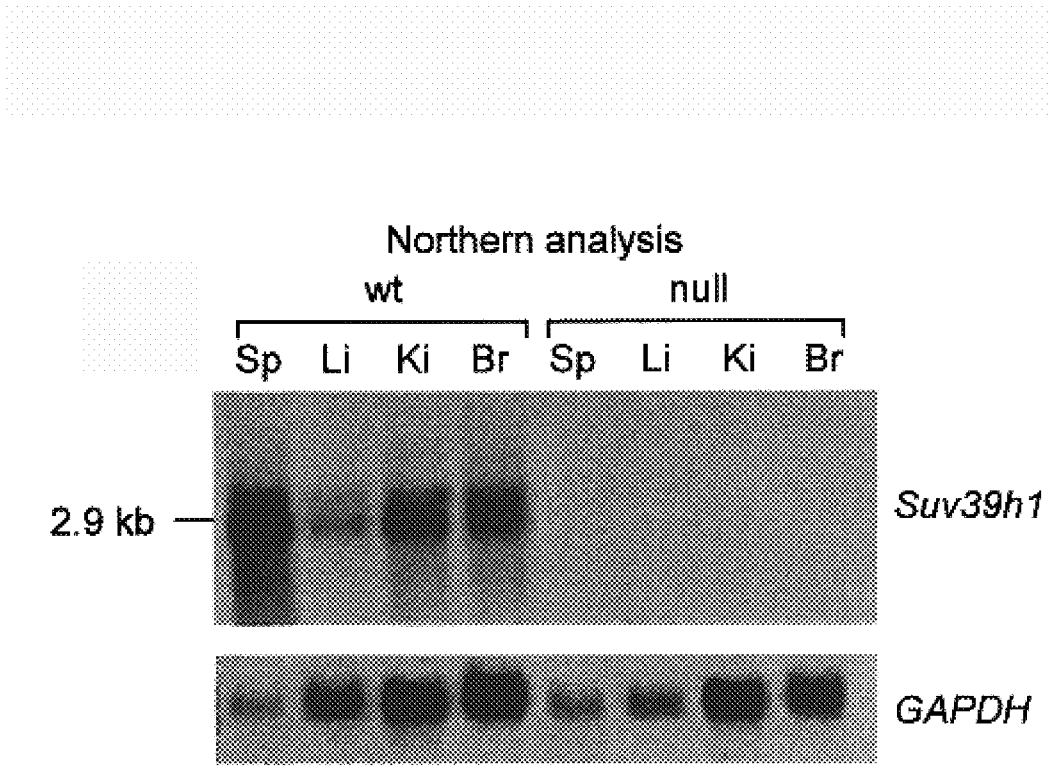
Figure 4C:
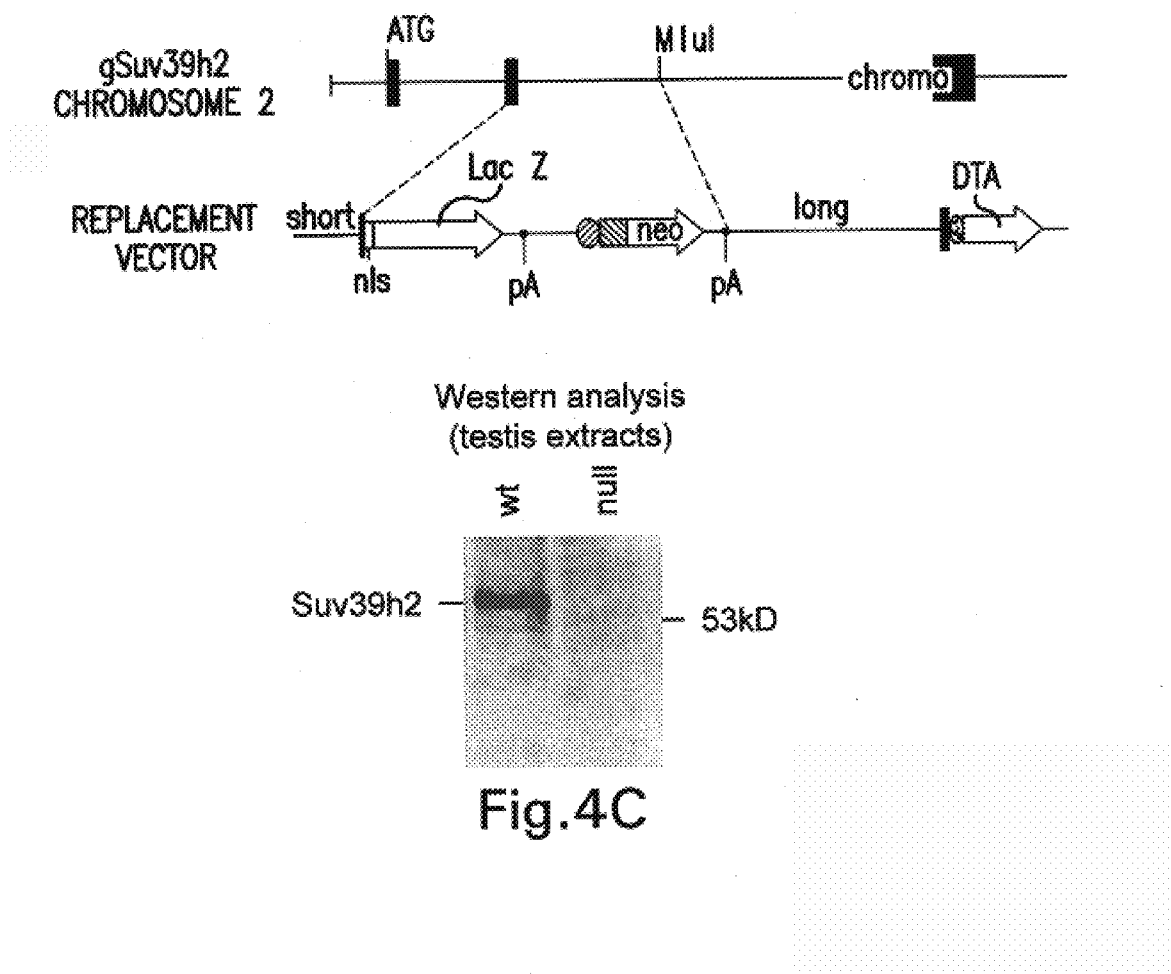

Murine Suv39h genes are encoded by 2 loci, Suv39h1 and Suv39h2 (O'Carroll et al., 2000).To investigate the in vivo significance of Suv39h function and Suv39h-dependent H3-K9 methylation, mouse strains deficient for both Suv39h1 and Suv39h2 were generated according to standard techniques. The targeting strategies are shown in FIG. 4, as well as demonstrating the production of null alleles for both Suv39h1 and Suv39h2. Mutation of either gene results in viable and fertile mice as a consequence of functional redundancy between both loci. Therefore, Suv39h1 and Suv39h2 deficient strains were intercrossed to produce Suv39h double null mice. Suv39h double null mice are born in sub-Mendelian ratios (see Example 8B, below), where only approximately 30% of the expected Suv39h double mutants are observed. FIG. 4 shows a conventional targeting strategy used to inactivate the X-linked Suv39h1 locus. FIG. 4B shows the Northern blot analysis of Suv39h1 from spleen (Sp), liver (Li), kidney (Kidney), and brain (Br) from wild-type and Suv39h1 null mice. FIG. 4C shows the conventional targeting strategy used to inactivate the autosomal Suv39h2 locus. (Bottom panel) Western blot analysis with α-Suv39h2 antibodies on protein extracts derived from wild-type and Suv39h2 null testis.

EXAMPLE 6

Aberrant Mitoses in Suv39h Double Null Primary Mouse Fibroblasts (PMEFs)

In order to determine whether the embryonic phenotypes in Suv39h double null mice can be attributed to mitotic defects, PMEFs derived from Suv39h double mice were analysed. Cell cycle profiles of wild-type and Suv39h double null PMEFs indicated rather similar percentages of cells to be in S- and G2/M-phases (see FIG. 5A), whereas Suv39h double null PMEFs display a reduced G1-index and an increased proportion of cells with aberrant nuclear morphologies, reminiscent of division defects during mitosis. For example, Suv39h double null PMEFs contain approximately two-fold elevated numbers of cells with micro- and polynuclei, and are further characterised by cell subpopulations with oversized nuclei or a weak definition of heterochromatin that appears in only a few unusually condensed foci (see FIG. 5B). Furthermore, Suv39h double null cells also show genomic instabilities and readily become aneuploid (see also Example 9, below). The severity of these aneuploidies increases with higher passage numbers (see FIG. 6). The inability of Suv39h double null cells to maintain a stable karyotype may underlie the Suv39h embryonic phenotype.

Figure 5A:
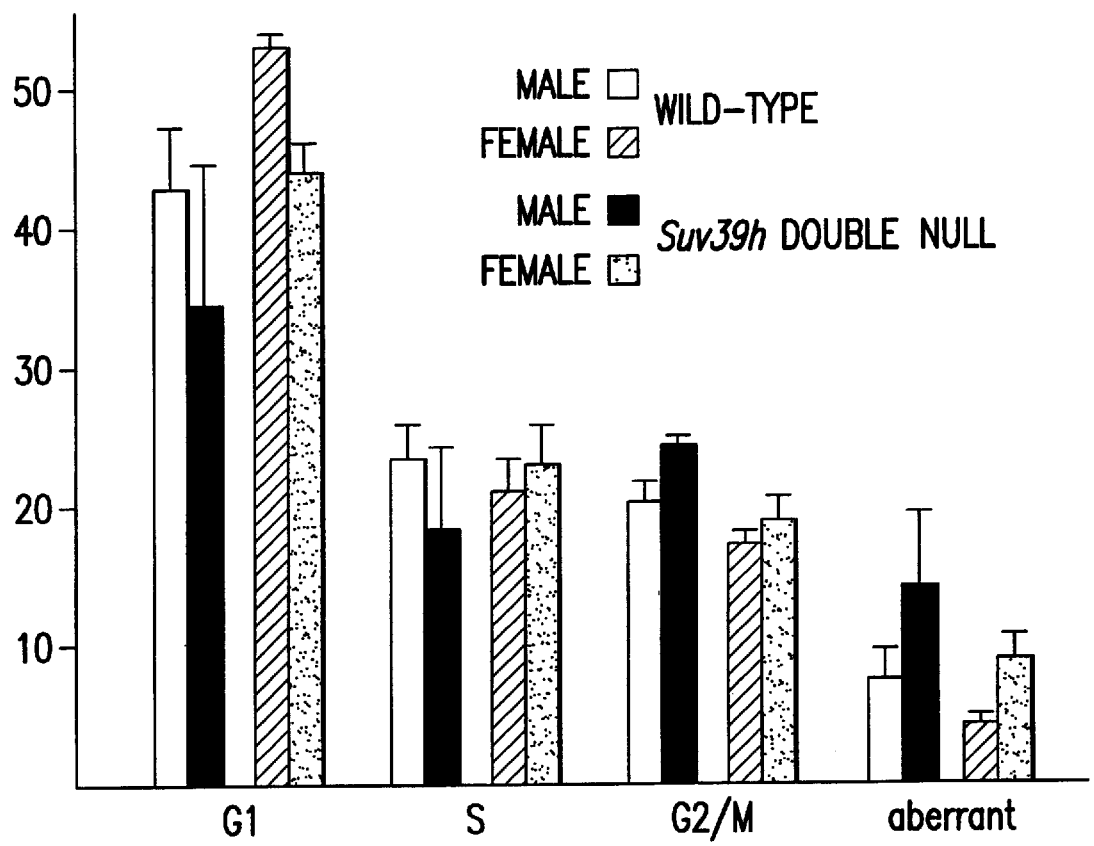

FIG. 5A shows the percentages of cells in various cell cycle stages of wild-type and Suv39h double null PMEFs.

Figure 5B:
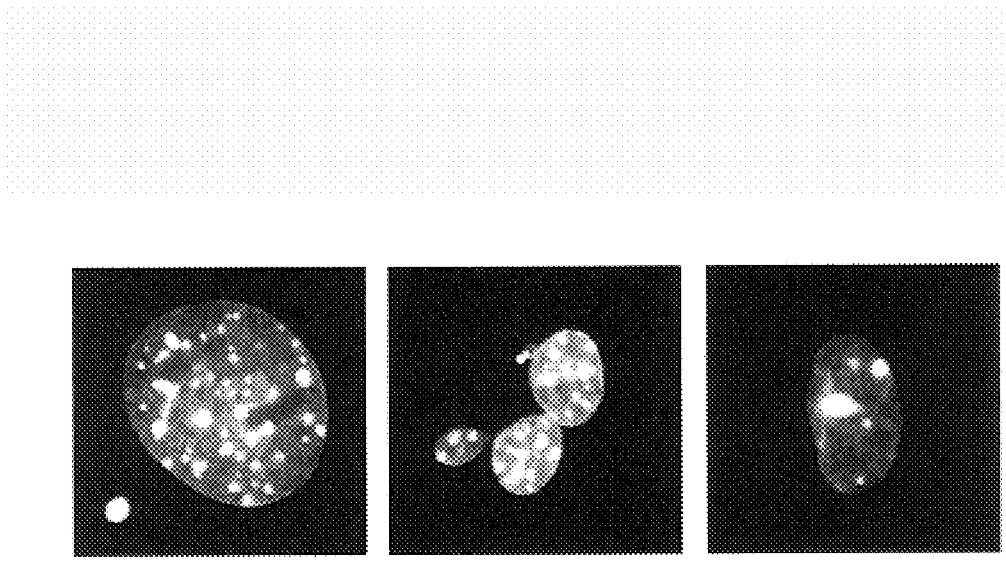

FIG. 5B shows representative images (left and middle) of aberrant mitoses in Suv39h double null PMEFs detected by α-tubulin (not shown) and DAPI staining. Also shown (right image) is a nucleus exemplifying the unusual definition of heterochromatin in a subpopulation of Suv39h double null PMEFs. All images were taken at a magnification of 630×.

Figure 6A:
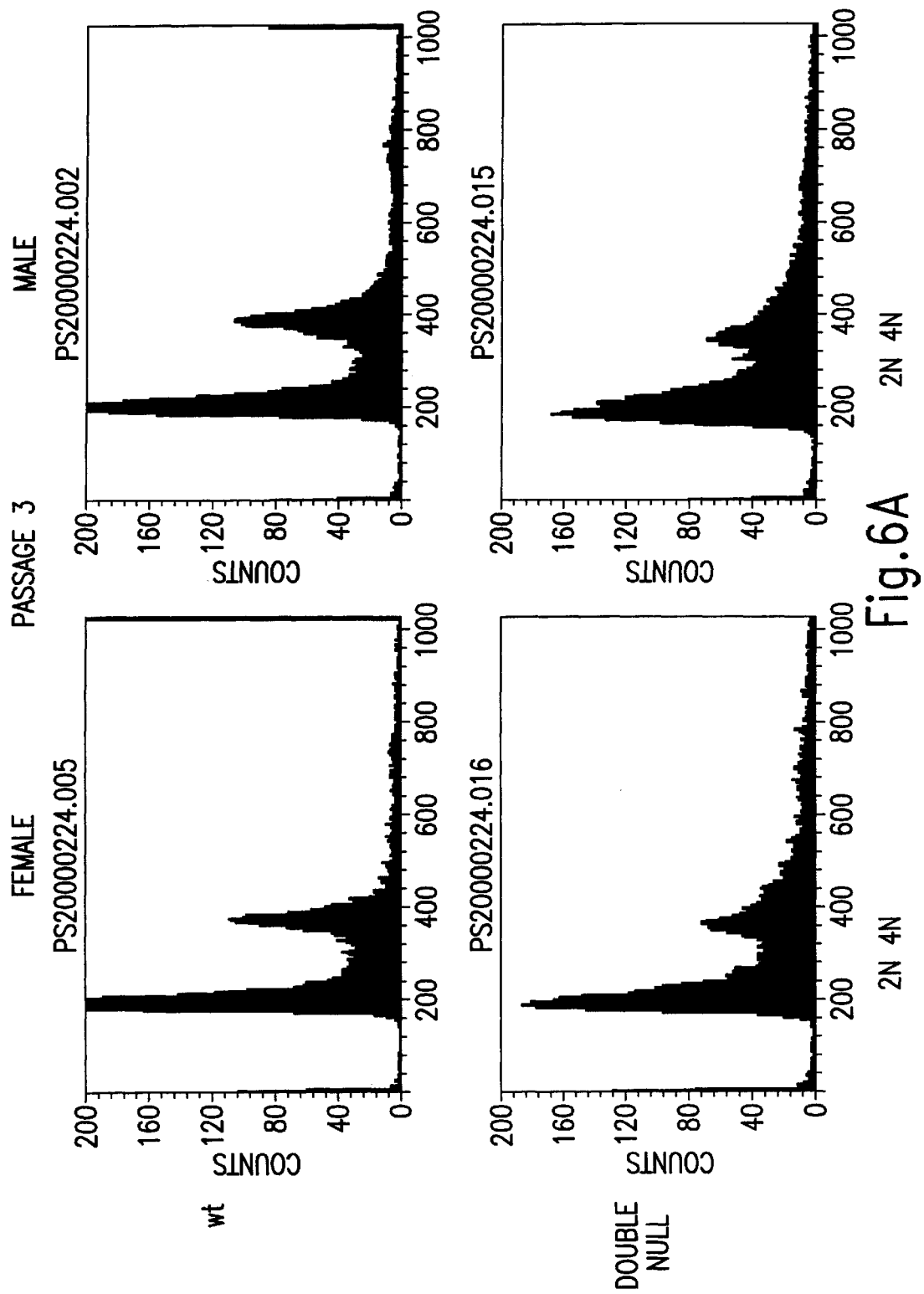
Figure 6B:
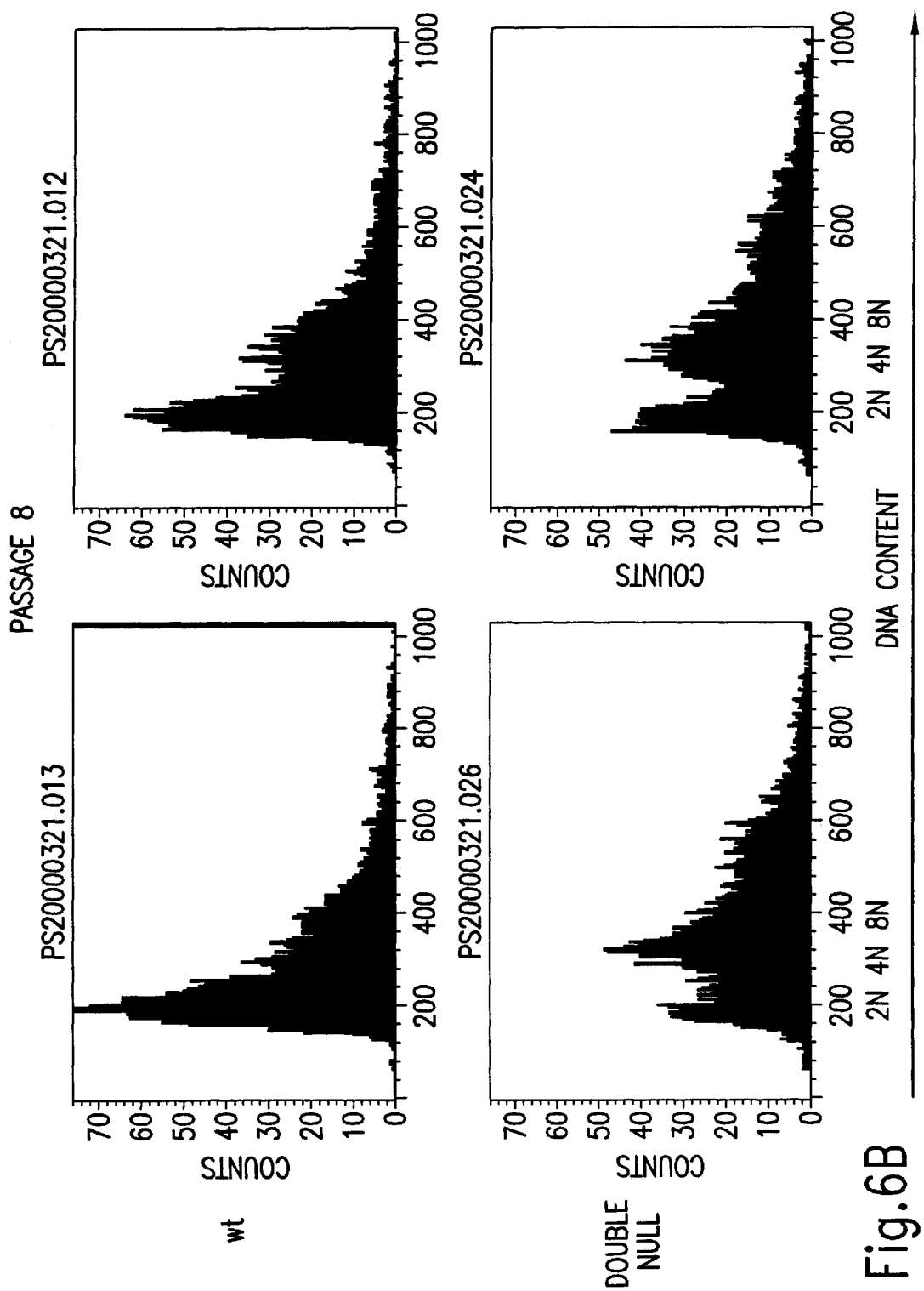

FIG. 6A shows the DNA content profile of wild-type and Suv39h double null PMEFs at passage 3. FIG. 6B shows the DNA content profile of wild-type and Suv39h double null PMEFs at passage 8.

EXAMPLE 7

Increased phosH3 Phosphorylation in Suv39h Double Null PMEFs

Phosphorylation at serine 10 (phosH3) in the N-terminal tail of H3 has been shown to be required for condensation and subsequent segregation of chromosomes (Wei et al., 1999). During the cell cycle, phosH3 initiates within pericentric heterochromatin in late G2 and then progresses along the entire chromosomes during mitosis (Hendzel et al., 1997). In wild-type PMEFs, approximately 7% of the cells stain positive for the characteristic, heterochromatin-associated phosH3 foci, as detected by indirect immunofluorescence with α-phosH3 antibodies (see FIG. 7A, right panel). In contrast, this number is increased by a factor of about 3-fold in Suv39h double null PMEFs, with approximately 22% of the cells containing phosH3-positive foci (FIG. 7A, left panel), although their definition appears in many small speckles which do not always overlap with DAPI-dense material. This result suggested that the overall levels of phosH3 may be enhanced in Suv39h double null PMEFs. Therefore, the relative abundance of phosH3 in precalibrated nuclear extracts was determined with α-phosH3-specific antibodies. This quantitation indicated a significantly higher level of phosH3 in Suv39h double null cells as compared to wild-type controls (see FIG. 7B). Together, the obtained data are most consistent with a model in which Suv39h-mediated methylation of lysine 9 in H3 negatively regulates phosphorylation of serine 10.

Figure 7A:
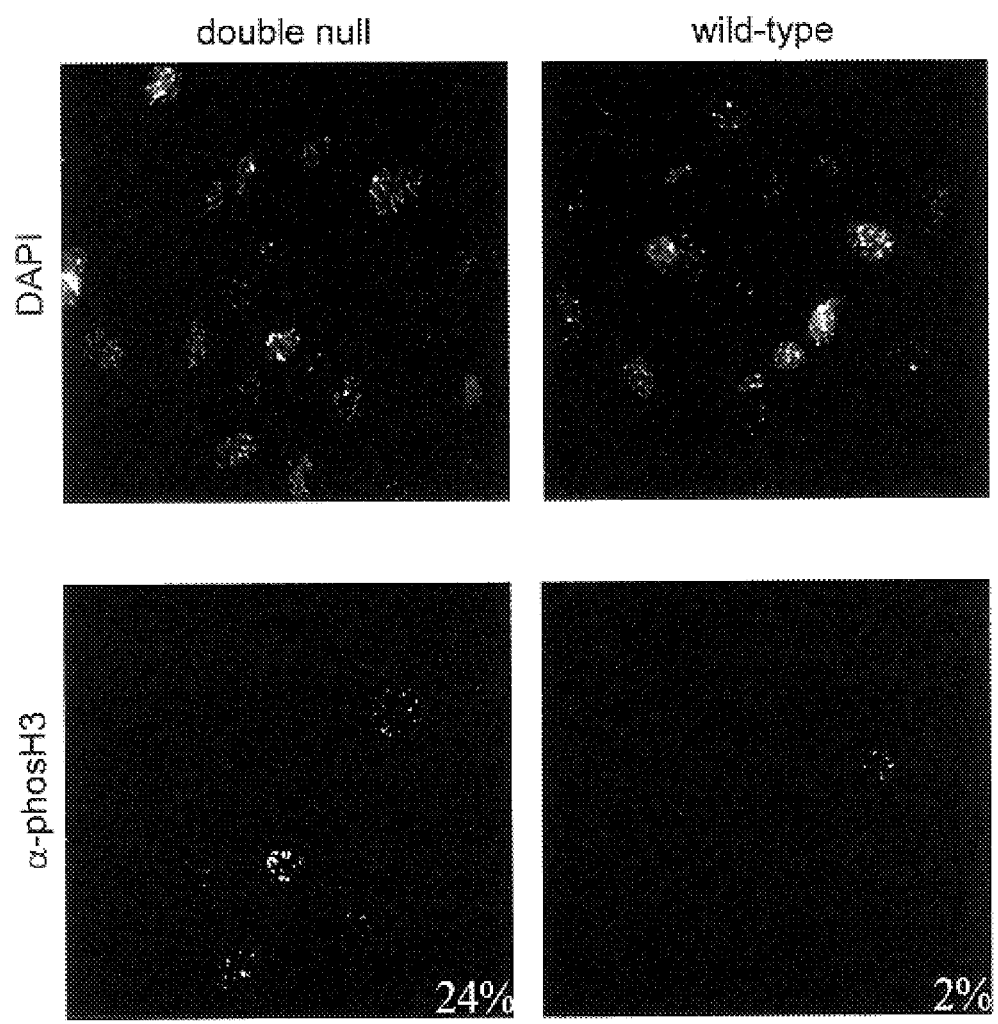
Figure 7B:
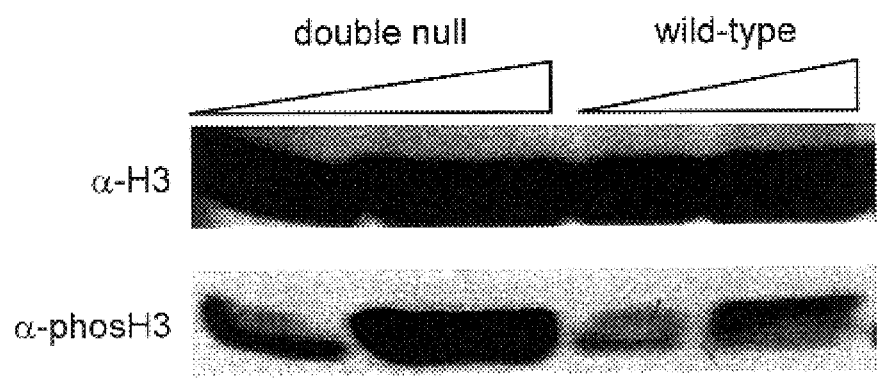
Figure 8:
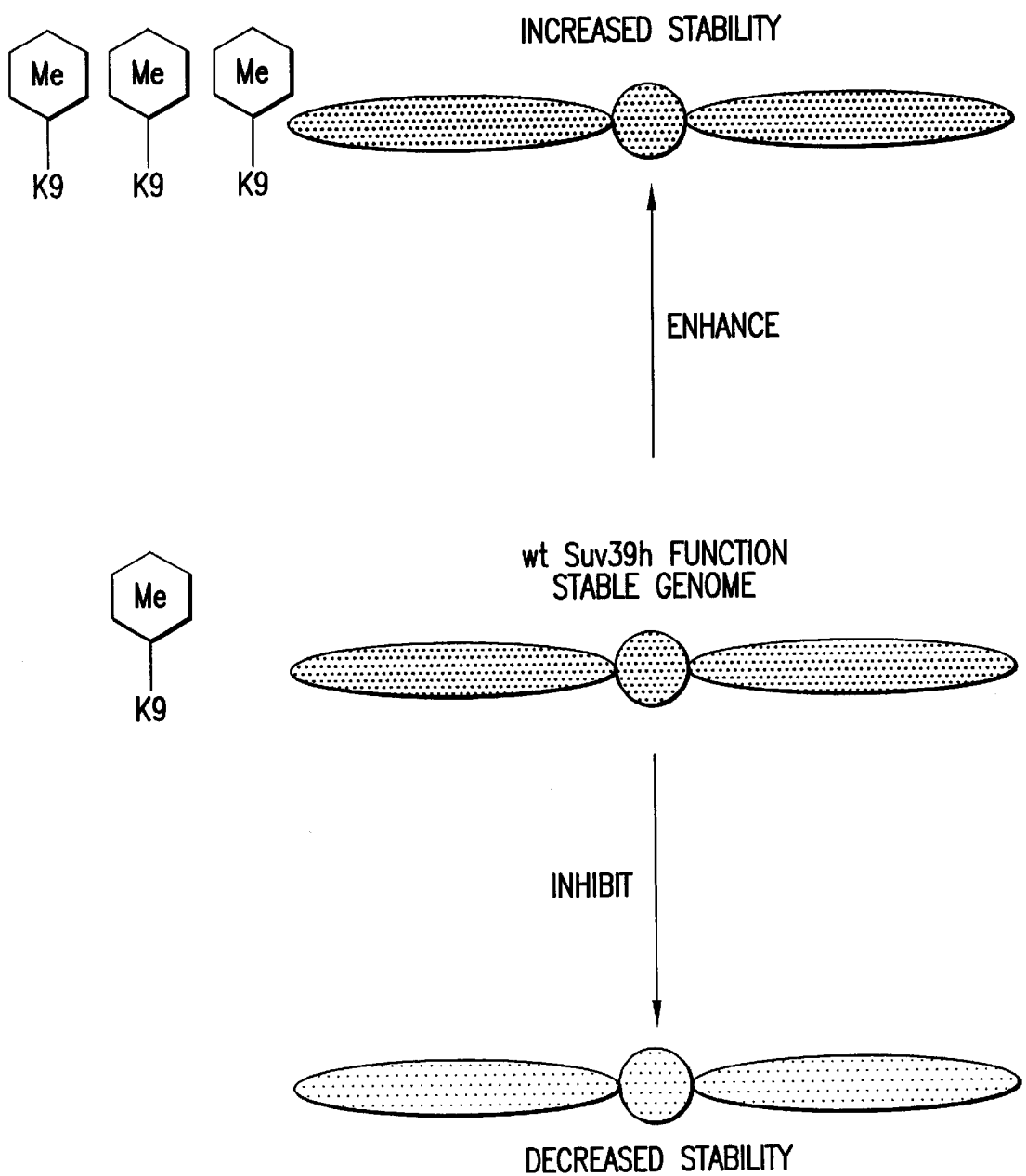

FIG. 7A shows an interphase chromatin staining with α-phosH3 antibodies and CY3 conjugated secondary antibodies. DNA was counterstained with DAPI. At least 1,000 cells were counted to evaluate the percentage (indicated in the Figure) of α-phosH3 positive cells. FIG. 7B shows a quantitative Western analysis with 15 μg and 30 μg of total nuclear proteins immuno-blotted with α-H3 and α-phosH3 antibodies.

EXAMPLE 8 a) Generation of Suv39h double deficient mice

Figure 1A:
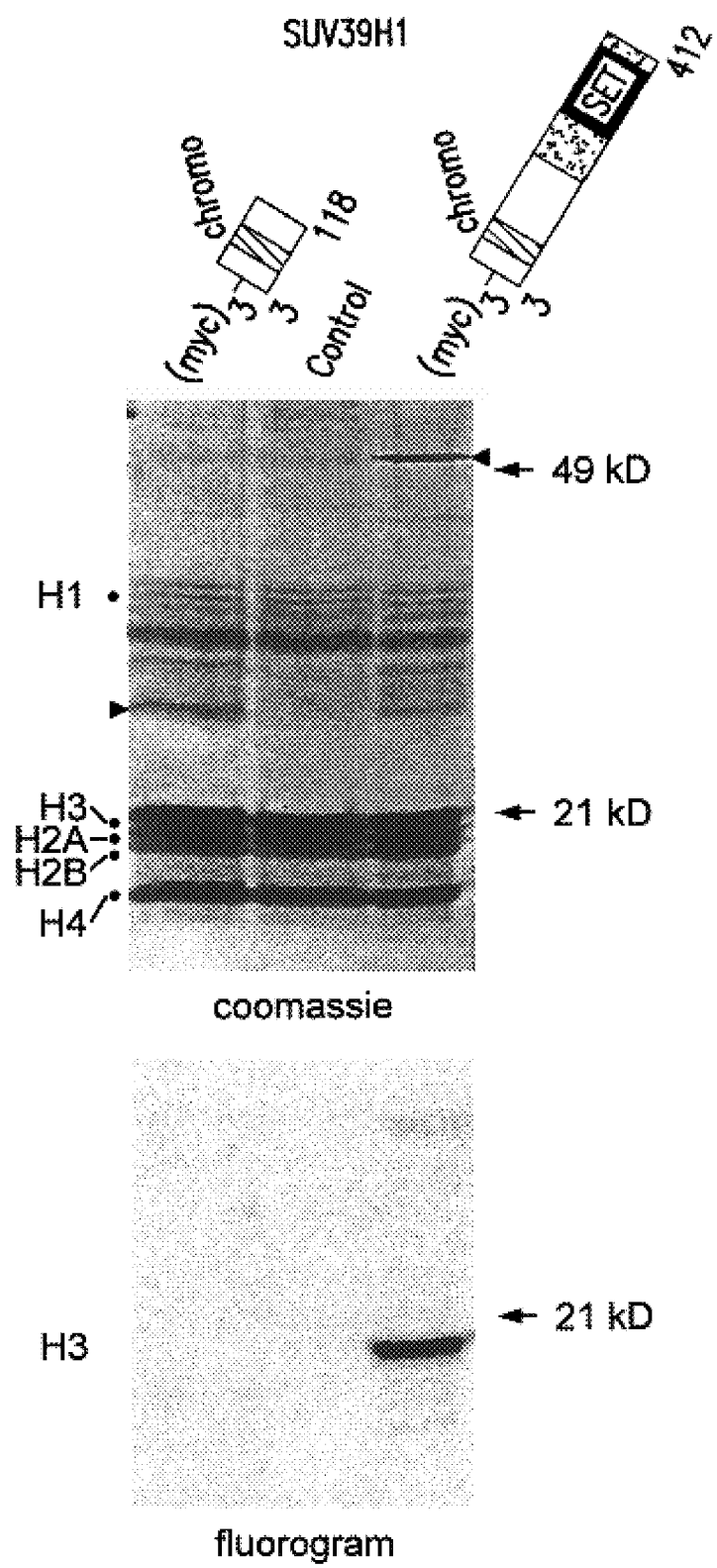
Figure 1B:
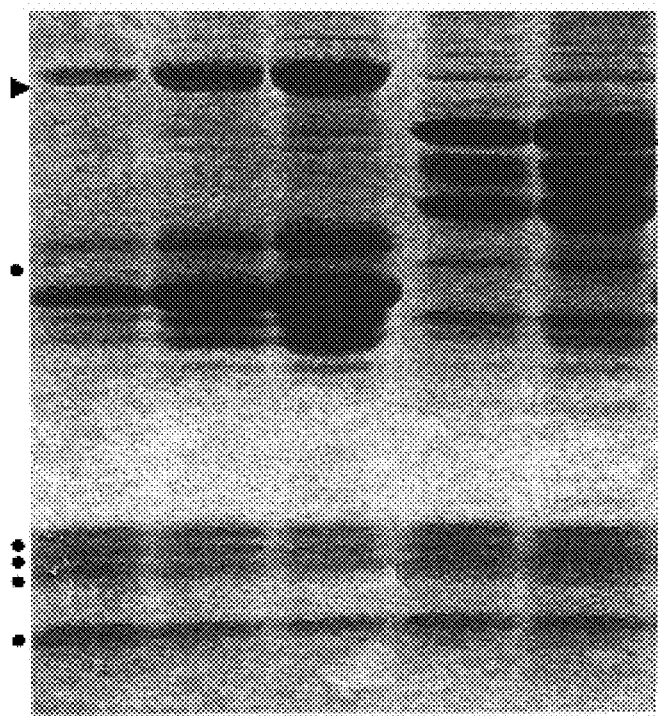
Figure 2A:
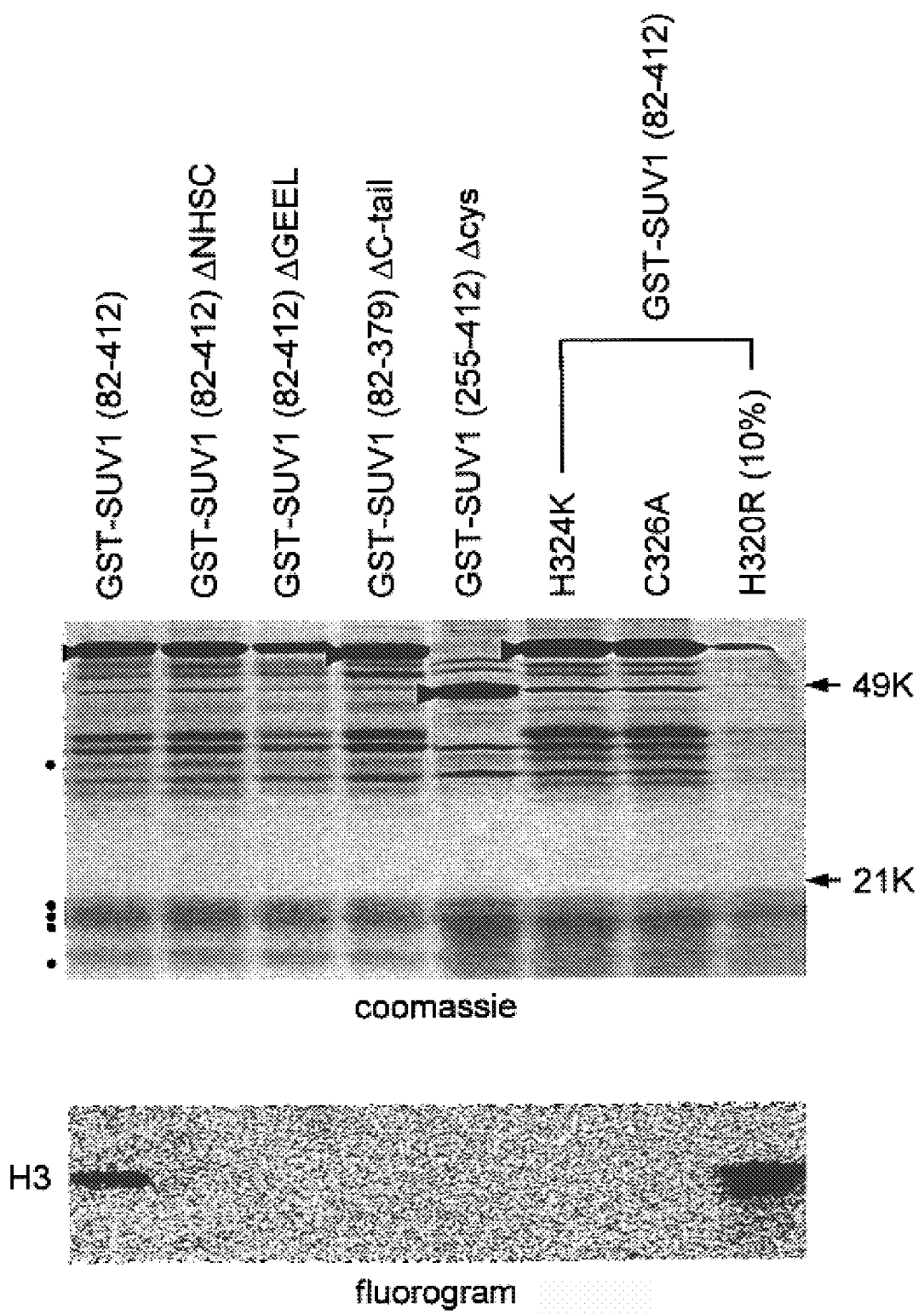
Figure 2B:
Figure 2C:
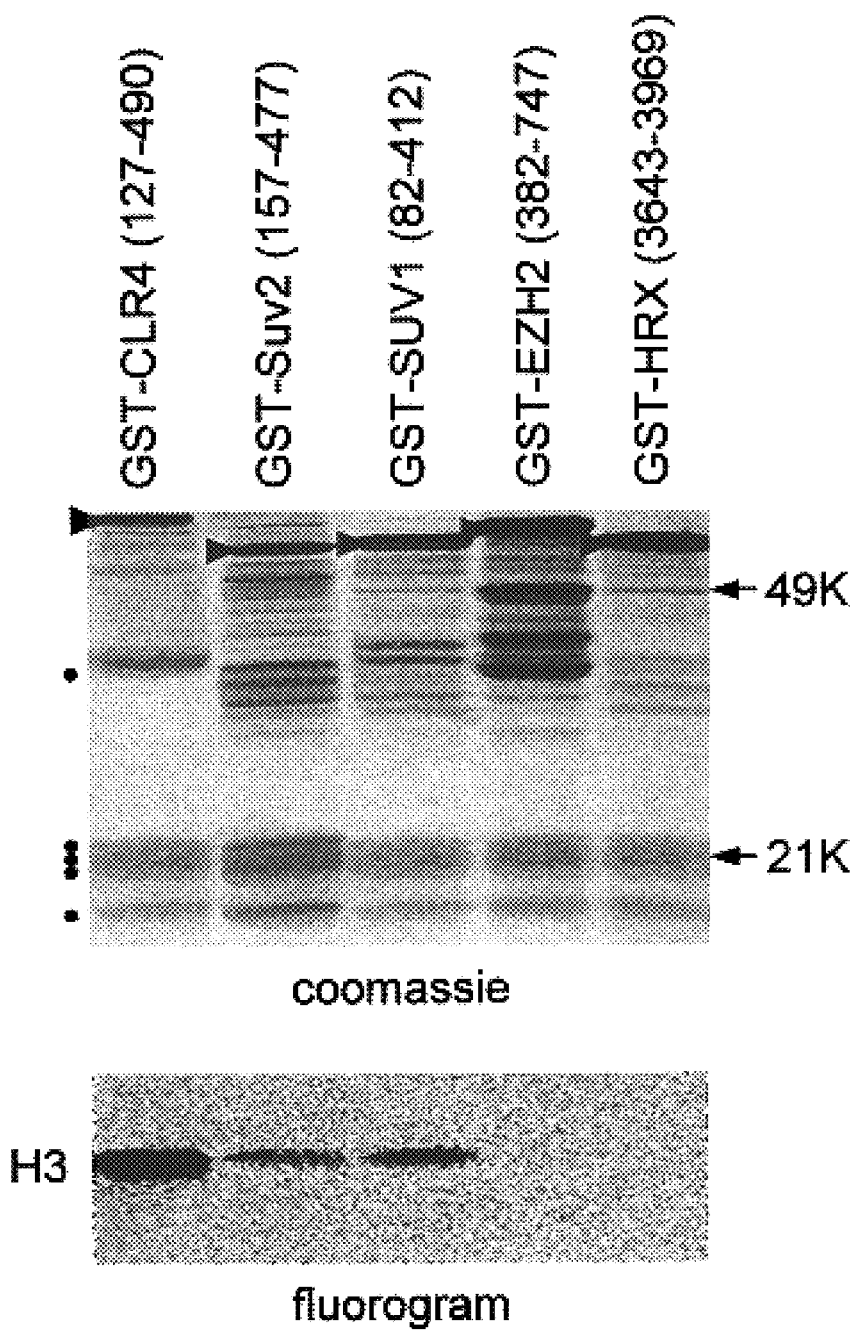
Figure 3A:
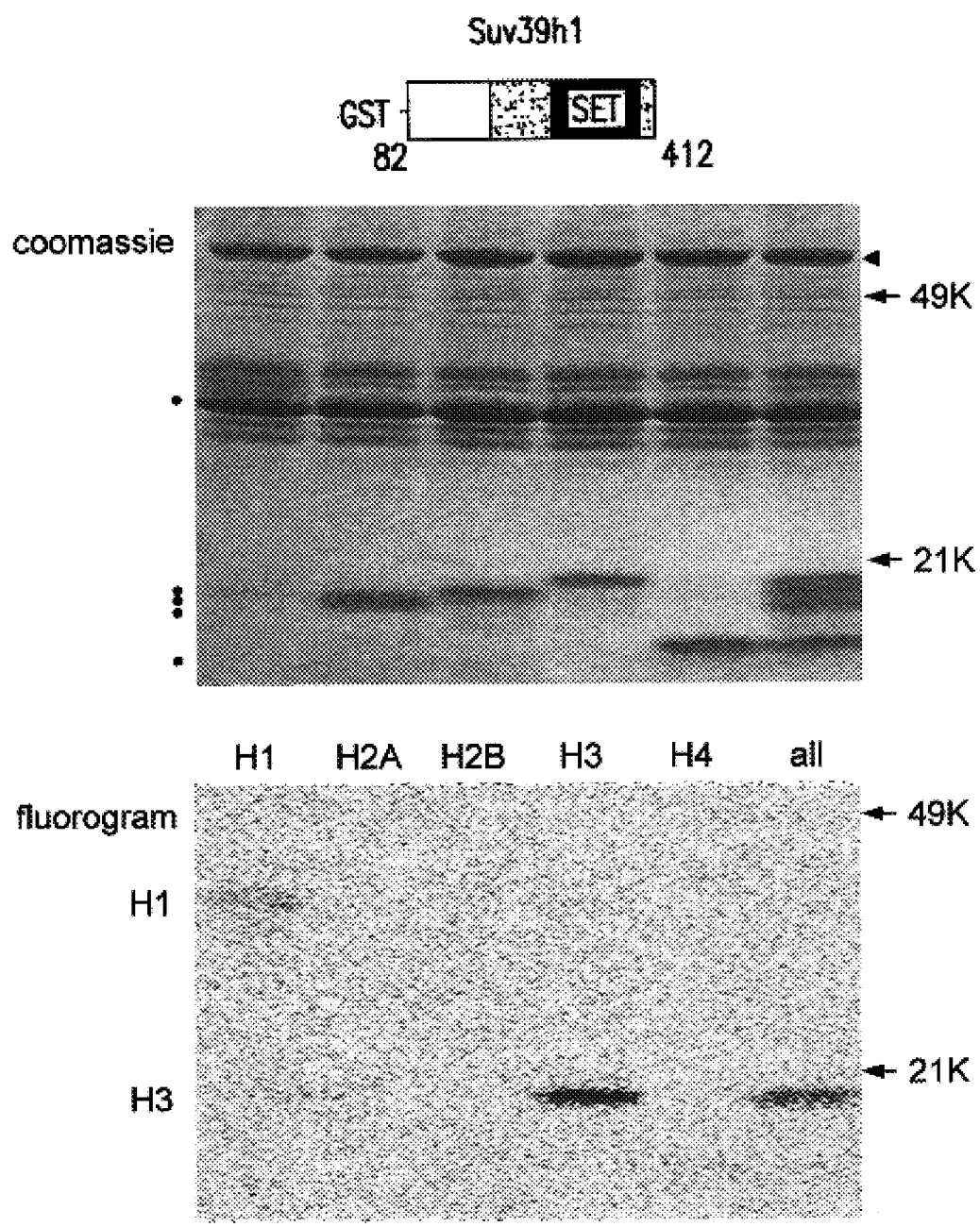
FIG. 3B shows the results of in vitro methylation assays using GST-Suv39h1(82–412) as enzyme and the indicated N-terminal peptides of wild-type H3, mutated H3 (K9L), CENP-A, macroH2A or insulin as substrates.
FIG. 3C shows the result of automated sequencing of the wild-type H3 N-terminal peptide (aa 1–20) that had been methylated in vitro by recombinant GST-Suv39h1(82–412). Displayed is the $^3$H-incorporation of individual amino acids identified at each successive round of microsequencing.
Figure 3B:
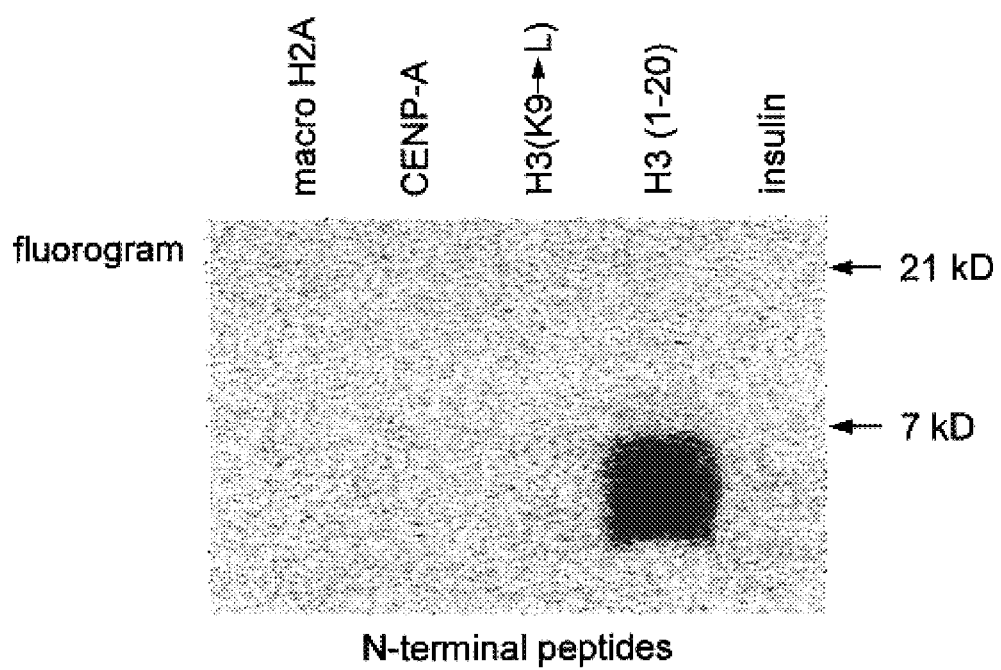
Figure 3C:
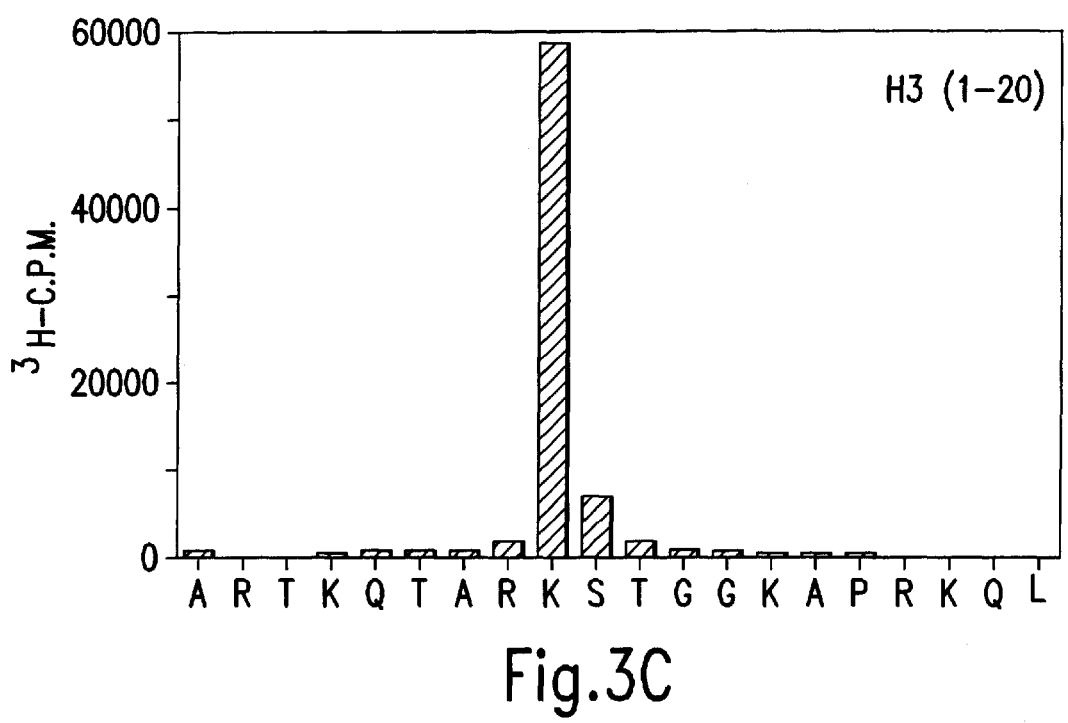
Figure 9B:
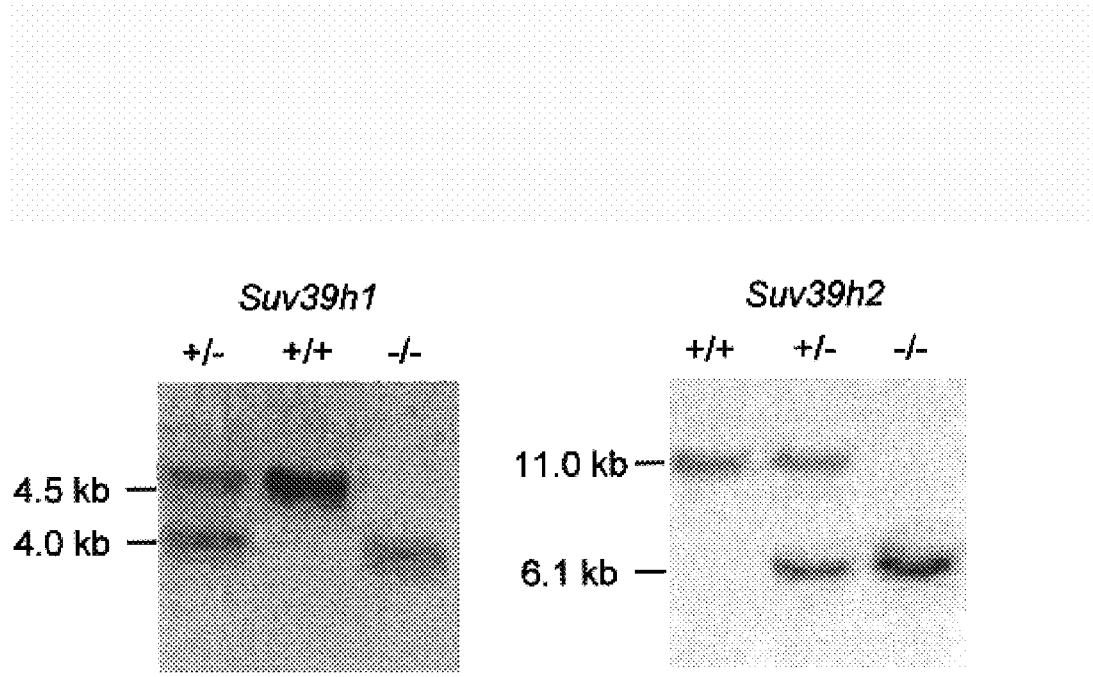
Figure 9C:
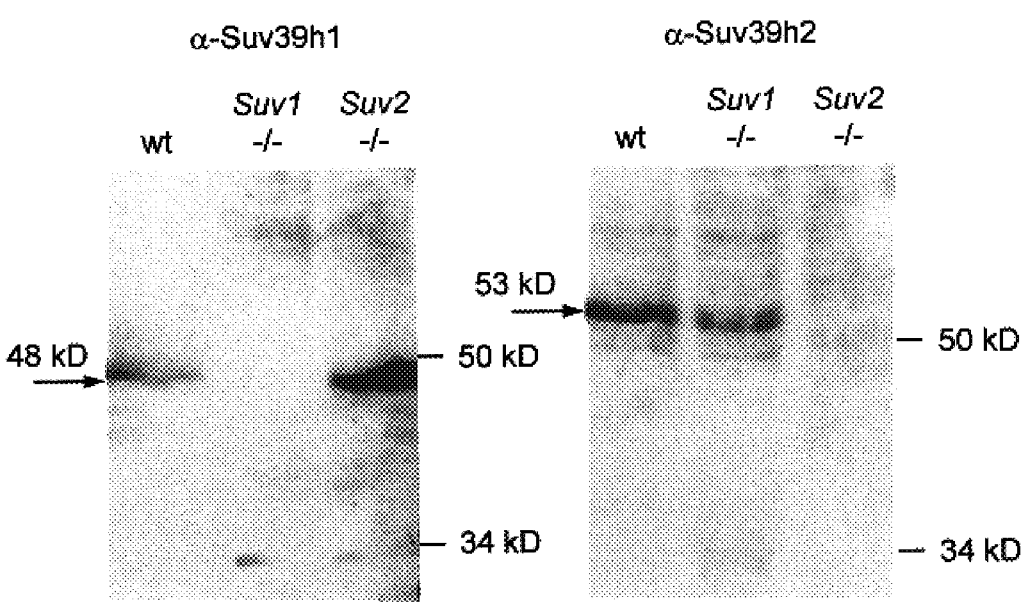

Murine Suv39h HMTases are encoded by two loci which have been mapped to centromere-proximal positions in the X chromosome (Suv39h1) or in chromosome 2 (Suv39h2) (O'Carroll et al., 2000). Both gene loci were independently disrupted by homologous recombination in embryonic stem (ES) cells using a conventional targeting approach that replaces parts of the evolutionarily conserved chromo domain with the bacterial LacZ gene and all RSV-neomycin selecion cassette (FIGS. 9A1,A2). These targeting strategies produce in-flame fusion proteins of the first 40 amino acids of Suv39h1 or of the first 113 amino acids of Suv39h2 with lacZ, which maintain β-galactosidase activities. Successfully targeted ES cell clones were used to generate chimaeric mice that transmitted the mutated Suv39h1 or Suv39h2 alleles through the germ line (FIG. 9B). Protein blot analyses of testis nuclear extracts from wild-type, Suv39h1- and Suv39h2- deficient mice with α-Suv39h1 and α-Suv39h2 specific antibodies (Aagaard et at., 1999; O'Carroll et al., 2000) indicated the absence of the respective proteins, demonstrating that had been generated loss-of-function alleles for both genes (FIG. 9C).

b) Impaired viability of Suv39h double null mice

Figure 9D:
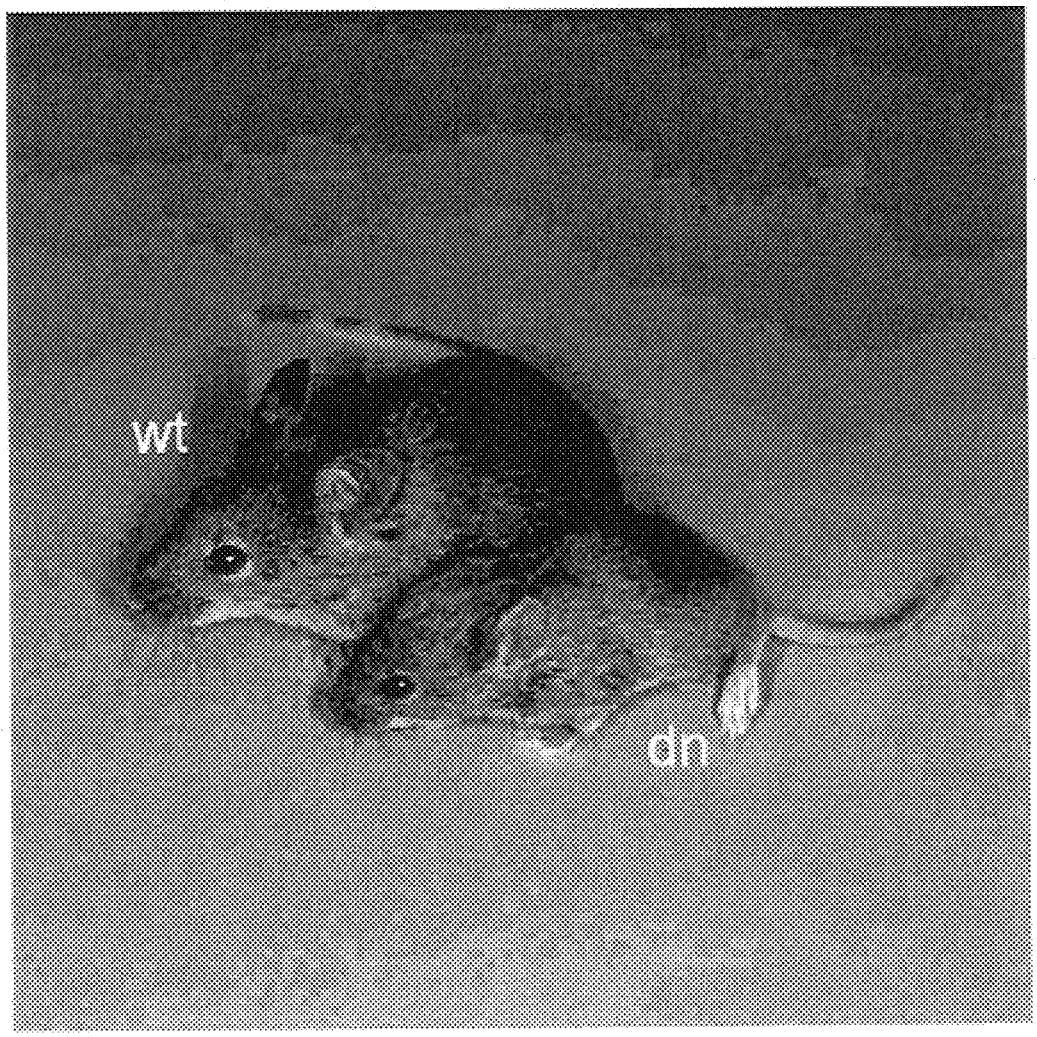

Mice deficient for either Suv39h1 or Suv39h2 display normal viability and fertility, and do not exhibit apparent phenotypes, suggesting that both genes may be functionally redundant during mouse development (O'Carroll et al., 2000). Therefore, Suv39h1-/- and Suv39h2-/- mice were intercrossed to generate compound Suv39h mutants that were then used to derive Suv39h double null (dn) mice. Suv39h dn mice obtained from several different intercrosses (Table I) are born at only sub-Mendelian ratios, are growth retarded (FIG. 9D) and are characterized by hypogonadism in males. For example, from a total of 197 mice, 46 mice would have been expected to be double null (Table I), but only 15 Suv39h dn mice (≈33%) were born. Analysis of mouse embryogenesis indicated normal development of Suv39h dn fetuses until day E12.5, whereas at later stages, Suv39h dn fetuses are smaller and display an increased rate of resorptions and prenatal lethality. Together, these results demonstrate that the Suv39h genes are required for normal viability, and for pre- and postnatal development.

FIG. 9 shows the targeting and genotyping of Suv39h1- and Suv39h2-deficient mice as follows: (A) Diagrammatic representation of the Suv39h1 and Suv39h2 genomic loci, the replacement vectors and the targeted alleles. Exons are indicated by black boxes with numbers referring to the starting amino acid positions of the respective exons (O'Carroll et al., 2000). Also shown are the diagnostic restriction sites and the external probes used for Southern blot analyses. pA indicates polyadenylation signals. (B) Southern blot analyses of PvuII- or HindIII-digested DNA isolated from offspring of Suv39h1+/– or Suv39h2+/– heterozygous intercrosses. (C) Protein blot analyses of testis nuclear extracts from wild-type (wt), Suv39h1-/- (Suv1-/-) and Suv39h2-/- (Suv2-/-) mice with α-Suv39h1 and α-Suv39h2 antibodies. The size of the Suv39h1 or Suv39h2 proteins is indicated by arrows. (D) Suv39h double null (dn) mice are growth retarded at birth and during adulthood.

EXAMPLE 9

Chromosome Mis-segregation in Suv39h dn Embryonic Fibroblasts

Figure 10A:
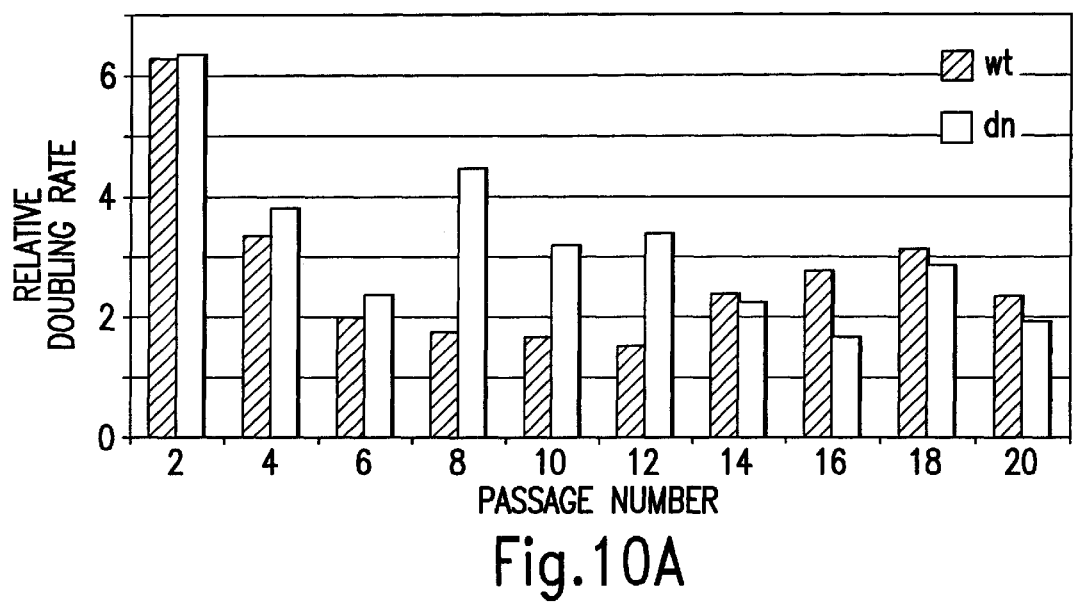
Figure 10B:
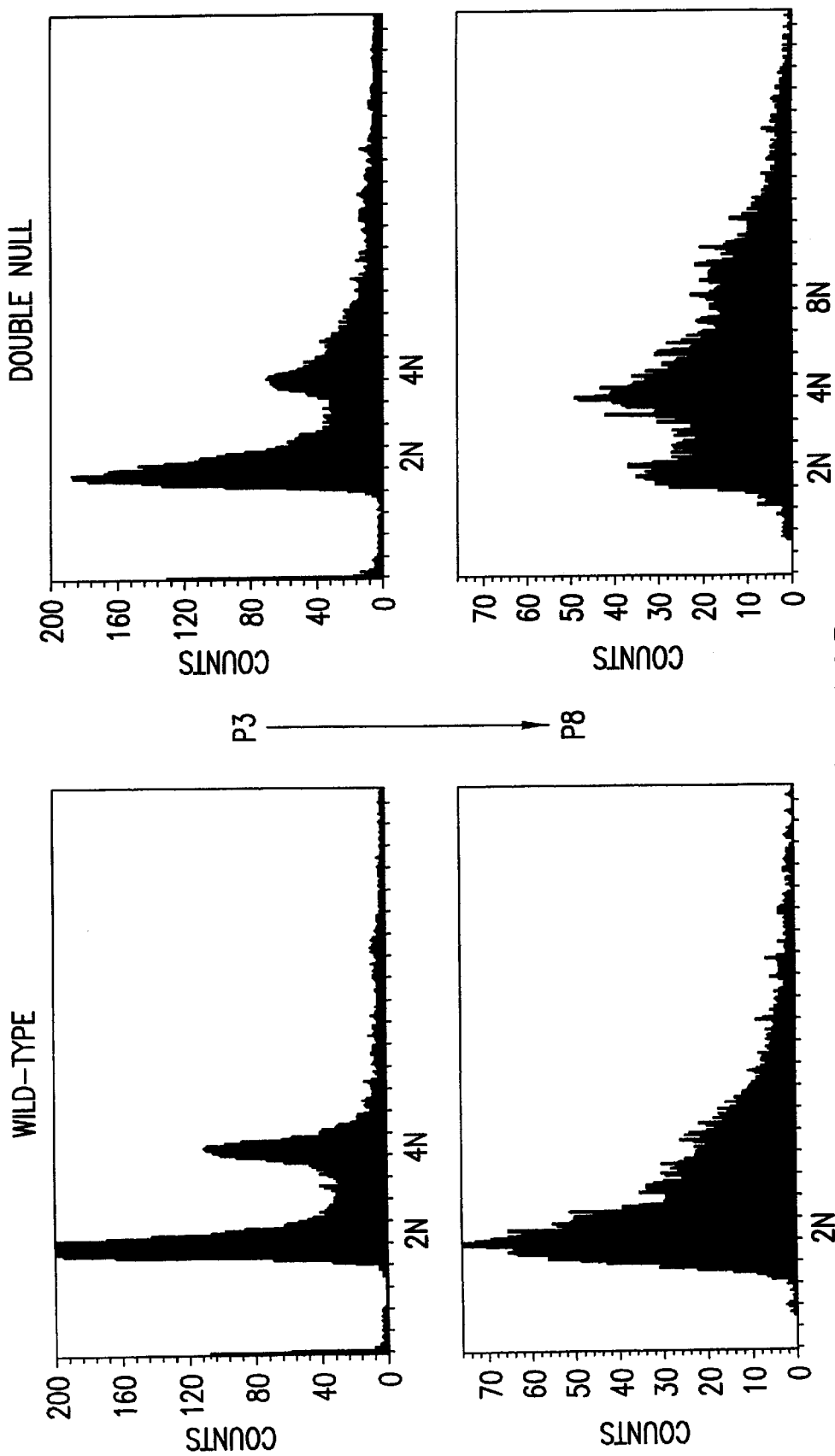

To examine the Suv39h-dependent defects in more detail, primary mouse embryonic fibroblasts (PMEFs) were derived from day E12.5 fetuses. Comparative growth curves between wild-type (wt) and Suv39h dn PMEFs in a 3T3 protocol over the first 20 passages indicated that Suv39h dn PMEFs displayed a higher doubling rate until passage 12 (FIG. 10A). At later passages, the Suv39 h dn PMEFs appear to have a slightly reduced proliferative potential than the immortalised wt PMEFs which survived the characteristic Hayflick crisis. It was shown recently (see Example 6) that Suv39h dn PMEFs contain a significant fraction of cells with aberrant nuclear morphologies, such as macro- and polynuclei, which are reminiscent of impaired mitosis and chromosome mis-segregation (Rea et al., 2000). Therefore the DNA content of passage 3 and passage 8 wt and Suv39h dn PMFFs was analyzed by FACS. Whereas wt PMEFs appear genomically stable at passage 3, Suv39h dn PMEFs already contain cells with a greater than 4N DNA content, as indicated by the aneuploid shoulder in the FACS profile (FIG. 10B, top panels). At passage 8, wt PMEFs are largely senesced. By contrast, Suv39h dn PMEFs continue to proliferate, although many cells display octaploid DNA contents (FIG. 10B, lower panels).

Figure 10C:
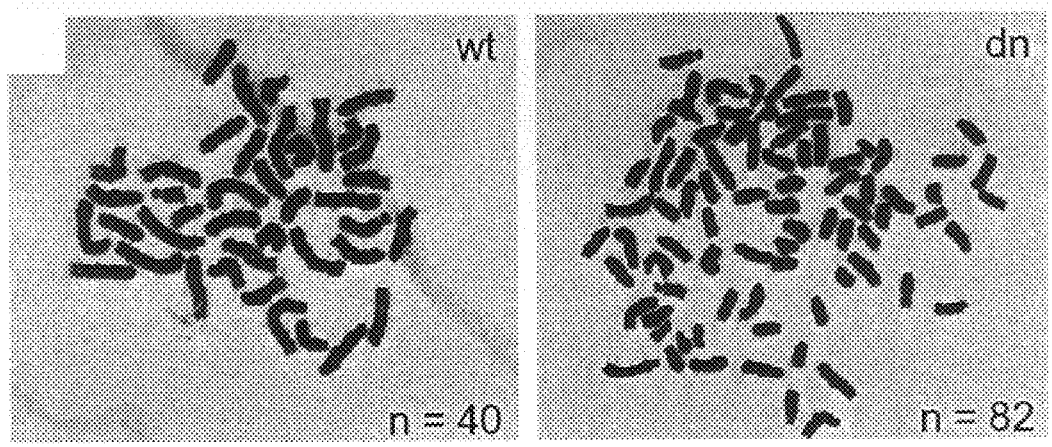
Figure 10D:
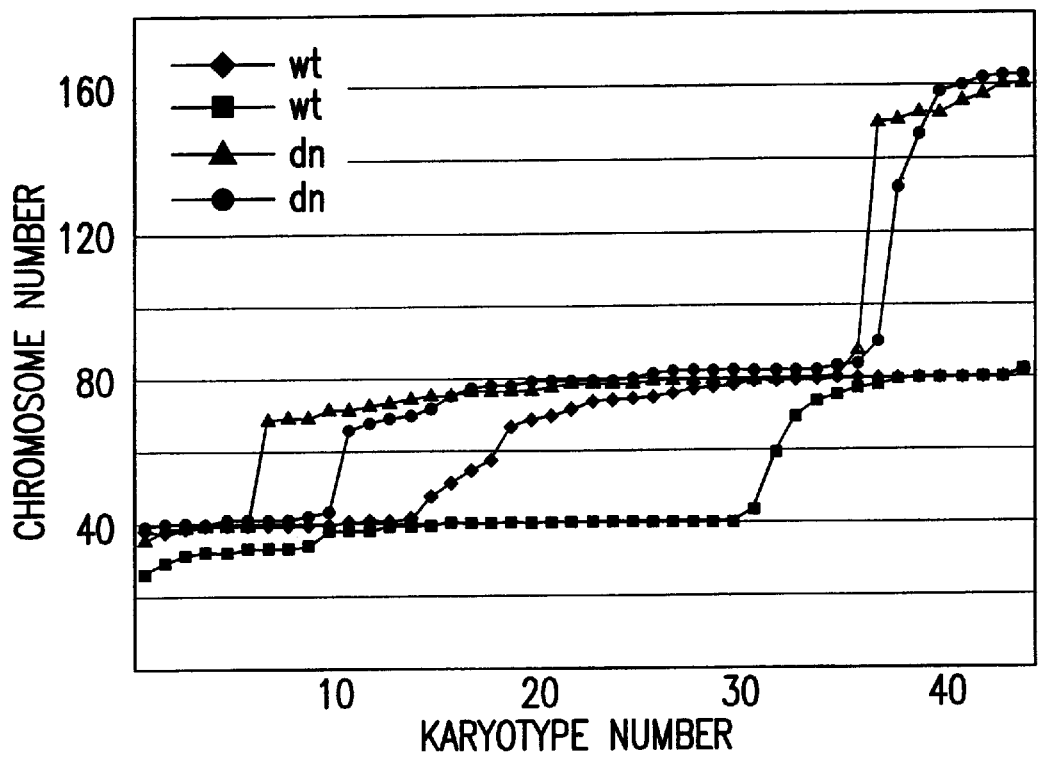

To further characterize these genomic instabilities, karyotype analyses with passage 8 PMEFs were performed (FIG. 10C). In particular, 45 karyotypes each for two independent wt and two Suv39h dn PMEF cultures were examined. As shown in FIG. 10D, a major fraction of the wt karyotypes are non-diploid, with chromosome numbers ranging from 25 to 82. Aneuploidies were significantly increased in Suv39h dn karyoptypes and comprised chromosome numbers from 38 to 162. Notably, whereas wt PMEFs contain a random array of aneuploid karyotypes, Suv39h dn PMEFs are largely hypo-tetraploid or hypo-octaploid. Chromosomes in Suv39h dn PMEFs appear of normal morphology and Robertsonian fusions were not observed. It was concluded that the absence of Suv39h function induces genomic instabilities, primarily by impairing segregation of the entire set of chromosomes.

FIG. 10 shows the chromosomal instabilities in Suv39h dn PMEFs as follows: (A) Relative doubling rates of wt and Suv39h dn PMEFs determined in a 3T3 protocl over the first 20 passages. (B) DNA contents of wt and Suv39h dn PMEF mass cultures at passage 3 and passage 8. (C) Metaphase spreads showing a diploid number (n=40) of chromosomes for wt and a hyper-tretraploid number (n=82) of chromosomes for Suv39h dn PMEFs. (D) Statistical karyotype analysis with two wt and two Suv39h dn PMEF cultures at passage 8. For each culture, 45 metaphases were evaluated.

EXAMPLE 10

Development of B-cell Lymphomas in Suv39h Mutant Mice

Figure 11A:
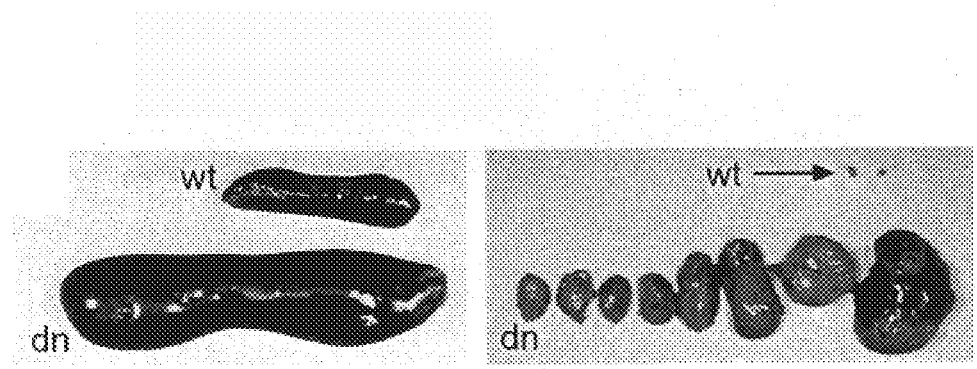

Next, Suv39h mutant mice were analyzed for the incidence of tumorigenesis. Because the majority of Suv39h dn mice are non-viable, distinct Suv39h genotypes that differ in their gene dosage for either Suv39h1 or Suv39h2 were examined. For example, it was expected that random X-inactivation of the X-linked Suv39h1 gene could increase the tumor risk in Suv39h1+/– mice, even in the presence of a functional copy of Suv39h2 which is significantly down-regulated in most adult tissues (O'Carroll et al., 2000). Indeed, examination of 98 mice which are either heterozygous (het) or null for the Suv39h1 locus indicated an ≈28% penetrance of tumor formation with an onset between 9–15 months of age (Table II). These tumors are predominantly B-cell lymphomas (FIG. 11A) that resemble by FACS profiling (see Materials and Methods) slowly progressing non-Hodgin lymphomas in humans (Foon and Gale, 1995). The tumor incidence for late onset B-cell lymphomas was ≈33% in the few viable Suv39h dn mice (n=6). By contrast, Suv39h2+/– or Suv39h2–/– mice developed B-cell lymphomas at only ≧5% penetrance (n=21), and tumor formation in control wild-type mice was not observed.

Figure 11B:
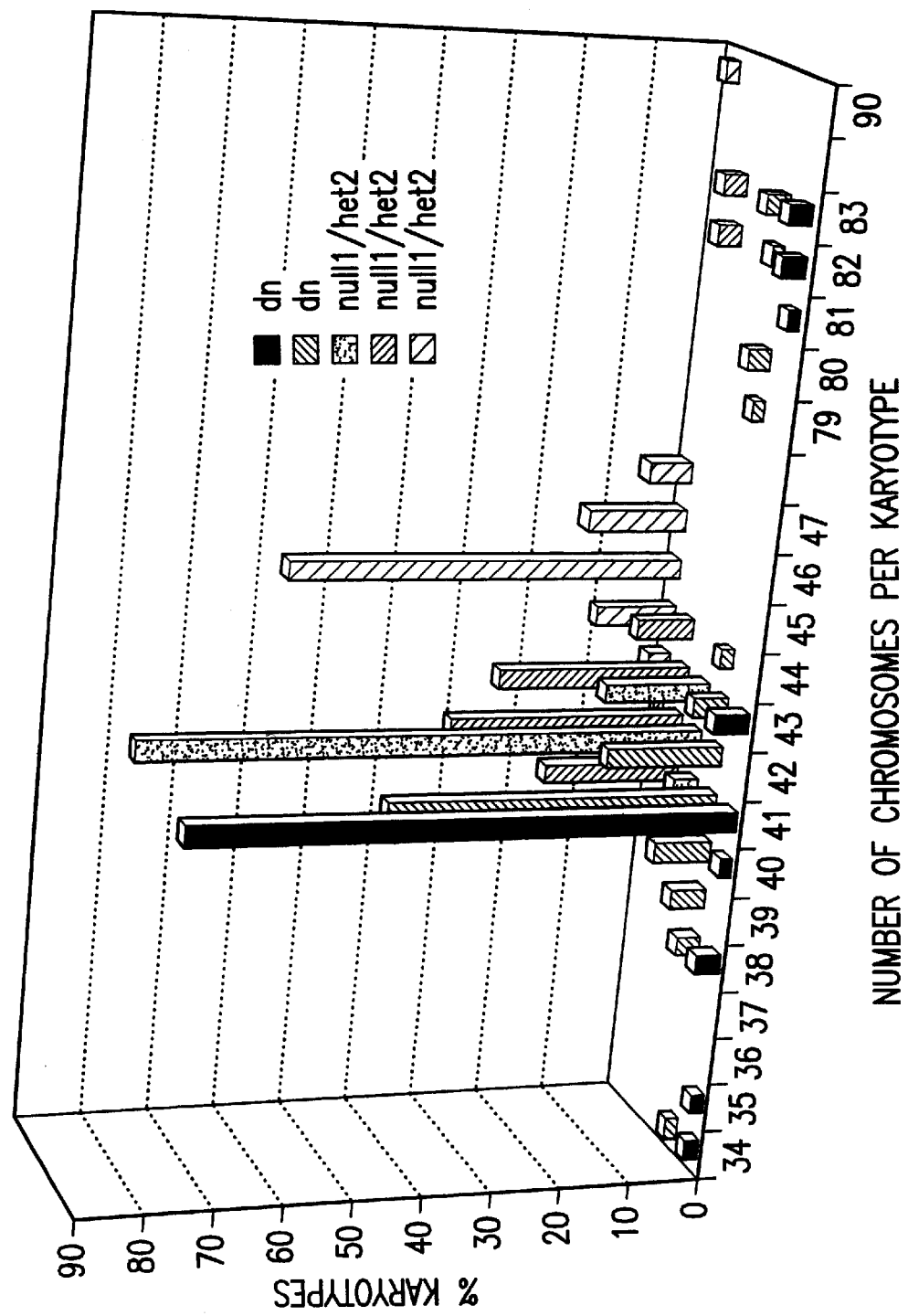
Figure 11C:
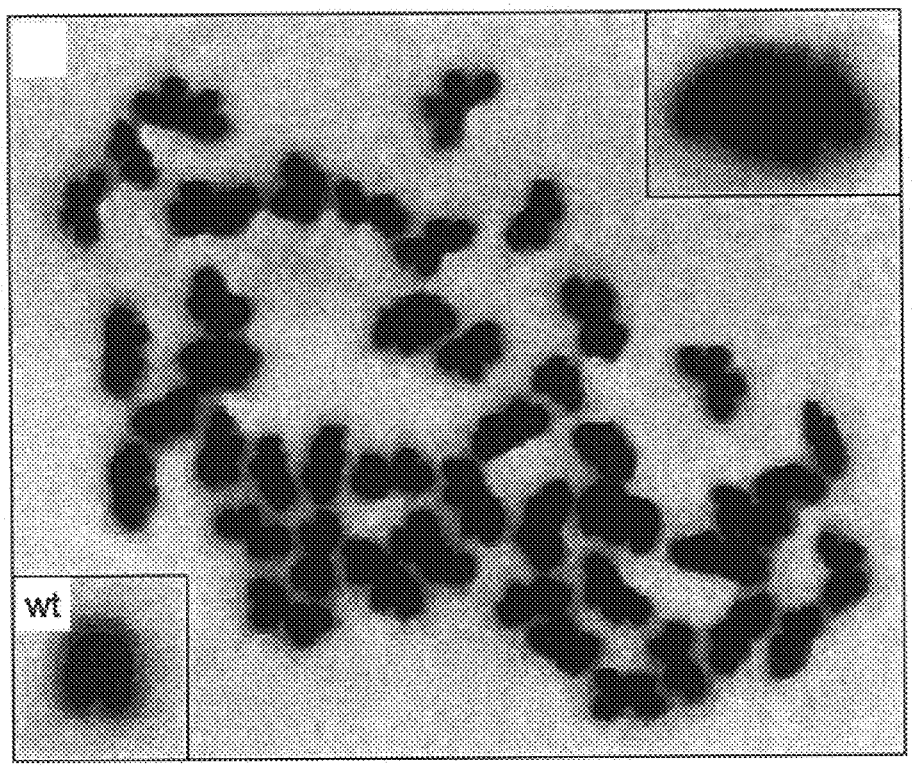

Primary cultures were derived from the lymph nodes of Suv39h dn and of Suv39h1–/–, Suv39h2+/– (null1/het2) tumor mice, and analyzed the karyotypes of the B-cell lymphoma cells. Consistent with the aneuploides described above for Suv39h dn PMEF mass cultures, these tumor cells were largely hyper-diploid but also comprised some hyper-tetraploid karotypes (FIG. 11B). Surprisingly, a fraction of Suv39h dn tumor karyotypes, examined in several independent B-cell lymphomas, is characterized by non-segregated chromosomes that remain attached through their acrocentric regions (FIG. 11C). These 'butterfly' chromosomes raise the intriguing possibility that the absence of Suv39h HMTase activities could impair the quality and function of pericentric heterochromatin by increasing more persistent interactions between metaphase chromosomes. Indeed, analysis of H3-K9 methylation with a newly developed antibody (see Example 11, below) indicates the absence of methH3-K9 staining at pericentric heterochromatin of tumor chromosomes derived from Suv39h null1/het2 B-cell lymphoma cells.

FIG. 11 shows the development of B-cell lymphomas in Suv39h mutant mice as follows: (A) Spleen and lymph nodes of an 11-month old Suv39h dn tumor mouse and of a wild-type control mouse. (B) Karyotype analysis of four independent primary cultures derived from the lymph nodes of tumor-bearing Suv39h dn (null1/null2) and Suv39h1−/−, Suv39h+/− (null1/het2) mice. (C) Metaphase spread from a primary Suv39h dn B-cell lymphoma cell showing 'butterfly' chromosomes that remain associated through their acrocentric regions.

EXAMPLE 11

Absence of H3-K9 Methylation at Suv39h dn Heterochromatin

Figure 12A:
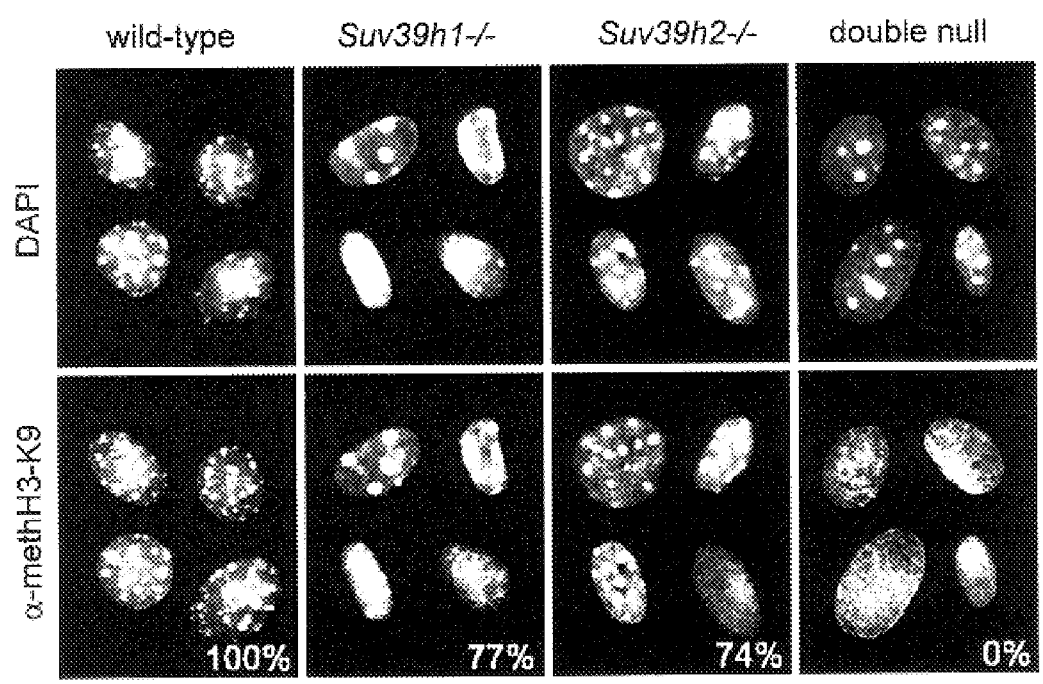

The above karyotype analyses on PMEF and tumor cells suggested a general mechanism through which segregation of the entire chromosome complement may be impaired by Suv39h-dependent defects in pericentric chromatin organization. To assess directly the role of the Suv39h HMTases in histone methylation and heterochromatin formation, a rabbit polyclonal antiserum was raised that specifically recognizes histone H3 when di-methylated at lysine 9 ($\alpha$-methH3-K9). As shown in FIG. 12A, this antiserum detects a focal staining in wt PMEFs that significantly overlaps with DAPI-rich heterochromatin. In PMEFs derived from single Suv39h1- or Suv39h2-deficient mice, ≈75% of cells stain positive for heterochromatic foci with these $\alpha$-methH3-K9 antibodies. Importantly, heterochromatic staining for methH3-K9 was abolished in Suv39h dn PMEFs (FIG. 12A, right row).

Figure 12B:
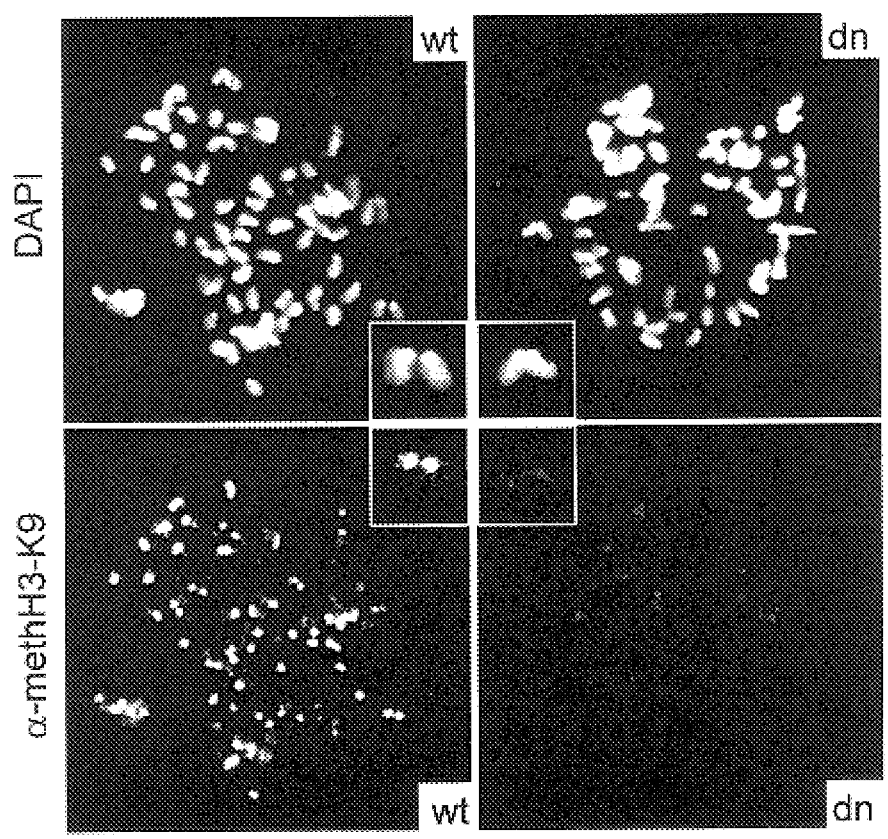

Mitotic chromosome spreads from bone marrow cells were also analyzed with the $\alpha$-methH3-K9 antiserum. In wt spreads, pericentric heterochromatin was selectively visualised (see inserts in FIG. 12B), whereas only residual staining was detected in Suv39h dn spreads. Thus, consistent with the localization of SUV39H1 at active centromeres (Aagaard et al., 2000), these data demonstrate that both Suv39h enzymes are the major HMTases to methylate H3-K9 in pericentric heterochromatin of somatic cells. Moreover, these results also characterize the $\alpha$-methH3-K9 antibodies as a novel cytological marker for heterochromatin and corroborate recent S. pombe studies, in which enrichment of H3-K9 methylation at MAT and CEN regions was shown to be dependent upon a functional Clr4 enzyme (Nakayama et al., 2001).

FIG. 12 shows the Suv39h-dependent H3-K9 methylation at pericentric heterochromatin as follows: (A) DAPI and methH3-K9 staining on interphase chromatin of wild-type (wt), Suv39h1−/−, Suv39h2−/−, and Suv39h dn PMEFs. Percentages refer to interphase nuclei displaying H3-K9 methylation at heterochromatic foci. (B) DAPI and methH3-K9 staining on mitotic chromosomes prepared from in vitro cultured wt and Suv39h dn bone marrow cells.

EXAMPLE 12 a) Hypogonadism and complete spermatogenic failure in Suv39h dn mice

Figure 13A:
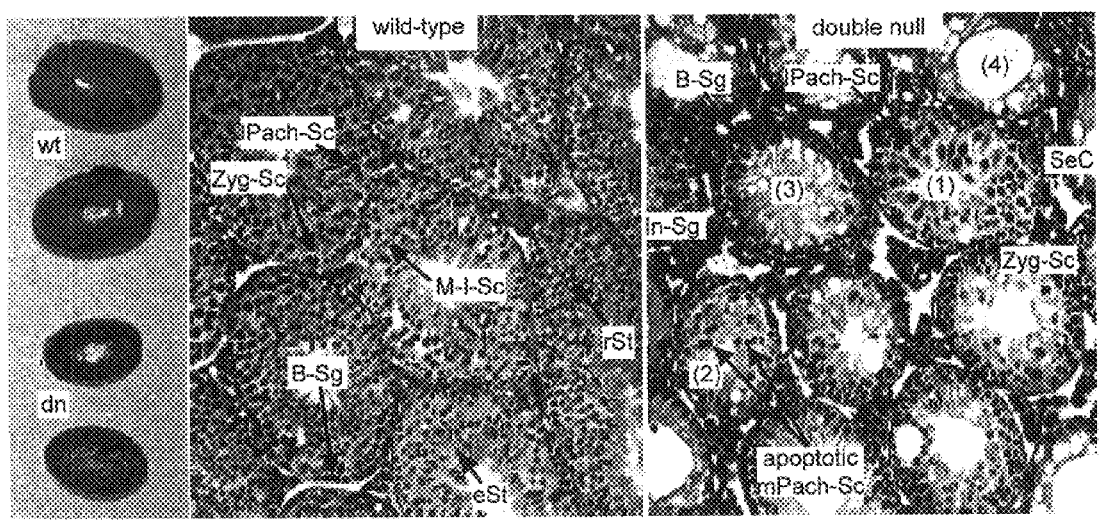

The expression pattern of the Suv39h genes suggests an important role during spermatogenesis (O'Carroll et al., 2000). Indeed, Suv39h dn males (n=7) are infertile, do not contain mature sperm and their testis weights are 3–10 fold reduced as compared to that of wt males (FIG. 13A). To investigate the spermatogenic failure in more detail, histological sections were performed, demonstrating normally developed seminiferous tubules in wt testis which display the characteristic differentiation from the mitotically proliferating spermatogonia (Sg) to meiotic spermatocytes (Sc) and the post-meiotic haploid spermatids (St) (FIG. 13A). By contrast, spermatogenesis was severely impaired in Suv39h dn mice, with an apparent differentiation arrest at the transition between early to late spermatocytes, resulting in highly vacuolarized seminiferous tubules (FIG. 13A).

FISH analyses with mouse major satellite DNA probes and TUNEL assays were used to characterize the Suv39h-dependent spermatogenic defects further. Whereas mitotic proliferation of spermatogonia appeared normal, a 3 to 10 fold increase in the percentage of pre-leptotene spermatocytes was observed. These pre-leptotene spermatocytes often were enlarged. These results suggest that the entry into meiotic prophase is delayed in the absence of Suv39h function. Despite this delay, further progression through meiotic prophase until mid-pachytene appeared normal. Between mid- to late pachytene, however, most spermatocytes undergo apoptosis, resulting in stage V–VI tubules (see FIG. 13A) that largely lack late pachytene spermatocytes and which do not contain haploid spermatids. It was concluded that the absence of Suv39h gene function induces delayed entry into meiotic prophase and triggers pronounced apoptosis of spermatocytes during the mid- to late pachytene stage.

b) H3-K9 methylation at meiotic heterochromatin

Figure 13B:
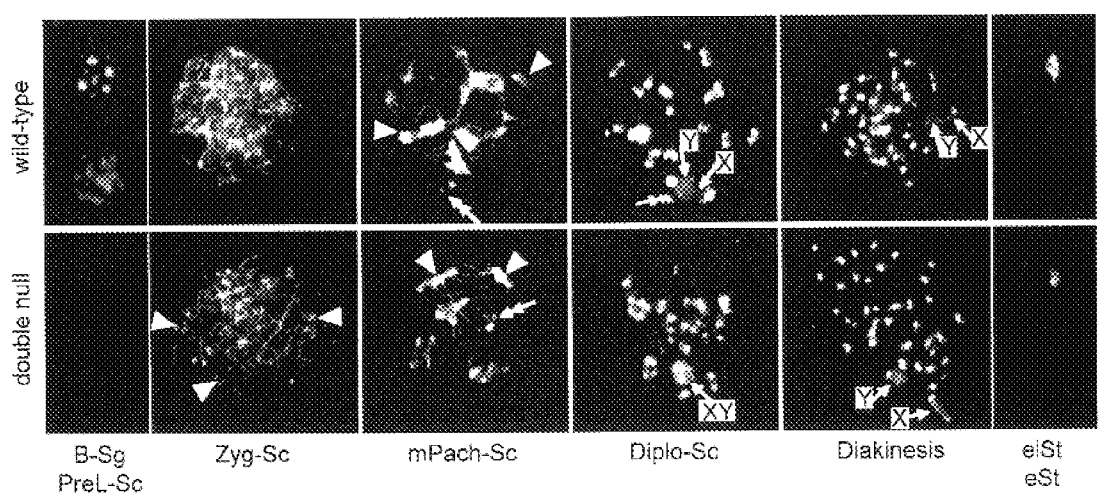

To investigate whether the Suv39h-dependent spermatogenic failure could be correlated with a distinct impairment of meiotic heterochromatin, testis spread preparations and cryosections were analyzed with the $\alpha$-methH3-K9 antibodies. In wt preparations, the ($\alpha$-methH3-K9 antibodies decorate heterochromatic foci in spermatogonia (B-Sg) and in pre-leptotene spermatocytes (preL-Sc) (FIG. 13B, left images, top panel). In early meiotic prophase (Zyg-Sc) and early pachytene, the $\alpha$-methH3-K9 staining was not exclusive for heterochromatin but also extended into euchromatin. From mid-pachytene through diplotene and in diakinesis, the $\alpha$-methH3-K9 staining was restricted to heterochromatic clusters which condense into one block of heterochromatin in elongating spermatids (FIG. 13B, top panels). MethH3-K9 signals in elongated spermatids and mature spermatozoa, in which histones are replaced by protamines, were not detect. The authenticity of this staining pattern had been confirmed in co-localisation analyses with antibodies that recognize the synaptonemal complex (Offenberg et al., 1991; Lammers et al., 1995), HP1$\beta$ (Motzkus et al., 1999) and phosH3 (Cobb et al., 1999). Thus, in analogy to the somatic stainings shown above for PMEFs, these results indicate that methylation of H3-K9 is also a specific marker for meiotic heterochromatin in differentiating male germ cells.

c) Impaired H3-K9 methylation and aneuploidies in Suv39h dn spermatogonia

In preparations from Suv39h dn testis spreads, H3-K9 methylation was absent in spermatogonia and pre-leptotene spermatocytes (FIG. 13B, left images, bottom panel). Further, the pronounced euchromatic staining that characterizes early spermatocytes (Zyg-Sc) at the onset of meiotic prophase was not observed. The impairment of H3-K9 methylation was accompanied by a dispersed distribution of phosH3 in ≈60% of Suv39h dn spermatogonia. By contrast, HP1β was largely undetectable in both wt and Suv39h dn spermatogonia.

Surprisingly, from mid-pachytene onwards, wild-type staining for methH3-K9 at pericentric heterochromatin was observed (FIG. 13B, bottom panel). HP1β localisation and phosH3 signals at autosomes ocurred normally in Suv39h dn late spermatocytes. Thus, these results demonstrate that the Suv39h HMTases selectively regulate H3-K9 methylation in spermatogonia and at the very early stages of meiotic prophase. Similar to the analysis with PMEFs (see above), an ≈5-fold increased rate for complete chromosome mis-segregation in Suv39h dn spermatogonia that results in the occurence of tetraploid spermatocytes ws observed (see FIG. 14C, below). In summary, these data define an early and stage-specific meiotic role for the Suv39h HMTases, and further suggest the existence of a novel H3-K9 HMTase(s) which can methylate heterochromatin during meiotic prophase, diakinesis and in spermatids.

FIG. 13 shows the spermatogenic failure and H3-K9 methylation in germ cells of Suv39h dn mice as follows: (A) Overall size and histology of wild-type and Suv39h dn testes at ≈5 months of age. The Suv39h dn testis section reveals many seminiferous tubules that lack spermatocytes (Sc) and spermatids (St). In particular, although a few seminiferous tubules (1) contain zygotene spermatocytes (Zyg-Sc), more advanced differentiation stages (2) display apoptotic spermatocytes (arrows) at pachytene. At even later differntiation stages (3), pachytene spermatocytes are almost completely absent. Some tubules (4) harbor only Sertoli cells (SeC). Abbreviations: Intermediate (In-Sg) and B-type spermatogonia (B-Sg); pre-leptotene (PreL-Sc), zygotene (Zyg-Sc), mid-pachytene (mPach-Sc), late-pachytene (lPach-Sc), diplotene (Diplo-Sc) and diakinesis/M-I (M-I-Sc) spermatocytes; round (rSt), elongating (elSt) and elongated (eSt) spermatids; Sertoli cells (SeC).

(B) Double-labelling immunofluorescence of wt (top panel) and Suv39h dn (bottom panel) germ cells with α-methH3-K9 (pink) and (α-Scp3 (green) antibodies. DNA was counterstained with DAPI (blue). In Suv39h dn germ cells, H3-K9 methylation is absent in proliferating spermatogonia (B-Sg) and in pre-leptotene spermatocytes (PreL-Sc), and is highly reduced in zygotene spermatocytes (Zyg-Sc) where only residual signals are detected at pericentric heterochromatin (arrowheads). At later stages, H3-K9 methylation appears in a wild-type staining (compare top and bottom panels), although Suv39h dn sex chromosomes (arrows) remain more intensely labeled at diplotene and diakinesis. The double arrow indicates the pseudo-autosomal region (PAR).

EXAMPLE 13 a) Non-homologous interactions and delayed synapsis in Suv39h dn spermatocytes

Figure 14A:
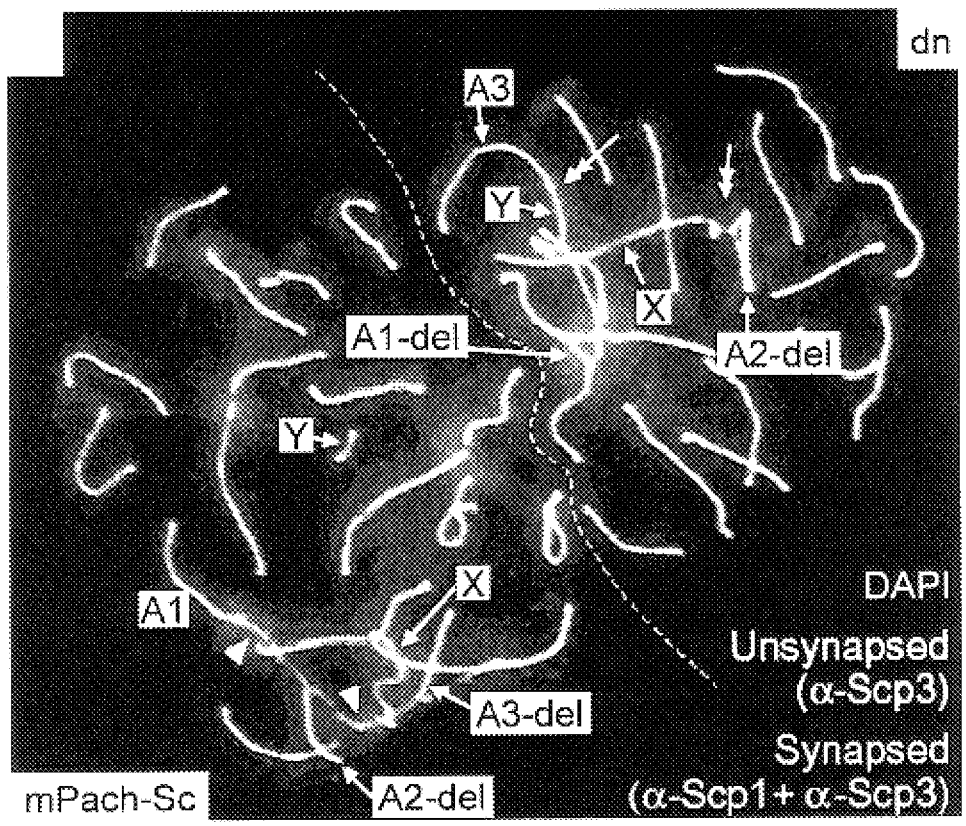
Figures 14B, 14C:
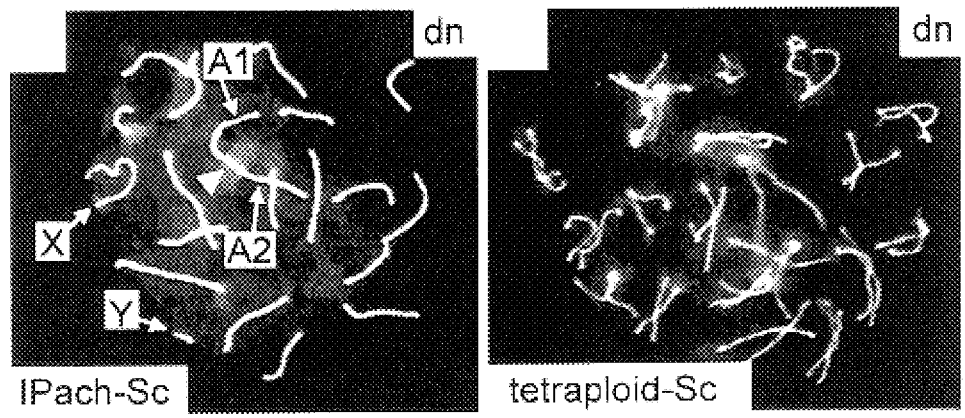
Figures 14H, 14I:
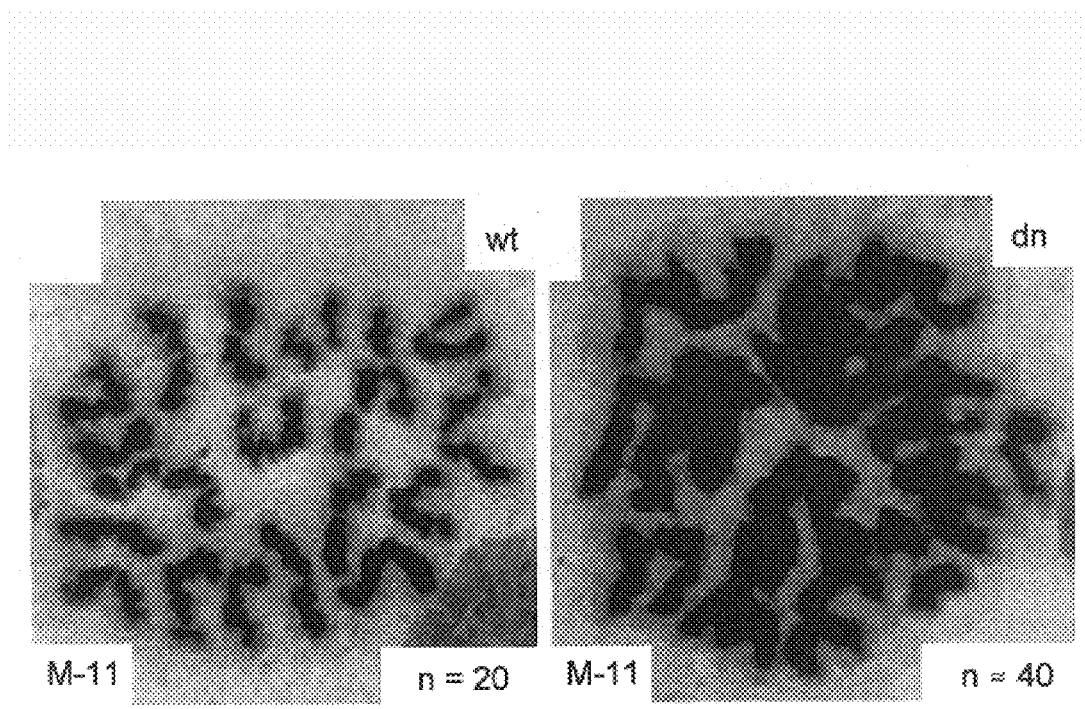
Figure 14J:
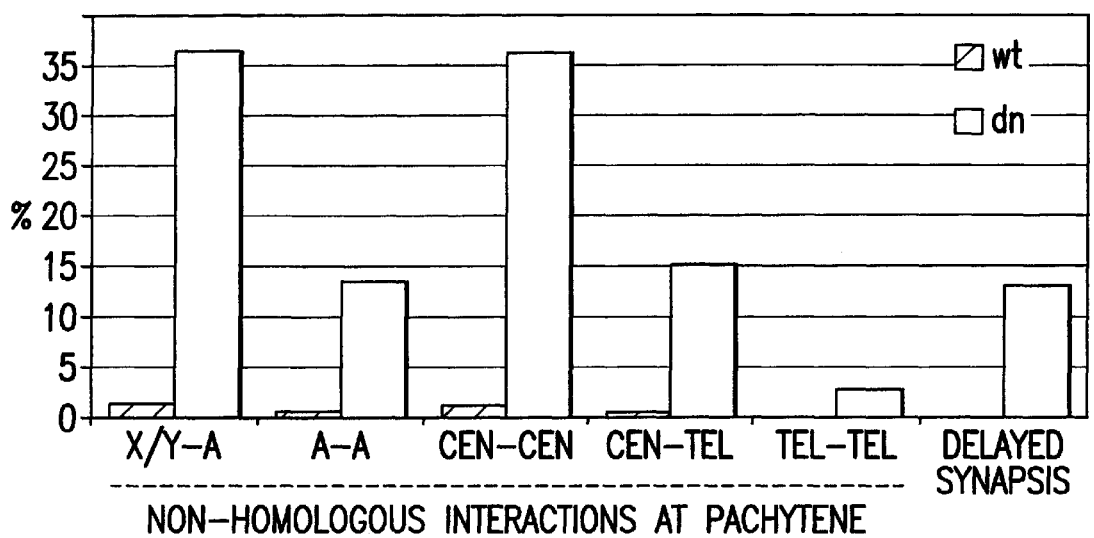

The absence of pericentric H3-K9 methylation in spermatogonia and early spermatocytes is suggestive for a role of the Suv39h HMTases in defining a higher-order structure that may be required for the initial alignments and clustering of meiotic chromosomes. Therefore chromosome synapsis was analyzed by immunofluorescence of pachytene spreads with antibodies that are specific for the axial/lateral and central elements of the synaptonemal complex (SC) (FIG. 14A,B). Intriguingly, in ≈15% (n=90) of Suv39h dn spermatocytes, non-homologous interactions between autosomes were observed (FIG. 14J). Non-homologous interactions were even more frequent (≈35%) between sex chromosomes and autosomes (X/Y-A). Interestingly, these illegitimate associations occurred predominantly between the acrocentric ends (cen-cen) of non-homologous chromosomes, to a lesser extent between centromeres and telomeres (cen-tel) and only very rarely between telomeres (tel-tel) (FIG. 14J). In addition, Suv39h dn spermatocytes contained unsynapsed sex chromosomes (see below) and autosomal bivalents that were delayed in synapsis. Delayed synapsis of autosomes (A-del) almost invariably was correlated with engagement in non-homologous associations (FIG. 14A), suggesting that both processes may be functionally related.

The illegitimate associations were further confirmed by transmission electron microscopy (FIGS. 14D–G). These ultrastructural analyses revealed the presence of physical connections and bridge-like structures between the ends of non-homologous chromosomes (double arrow in FIGS. 14D,C,F). The incidence of partner exchange (FIG. 14G) and non-homologous alignments were also observed. None of these aberrant chromosomal interactions were detected in EM preparations from wt spermatocytes.

b) Bivalent mis-segregation at meiosis I in Suv39h dn spermatocytes

Figure 14K:
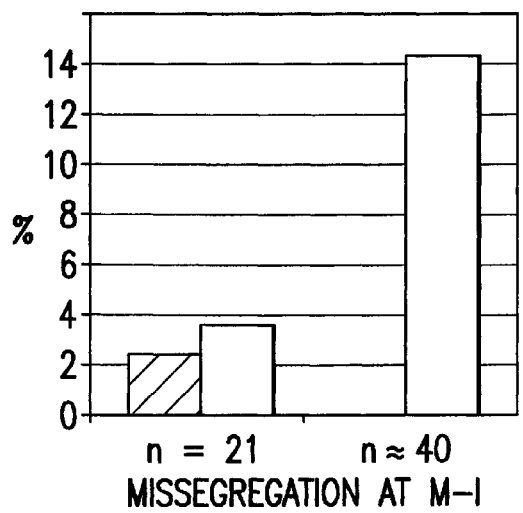

To detemine whether the absence of methH3-K9 in early prophase may affect chromosome dynamics and segregation during the meiotic divisions, testis spread preparations were next analyzed for diakinesis/metaphase I (M-I) and metaphase II (M-II) cells. At diakinesis/M-I, most Suv39h dn spermatocytes revealed bivalents with wt-like morphology, indicating that chromosome condensation and chiasmata formation was unperturbed (but see FIGS. 15B–D, below). However, at M-II, ≈14% of secondary spermatocytes were tetraploid, indicating segregation failure of all bivalents during the first meiotic division (FIGS. 14I and 14K). Therefore, the Suv39h-induced defects at pericentric heterochromatin persist throughout the first meiotic division and do not appear to be 'rescued' by the additional H3-K9 methylation that occurs during mid- to late meiotic prophase (see FIG. 13B).

FIG. 14 shows the illegitimate associations and delayed synapsis of Suv39h dn meiotic chromosomes as follows: (A–C) Double-labelling immunofluorescence of Suv39h dn pachytene spermatocytes with antibodies that are specific for the axial/lateral elements (α-Scp3 (in green) and central elements α-Scp1 (in red) of the synaptonemal complex (SC). This co-labelling reveals unsynapsed chromosomes in a green-like staining and synapsed chromosomes in an orange-red colour. DNA was counterstained with DAPI (blue) which highlights pericentric heterochromatin in a more intense blue contrast. (A) Two mid-pachytene spermatocytes (mPach-Sc) showing multiple illegitimate associations (arrowheads) between non-homologous autosomes (A) and between autosomes and sex chromomes (X, Y). Several autosomes are also delayed in synapsis ($A_{del}$). (B) Late pachytene (lPach-Sc) spermatocyte containing two autosomes which are engaged in non-homologous interaction through their pericentric regions (arrowhead). In addition, the sex chromosomes failed to pair. (C) Tetraploid spermatocyte resulting from complete mis-segregation of all chromosomes in the preceding mitotic division of a Suv39h dn spermatogonium.

(D–G) Transmission electron microscopy of Suv39h dn pachytene chromosomes, confirming that non-homologous chromosome associations mainly occur through pericentric heterochromatin which is visulised by the more granular silver staining (arrowhead and double arrows). The chromosomes displayed in panel G show multiple engagements of partner exchange.

(H, I) Giemsa-stained metaphase II chromosomes of wt and Suv39h dn secondary spermatocytes illustrating complete mis-segregation in the preceeding meiosis I division of Suv39h dn cells.

(J) Histogram for the frequency of non-homologous chromosome associations and delayed synapsis in wt (n=80) and Suv39h dn (n=90) pachytene spermatocytes. (K) Histogram for the frequency of meiosis I mis-segregation of chromosome bivalents in wt (n=40) and Suv39h dn (n=30) secondary spermatocytes.

EXAMPLE 14

Suv39h Deficiency Interferes with Sex Chromosome Segregation

Spermatogenesis in male mammals is specialised by the presence of the heteromorphic sex chromosomes which form a unique chromatin region known as the sex vesicle or XY body (Solari, 1974). Moreover, the Y chromosome is the most heterochromatic chromosome in the mouse (Pardue and Gall, 1970). Homolog pairing and cross-over between sex chromosomes is dependent upon the presence of a small, pseudo-autosomal region called PAR (Burgoyne, 1982). The absence of Suv39h function interferes with the chromatin organization and segregation of the sex chromosomes in several ways.

Figure 15A:
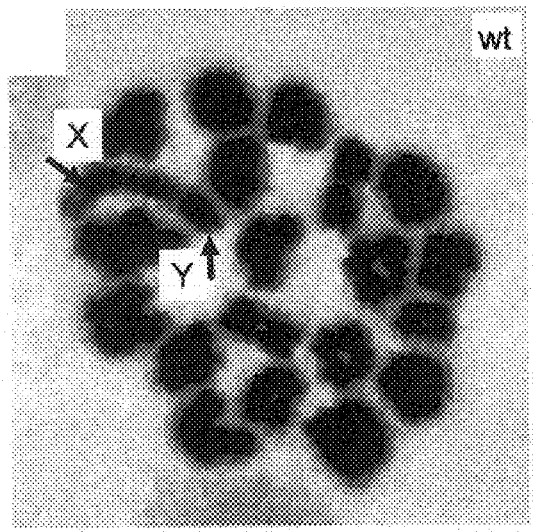
Figure 15B:
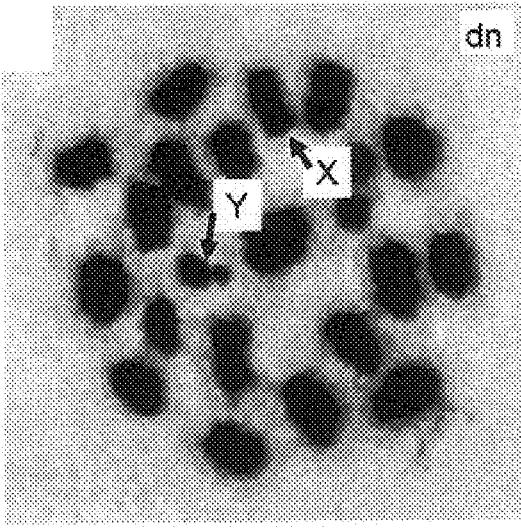
Figure 15C:
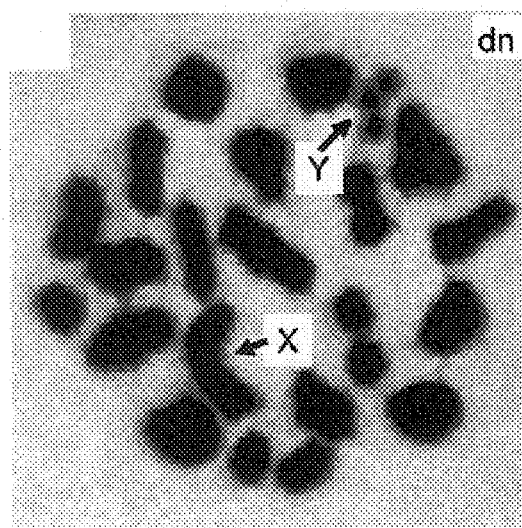
Figure 15D:
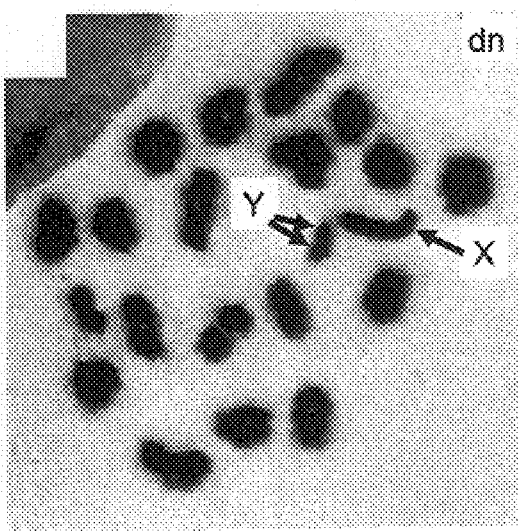
Figure 15E:
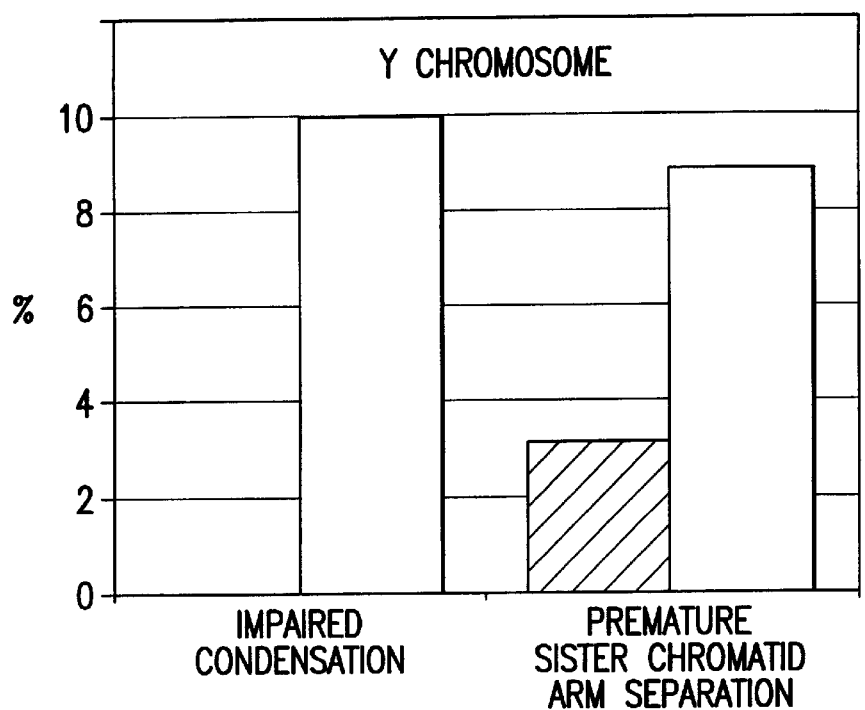
Figure 15F:
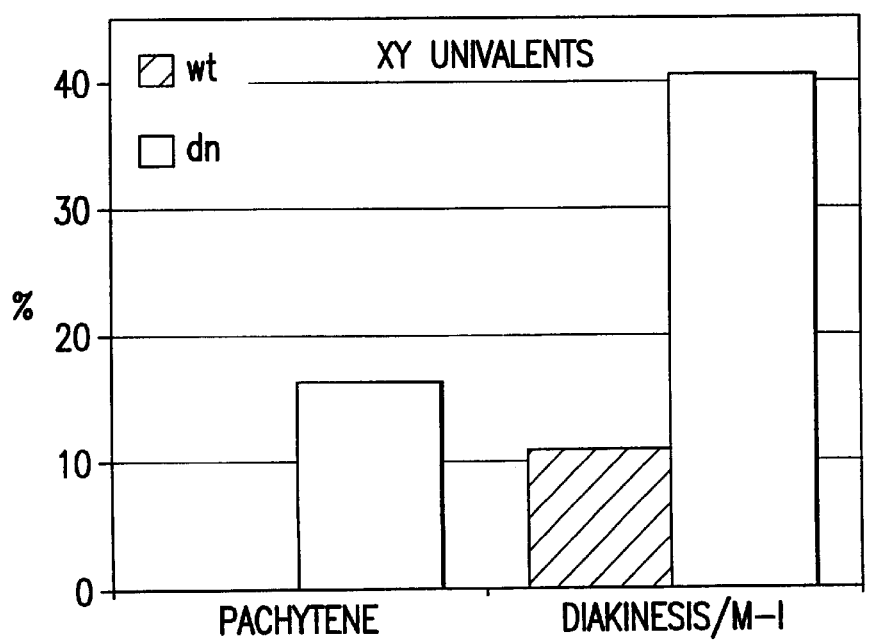
Figure 16A:
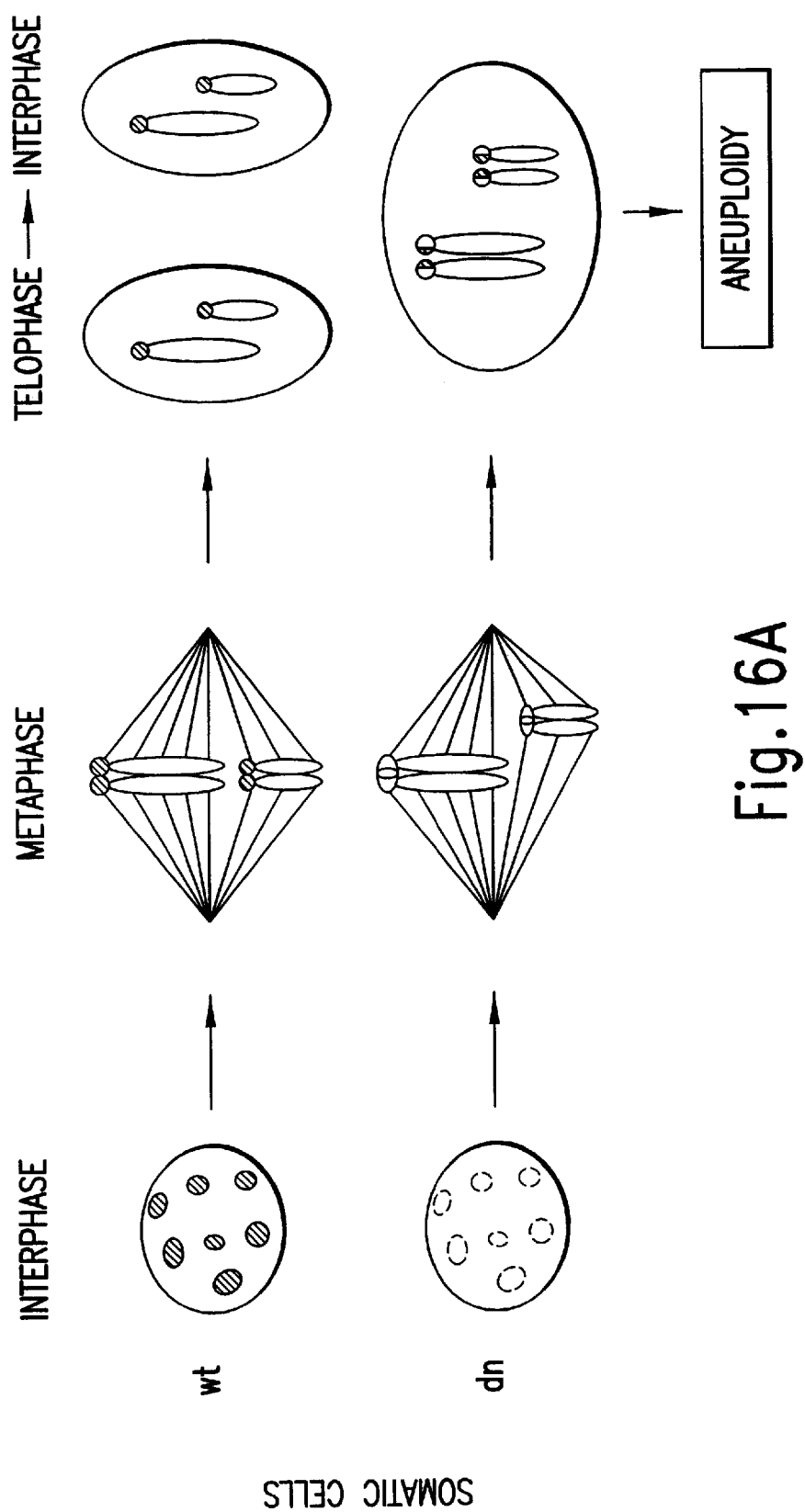
Figure 16B:
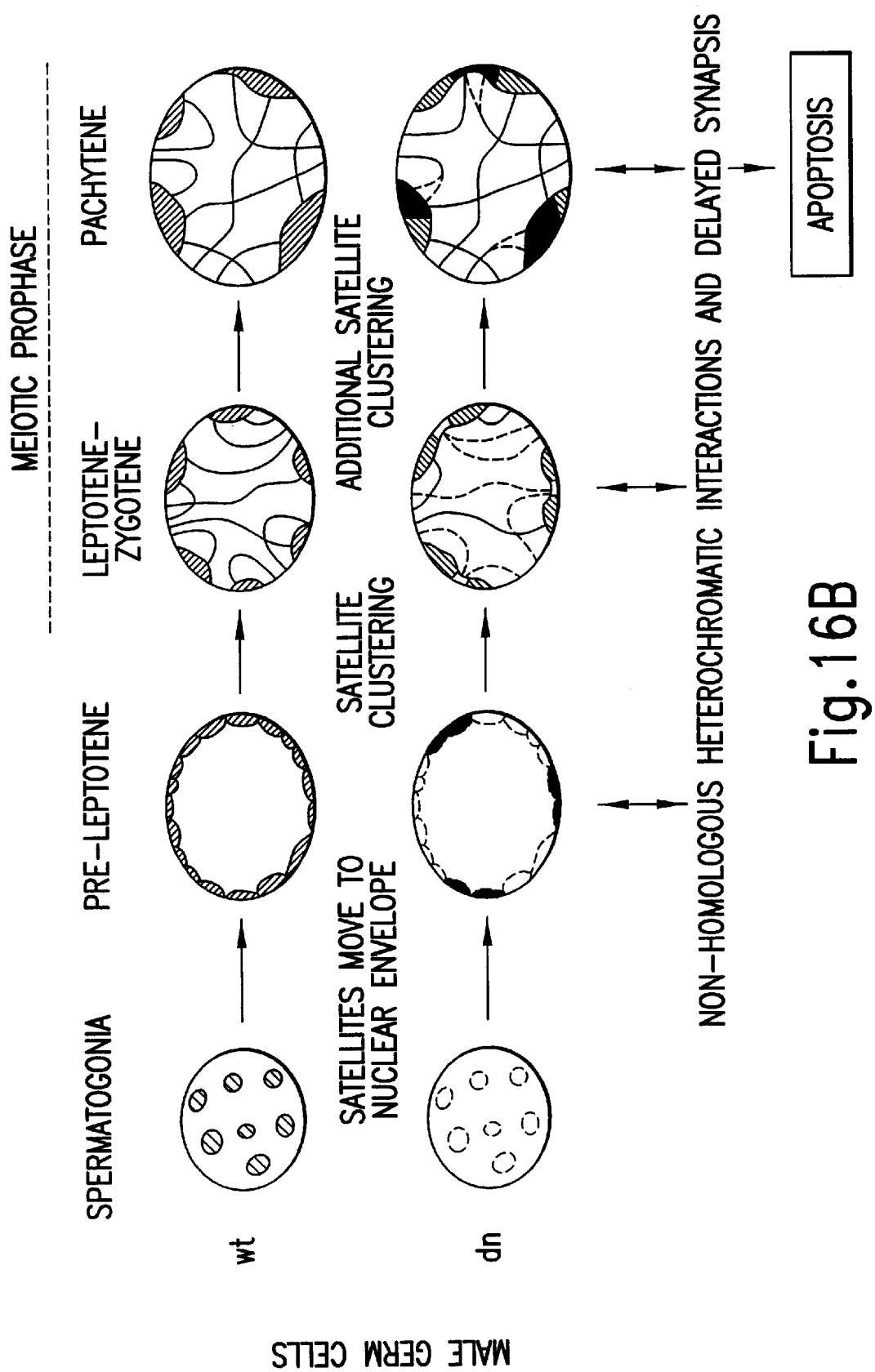

First, although methH3-K9 signals at the XY body (arrows in FIG. 13B) were detected at comparable levels in wt and mutant pachytene spermatocytes, Suv39h dn sex chromosomes remain more heavily methylated in diplotene and diakinesis (see FIG. 13B, bottom panels). Correspondingly, prolonged HP1α binding to the XY body during diplotene was observed. Second, at diakinesis/M-I, the proximal region of the long arm of the Y chromosome appears hypo-condensed in 10% of Suv39h dn cells (FIGS. 15B, E). Moreover, the mutant Y chromosomes display premature separation of their arms or even complete separation of the two sister chromatids (FIGS. 15D, E). Third, H3-K9 methylation is present at the PAR (double arrows in FIG. 13B) in both wt and Suv39h dn sex chromosomes, and the PAR is also decorated with HP1β. Despite these similar staining patterns, the sex chromosomes failed to synapse in ≈15% of Suv39h dn pachytene spermatocytes (FIGS. 14A, B). At diakinesis/M-I (FIGS. 15B, C), the presence of XY univalents was 4-fold increased as compared to wt cells (FIG. 15F). Together, these data indicate a role for the Suv39h HMTases in co-regulating the specialised chromatin structure of the sex chromosomes, in particular of the highly heterochromatic Y chromosome.

FIG. 15 shows the aberrant function of the Y chromosome during meiosis of Suv39h dn spermatocytes as follows: Giemsa-stained diakinesis/metaphase-I chromosomes of wt (A) and Suv39h dn (B–D) primary spermatocytes illustrating univalency (B, C), impaired condensation (B, C) and premature sisterchromatid separation of the Y chromosome (C, D). (E) Histogram for the frequency of diakinesis/M-I cells with abnormal condensation or premature sisterchromatid separation of the Y chromosome (wt: n=190; Suv39h dn: n=170). (F) Histogram for the frequency of XY univalency at pachytene (wt: n=80; Suv39h dn: n=80) or diakinesis/M-I (wt: n=190; Suv39h dn: n=170).

EXAMPLE 15

Screening for Moduators of Suv39h1 MTase Activity.

All steps are automated and the position of the different test compounds are registered on computer for later reference. Compounds being tested for modulating activity are aliquoted into 384 well plates in duplicate. 20–200 nmol of recombinant GST tagged SUV39H1 in MAB buffer, is then added to the reaction. 20 nmol of branched peptide ([TARKST]$_4$-K$_2$-K-cys) which has been labelled with europium is then added, followed by 100 nmol of S-adenosyl methionine. This reaction is left at room temperature for 40 mins, then transferred onto a second plate to which the α-methH3-K9 antibody has been coated. This reaction is then left at room temperature for 40 mins to allow the antibody to bind methylated substrate. Following capture of methylated substrate, unbound non-methylated substrate is washed off in 50 mM tris pH 8.5. The europium label is then cleaved from the peptide in 50 μl pH 4.5 enhancement solution for 25 mins. The chelated europium molecules are then excited at 360 nm and the level of emitted fluorescence at 620 nm is then calculated using time-resolved fluorescence in a PolarStar plate reader. The results are then automatically graphed.

The level of fluorescence is directly related to the level of MTase activity. The effect of the different compounds on the MTase activity can be clearly seen on the graph when compared to control reactions with no componds added or with no enzyme added.

Figures 17A, 17B:
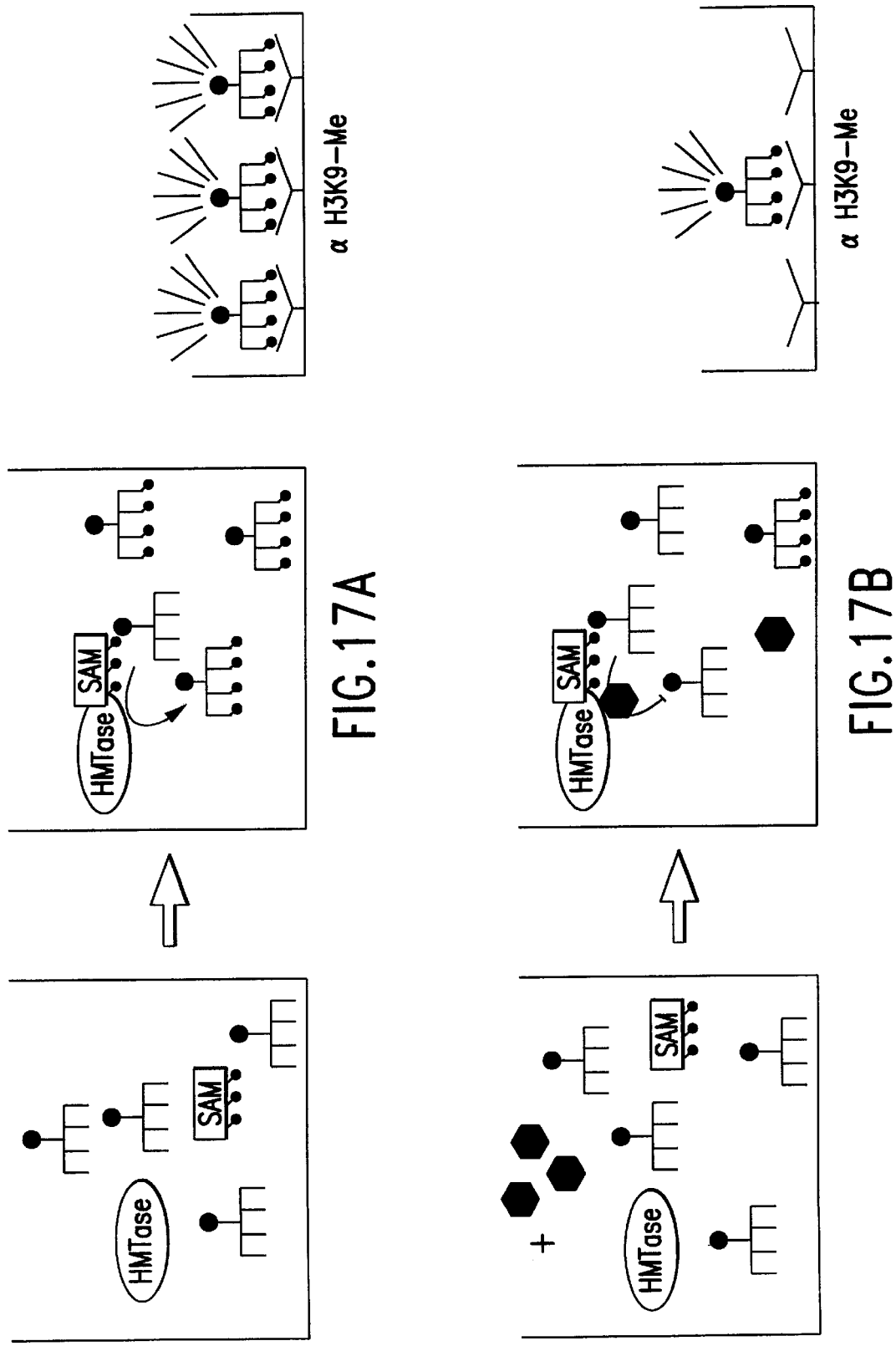

FIG. 17 illustrates the principle of the screening method as follows:

a) A Suv39h1-like MTase is incubated with S-Adenosyl Methionine (SAM) and a chromogenically labelled unmodified peptide substrate (e.g. branched peptide [TARKST]4-K2-K-cys). Following methylation of this substrate the substrate becomes an epitope for a Lys9-methyl specific antibody which has been immobilised on a microtiter plate. The level of bound peptide can then be quantified by the level of fluorescence of from the chromogenic label.

b) In the presence of a modulator (e.g. an inhibitor, I) the transfer of methyl groups by the MTase will be affected (decreased), this in turn will affect the amount of substrate captured by the immobilised antibody, which is quantified by the level of fluorescence. A compound with inhibitory effects will result in a decrease in fluorescent signal, whereas a compound with enhancing effects will result in an increase in fluorescent signal.

TABLE I

Viability of Suv39h double null mice.

| cross<br>dn mice expected | N1H2 ×<br>H1H2[a]<br>1:8 | N1H2 ×<br>N1H2<br>1:4 | N1H2 ×<br>H1N2<br>1:4 | total |
|---|---|---|---|---|
| total # mice born | 81 | 89 | 27 | 197 |
| # dn mice expected[b] | 11 | 27 | 8 | 46 |
| # dn mice observed | 4 | 8 | 3 | 15 |
| % dn mice viable | 36.4 | 29.6 | 37.5 | 32.6 |

[a]i.e.: N1H2 × H1H2: ♂♂ Suv39h1 −/−, Suv39h2 +/− × ♀♀ Suv39h1 +/−, Suv39h2 +/−
[b]Based on number of mice born with other Suv39h1 and Suv39h2 allelic combinations which show no reduced prenatal viability.

TABLE II

Incidence of B-cell lymphomas in mice with reduced Suv39h gene dosage

| Genotype | Suv39h gene dosage | # of mice with tumor | total # of mice | % of mice with tumor |
| --- | --- | --- | --- | --- |
| W1W2 | 3 | 0 | 57 | 0 |
| W1H2, W1N2, H1N2 | 0–2 | 1 | 22 | 4.6 |
| H1W2, N1W2 | 2–3 | 8 | 26 | 30.8 |
| H1H2, N1H2* | 1–2 | 20 | 72 | 27.8 |
| N1N2 | 0 | 2 | 6 | 33.3 |

*i.e.: N1H2: Suv39h1 –/–, Suv39h2 +/–

REFERENCES

Aagaard, L., Laible, G., Selenko, P., Schmid, M., Dorn, R., Schotta, G., Kuhfittig, S., Wolf, A., Lebersorger, A., Singh, P. B., Reuter, G. and Jenuwein, T. (1999) Functional mammalian homologues of the Drosophila PEV-modifier Su(var)3-9 encode centromere-associated proteins which complex with the heterochromatin component M31. Embo J, 18, 1923–38.

Aagaard, L., Schmid, M., Warburton, P., and Jenuwein, T. (2000). Mitotic phosphorylation of SUV39H1, a novel component of active centromeres, coincides with transient accumulation at mammalian centromeres. J Cell Sci, 113, 817–829.

Aasland, R. and Stewart, A. F. (1995) The chromo shadow domain, a second chromo domain in heterochromatin-binding protein 1, HP1. Nucleic Acids Res, 23, 3168–74.

Adams, R. R., Wheatleya, S. P., Gouldsworthy, A. M., Kandels-Lewis, S. E., Carmena, M., Smythe, C., Gerloff, D. L., and Earnshaw, W. C. (2000). INCENP binds the Aurora-related kinase AIRK2 and is required to target it to chromosomes, the central spindle and cleavage furrow. Curr Biol, 10, 1075–1078.

Ainsztein, A. M., Kandels-Lewis, S. E., Mackay, A. M., and Earnshaw, W. C. (1998). INCENP centromere and spindle targeting: identification of essential conserved motifs and involvement of heterochromatin protein HP1. J Cell Biol, 143, 1763–1774.

Allshire, R. C., Nimmo, E. R., Ekwall, K., Javerzat, J. P. and Cranston, G. (1995) Mutations derepressing silent centromeric domains in fission yeast disrupt chromosome segregation. Genes Dev, 9, 218–33.

Altschul, S. F., Madden, T. L., Schaffer, A. A., Zhang, J., Zhang, Z., Miller, W. and Lipman, D. J. (1997) Gapped BLAST and PSI-BLAST: a new generation of protein database search programs. Nucleic Acids Res, 25, 3389–402.

Baksa, K., Morawietz, H., Dombradi, V., Axton, M., Taubert, H., Szabo, G., Torok, I., Udvardy, A., Gyurkovics, H., Szoor, B. and et al. (1993) Mutations in the protein phosphatase 1 gene at 87B can differentially affect suppression of position-effect variegation and mitosis in Drosophila melanogaster. Genetics, 135, 117–25.

Ball, L. J., Murzina, N. V., Broadhurst, R. W., Raine, A. R. C., Archer, S. J., Stott, F. J., Murzin, A. G., Singh, P. B., Domaille, P. J. and Laue, E. D. (1997) Structure of the chromatin binding (chromo) domain from mouse modifier protein 1. EMBO J, 16, 2473–2481.

Bannister, A. J., Zegerman, P., Partridge, J. F., Miska, E. A., Thomas, J. O., Allshire, R. C., and Kouzarides, T. (2001). Selective recognition of methylated lysine 9 on histone H3 by the HP1 chromo domain. Nature, 410, 120–124.

Baudat, F., Manova, K., Yuen, J. P., Jasin, M., and Keeney, S. (2000). Chromosome synapsis defects and sexually dimorphic meiotic progression in mice lacking spo1 1. Mol Cell, 6, 989–998.

Bernard, P., Hardwick, K., and Javerzat, J. P. (1998). Fission yeast Bub1 is a mitotic centromere protein essential for the spindle checkpoint and the preservation of correct ploidy through mitosis. J Cell Biol, 143, 1775–1787.

Birney, E., Thompson, J. D. and Gibson, T. J. (1996) PairWise and SearchWise: finding the optimal alignment in a simultaneous comparison of a protein profile against all DNA translation frames. Nucleic Acids Res, 24, 2730–9.

Burgoyne, P. S. (1982). Genetic homology and crossing over in the X and Y chromosomes of mammals. Hum Genet, 61, 85–90.

Chen, D., Ma, H., Hong, H., Koh, S. S., Huang, S. M., Schurter, B. T., Aswad, D. W. and Stallcup, M. R. (1999) Regulation of transcription by a protein methyltransferase. Science, 284, 2174–7.

Cléard, F., Delattre, M. and Spierer, P. (1997) SU(VAR)3-7, a Drosophila heterochromatin-associated protein and companion of HP1 in the genomic silencing of position-effect variegation. Embo J, 16, 5280–8.

Cobb, J., Miyaike, M., Kikuchi, A., and Handel, M. A. (1999). Meiotic events at the centromeric heterochromatin: histone H3 phosphorylation, topoisomerase II alpha localization and chromosome condensation. Chromosoma, 108, 412–425.

Cortez, D. and Elledge, S. J. (2000). Conducting the mitotic symphony. Nature, 406, 354–356.

Csink, A. and Henikoff, S. (1996). Genetic modification of heterochromatic association and nuclear organization in Drosophila. Nature, 381, 529–531.

Cutts, S. M., Fowler, K. J., Kile, B. T., Hii, L. L., O'Dowd, R. A., Hudson, D. F., Saffery, R., Kalitsis, P., Earle, E., and Choo, K. H. (1999). Defective chromosome segregation, microtubule bundling and nuclear bridging in inner centromere protein gene (Incenp)-disrupted mice. Hum Mol Genet, 8, 1145–1155.

Dernburg, A. F., Broman, K. W., Fung, J. C., Marshall, W. F., Philips, J., Agard, D. A., and Sedat, J. W. (1996a). Perturbation of nuclear architecture by long-distance chromosome interactions. Cell, 85, 745–759.

Dernburg, A. F., Sedat, J. W., and Hawley, R. S. (1996b). Direct evidence of a role for heterochromatin in meiotic chromosome segregation. Cell, 86, 135–146.

De Rubertis, F., Kadosh, D., Henchoz, S., Pauli, D., Reuter, G., Struhl, K. and Spierer, P. (1996) The histone deacetylase RPD3 counteracts genomic silencing in Drosophila and yeast. Nature, 384, 589–91.

de Vries, S. S., Baart, E. B., Dekker, M., Siezen, A., de Rooij, D. G., de Boer, P., and te Riele, H. (1999). Mouse MutS-like protein Msh5 is required for proper chromosome synapsis in male and female meiosis. Genes Dev, 13, 523–531.

Eddy, S. R. (1998) Profile hidden Markov models. Bioinformatics, 14, 755–63.

Eissenberg, J. C., Morris, G. D., Reuter, G. and Hartnett, T. (1992) The heterochromatin-associated protein HP-1 is an essential protein in Drosophila with dosage-dependent effects on position-effect variegation. Genetics, 131, 345–52.

Ekwall, K., Nimmo, E. R., Javerzat, J. P., Borgstrom, B., Egel, R., Cranston, G. and Allshire, R. C. (1996) Mutations in the fission yeast silencing factors clr4+ and rik1+ disrupt the localisation of the chromo domain protein Swi6p and impair centromere function. J Cell Sci, 109, 2637–48.

Ekwall, K., Olsson, T., Turner, B. M., Cranston, G., and Allshire, R. C. (1997). Transient inhibition of histone deacetylation alters the structural and functional imprint at fission yeast centromeres. Cell, 91, 1021–1032.

Foon, K. A., and Gale, R. P. (1995). Chronic Lymphoid Leukemias. In Blood: Principles and Practise of Hematology, R. I. Handin, T. P. Stossel and S. E. Lux, eds. (J.B. Lippincott Company, Philadelphia), pp783–81 1.

Frishman, D. and Argos, P. (1997) Seventy-five percent accuracy in protein secondary structure prediction. Proteins, 27, 329–35.

Grunstein, M. (1998) Yeast heterochromatin: regulation of its assembly and inheritance by histones. Cell, 93, 325–8.

Hawley, R. S., Irick, H., Zitron, A. E., Haddox, D. A., Lohe, A., New, C., Whitley, M. D., Arbel, T., Jang, J., McKim, K., and et al. (1992). There are two mechanisms of achiasmate segregation in Drosophila females, one of which requires heterochromatic homology. Dev Genet, 13, 440–467.

Heitz, E. (1928). Das Heterochromatin der Moose. Jhrb. Wiss. Botanik, 69, 762–818.

Hendzel, M. J., Wei, Y., Mancini, M. A., Van Hooser, A., Ranalli, T., Brinkley, B. R., Bazett-Jones, D. P. and Allis, C. D. (1997) Mitosis-specific phosphorylation of histone H3 initiates primarily within pericentromeric heterochromatin during G2 and spreads in an ordered fashion coincident with mitotic chromosome condensation. Chromosoma, 106, 348–60.

Henikoff, S. (1997) Position effect variegation in Drosophila: recent progress. Epigenetic mechanisms of gene regulation. CSHL press.

Hsu, J. Y., Sun, Z. W., Li, X., Reuben, M., Tatchell, K., Bishop, D. K., Grushcow, J. M., Brame, C. J., Caldwell, J. A., Hunt, D. F., Lin, R., Smith, M. M., and Allis, C. D. (2000). Mitotic phosphorylation of histone H3 is governed by Ipl1/aurora kinase and Glc7/PP1 phosphatase in budding yeast and nematodes. Cell, 102, 279–291.

Ivanova, A. V., Bonaduce, M. J., Ivanov, S. V. and Klar, A. J. (1998) The chromo and SET domains of the Clr4 protein are essential for silencing in fission yeast. Nat Genet, 19, 192–5.

Jacobson, S. and Pillus, L. (1999) Modifying chromatin and concepts of cancer. Curr Opin Genet Dev, 9, 175–84

Jenuwein, T., Laible, G., Dorn, R. and Reuter, G. (1998) SET domain proteins modulate chromatin domains in eu- and heterochromatin. Cell Mol Life Sci, 54, 80–93.

Jenuwein, T. (2001). Re-SET-ting heterochromatin by histone methyltransferases. Trends Cell Biol, 11, 266–273.

Jones, D. A., Cowell, F. G., and Singh, P. B. (2000). Bioessays, 22, 124-

Kaitna, S., Mendoza, M., Jantsch-Plunger, V., and Glotzer, M. (2000). Incenp and an aurora-like kinase form a complex essential for chromosome segregation and efficient completion of cytokinesis. Curr Biol, 10, 1172–1181.

Karpen, G. H., Le, M. H., and Le, H. (1996). Centric heterochromatin and the efficiency of achiasmate disjunction in Drosophila female meiosis. Science, 273, 118–122.

Karpen, G. H. and Allshire, R. C. (1997) The case for epigenetic effects on centromere identity and function. Trends Genet, 13, 489–496.

Klein, R. R. and Houtz, R. L. (1995) Cloning and developmental expression of pea ribulose-1,5-bisphosphate carboxylase/oxygenase large subunit N-methyltransferase. Plant Mol Biol, 27, 249–61.

Koonin, E. V., Zhou, S. and Lucchesi, J. C. (1995) The chromo superfamily: new members, duplication of the chromo domain and possible role in delivering transcription regulators to chromatin. Nucleic Acids Res, 23, 4229–33.

Lachner, M., O'Carroll, D., Rea, S., Mechtler, K., and Jenuwein, T. (2001). Methylation of histone H3 lysine 9 creates a binding site for HP1 proteins. Nature, 410, 116–120.

Laible, G., Wolf, A., Dorn, R., Reuter, G., Nislow, C., Lebersorger, A., Popkin, D., Pillus, L. and Jenuwein, T. (1997) Mammalian homologues of the Polycomb-group gene Enhancer of zeste mediate gene silencing in Drosophila heterochromatin and at S. cerevisiae telomeres. Embo J, 16, 3219–32.

Lamb, D J, Niederberger, C S. (1994) Animal models that mimic human male reproductive defects. Urol Clin North Am Aug;21(3):377–87

Lammers, J. H., van Aalderen, M., Peters, A. H. F. M., van Pelt, A. A., de Rooij, D. G., de Boer, P., Offenberg, H. H., Dietrich, A. J., and Heyting, C. (1995). A change in the phosphorylation pattern of the 30,000–33,000 Mr synaptonemal complex proteins of the rat between early and mid-pachytene. Chromosoma, 104, 154–163.

Larsson, J., Zhang, J. and Rasmuson-Lestander, A. (1996) Mutations in the Drosophila melanogaster gene encoding S-adenosyl-methionine synthetase suppress position-effect variegation [published erratum appears in Genetics (1996) 144,1329]. Genetics, 143, 887–96.

Lengauer, C., Kinzler, K. W. and Vogelstein, B. (1997) Genetic instability in colorectal cancers. Nature, 386, 623–7.

Martzen, M. R., McCraith, S. M., Spinelli, S. L., Torres, F. M., Fields, S., Grayhack, E. J. and Phizicky, E. M. (1999) A biochemical genomics approach for identifying genes by the activity of their products. Science, 286, 1153–5.

Melcher, M., Schmid, M., Aagaard, L., Selenko, P., Laible, G. and Jenuwein, T. (2000) Structure-function analysis of SUV39H1 reveals a dominant role in heterochromatin organization, chromosome segregation, and mitotic progression. Mol Cell Biol, 20, 3728–41.

Motzkus, D., Singh, P. B., and Hoyer-Fender, S. (1999). M31, a murine homolog of Drosophila HP1, is concentrated in the XY body during spermatogenesis. Cytogenet Cell Genet, 86, 83–88.

Nakayama, J., Rice, J. C., Strahl, B. D., Allis, C. D., and Grewal, S. I. (2001). Role of histone H3 lysine 9 methylation in epigenetic control of heterochromatin assembly. Science, 292, 110–113.

O'Carroll, D., Scherthan, H., Peters, A. H. F. M., Opravil, S., Haynes, A. R., Laible, G., Rea, S., Schmid, M., Lebersorger, A., Jerratsch, M., Sattler, L., Mattei, M. G., Denny, P., Brown, S. D., Schweizer, D., and Jenuwein, T. (2000). Isolation and characterization of Suv39h2, a second histone H3 methyltransferase gene that displays testis-specific expression. Mol Cell Biol, 20, 9423–9433.

Offenberg, H. H., Dietrich, A. J., and Heyting, C. (1991). Tissue distribution of two major components of synaptonemal complexes of the rat. Chromosoma, 101, 83–91.

Pardue, M. L., and Gall, J. G. (1970). Chromosomal localization of mouse satellite DNA. Science, 168, 1356–1358.

Peters, A. H. F. M., Plug, A. W., van Vugt, M. J., and de Boer, P. (1997a). A drying-down technique for the spreading of mammalian meiocytes from the male and female germline. Chromosome Res, 5, 66–68.

Peters, A. H. F. M., Plug, A. W., and de Boer, P. (1997b). Meiosis in carriers of heteromorphic bivalents: sex differences and implications for male fertility. Chromosome Res, 5, 313–324.

Pehrson, J. R. and Fried, V. A. (1992) MacroH2A, a core histone containing a large nonhistone region. Science, 257, 1398–400.

Platero, J. S., Hartnett, T. and Eissenberg, J. C. (1995) Functional analysis of the chromo domain of HP1. Embo J, 14, 3977–86.

Rea, S., Eisenhaber, F., O'Carroll, D., Strahl, B. D., Sun, Z. W., Schmid, M., Opravil, S., Mechtler, K., Ponting, C. P., Allis, C. D., and Jenuwein, T. (2000). Regulation of chromatin structure by site-specific histone H3 methyltransferases. Nature, 406, 593–599.

Reuter, G. and Spierer, P. (1992) Position effect variegation and chromatin proteins. BioEssays, 14, 605–612.

Rice, J. C. and Allis, C. D. (2001) Histone methylation versus acetylation: new insights into epigenetic regulation. Curr Opin Cell Biol, 13, 263–273.

Sassone-Corsi, P., Mizzen, C. A., Cheung, P., Crosio, C., Monaco, L., Jacquot, S., Hanauer, A. and Allis, C. D. (1999) Requirement of Rsk-2 for epidermal growth factor-activated phosphorylation of histone H3. Science, 285, 886–91.

Scherthan, H., Weich, S., Schwegler, H., Heyting, C., Harle, M., and Cremer, T. (1996). Centromere and telomere movements during early meiotic prophase of mouse and man are associated with the onset of chromosome pairing. J Cell Biol, 134, 1109–1125.

Schotta, G. and Reuter, G. (2000) Controlled expression of tagged proteins in Drosophila using a new modular P-element vector system. Mol Gen Genet, 262, 916–20.

Schultz, J., Copley, R. R., Doerks, T., Ponting, C. P. and Bork, P. (2000) SMART: a web-based tool for the study of genetically mobile domains. Nucleic Acids Res, 28, 231–4.

Solari, A. J. (1974). The behavior of the XY pair in mammals. Int Rev Cytol, 38, 273–317.

Stassen, M. J., Bailey, D., Nelson, S., Chinwalla, V. and Harte, P. J. (1995) The Drosophila trithorax proteins contain a novel variant of the nuclear receptor type DNA binding domain and an ancient conserved motif found in other chromosomal proteins. Mech Dev, 52, 209–23.

Strahl, B. D. and Allis, C. D. (2000) The language of covalent histone modifications. Nature, 403, 41–5.

Strahl, B. D., Ohba, R., Cook, R. G. and Allis, C. D. (1999) Methylation of histone H3 at lysine 4 is highly conserved and correlates with transcriptionally active nuclei in Tetrahymena. Proc Natl Acad Sci U S A, 96, 14967–72.

Sullivan, K. F., Hechenberger, M. and Masri, K. (1994) Human CENP-A contains a histone H3 related histone fold domain that is required for targeting to the centromere. J Cell Biol, 127, 581–92.

Tkachuk, D. C., Kohler, S. and Cleary, M. L. (1992) Involvement of a homolog of Drosophila trithorax by 11 q23 chromosomal translocations in acute leukemias. Cell, 71, 691–700.

Tschiersch, B., Hofmann, A., Krauss, V., Dorn, R., Korge, G. and Reuter, G. (1994) The protein encoded by the Drosophila position-effect variegation suppressor gene Su(var) 3-9 combines domains of antagonistic regulators of homeotic gene complexes. Embo J, 13, 3822–31.

Turner, B. M. (1998) Histone acetylation as an epigenetic determinant of long-term transcriptional competence. Cell Mol Life Sci, 54, 21–31.

Turner, J. M., Mahadevaiah, S. K., Benavente, R., Offenberg, H. H., Heyting, C., and Burgoyne, P. S. (2000). Analysis of male meiotic "sex body" proteins during XY female meiosis provides new insights into their functions. Chromosoma, 109,426–432.

Vigil P, Bustos-Obregon E. (1985) Alkylating agents and mouse spermatogenesis: effects of a single dose of cyclophosphamide. Andrologia May-Jun;17(3):276–82

Wallrath, L. L. (1998) Unfolding the mysteries of heterochromatin. Curr Opin Genet Dev, 8, 147–53.

Wei, Y., Yu, L., Bowen, J., Gorovsky, M. A. and Allis, C. D. (1999) Phosphorylation of histone H3 is required for proper chromosome condensation and segregation. Cell, 97, 99–109.

Weinbauer G F, Aslam H, Krishnamurthy H, Brinkworth M H, Einspanier A, Hodges J K. (2001). Quantitative analysis of spermatogenesis and apoptosis in the common marmoset (Callithrix jacchus) reveals high rates of spermatogonial turnover and high spermatogenic efficiency.

Working P K. (1988) Male reproductive toxicology: comparison of the human to animal models. Environ Health Perspect Apr;77:37–44

Wreggett, K. A., Hill, F., James, P. S., Hutchings, A., Butcher, G. W., and Singh, P. B. (1994). A mammalian homologue of Drosophila heterochromatin protein 1 (HP1) is a component of constitutive heterochromatin. Cytogenet Cell Genet, 66, 99–103.

Xu, X., Weaver, Z., Linke, S. P., Li, C., Gotay, J., Wang, X. W., Harris, C. C., Ried, T. and Deng, C. X. (1999) Centrosome amplification and a defective G2-M cell cycle checkpoint induce genetic instability in BRCA1 exon 11 isoform-deficient cells. Mol Cell, 3, 389–95.

Xu, Y., Ashley, T., Brainerd, E. E., Bronson, R. T., Meyn, M. S., and Baltimore, D. (1996). Targeted disruption of ATM leads to growth retardation, chromosomal fragmentation during meiosis, immune defects, and thymic lymphoma. Genes Dev, 10, 2411–2422.

Yoshida, K., Kandoh, G., Matsuda, Y., Habu, T., Nishimune, Y., and Morita, T. (1998). The mouse RecA-like gene Dmc1 is required for homologous chromosome synapsis during meiosis. Mol Cell, 1, 707–718.

Yuan, L., Liu, J. G., Zhao, J., Brundell, E., Daneholt, B., and Hoog, C. (2000). The murine Scp3 gene is required for synaptonemal complex assembly, chromosome synapsis, and male fertility. Mol. Cell, 5, 73–83.

Zheng, Q., Simel, E. J., Klein, P. E., Royer, M. T. and Houtz, R. L. (1998) Expression, purification, and characterization of recombinant ribulose-1,5-bisphosphate carboxylase/oxygenase large subunit N-epsilon-methyltransferase. Protein Expr Purif, 14, 104–12.

What is claimed is:

1. A method for identifying a candidate compound that alters higher order dependent chromosome stability in mitosis and meiosis, said method comprising incubating a substrate for a methyltransferase, in the presence of a methyl donor, with a methyltransferase selected from human SUV39H2, murine Suv39h1, and murine Suv39h2 in the presence or absence of a test compound and determining whether the compound modulates the methyltransferase activity, wherein said modulation is indicative that said candidate compound alters higher order dependent chromosome stability in mitosis and meiosis.

2. The method of claim 1, wherein the methyltransferase methylates histone H3 at lysine 9.

3. The method of claim 2, wherein the methyltransferase is murine Suv39h1 or human SUV39H1.

4. The method of claim 2, wherein the methyltransferase murine Suv39h2.

5. The method of claim 1, wherein the substrate is histone H3 or an N-terminal fragment thereof that contains the methylation site at lysine 9.

6. The method of claim 5, wherein the histone H3 N-terminal fragment has the amino acid sequence as set forth in SEQ ID NO:7.

7. The method of claim 1, wherein the methyl donor is methionine or S-adenosyl-L-methionine.

8. The method of claim 1, wherein the methyl group of the methyl donor carries a detectable label.

9. The method of claim 8, wherein the methyl donor carries a chromogenic label and the methyltransferase activity is determined by measuring the change in colour upon transfer of the methyl group to the substrate.

10. The method of claim 8, wherein the methyl donor carries a radioactive label and the methyltransferase activity is determined by measuring the radioactivity transferred to the substrate upon transfer of the methyl group.

11. The method of claim 1, wherein the methyltransferase activity is determined immunologically by quantifying the binding of an antibody specific for the methylation site of the substrate.

12. The method of claim 11 wherein the substrate carries a detectable label.

* * * * *

SEQUENCE LISTING

<160> NUMBER OF SEQ ID NOS: 19

<210> SEQ ID NO 1
<211> LENGTH: 1452
<212> TYPE: DNA

-continued

```
<213> ORGANISM: Mus musculus
<220> FEATURE:
<221> NAME/KEY: 3'UTR
<222> LOCATION: (1)..(18)
<221> NAME/KEY: CDS
<222> LOCATION: (19)..(1452)

<400> SEQUENCE: 1
gaatgaaagc tccgcaag atg gcg acg gcc agg gcc aag gca cgg ggc agt        51
                    Met Ala Thr Ala Arg Ala Lys Ala Arg Gly Ser
                     1               5                  10 gag gca gga gcg cgg tgt cac cgg gct cca ggt ccg ccc cga ggg ccc        99
Glu Ala Gly Ala Arg Cys His Arg Ala Pro Gly Pro Pro Pro Arg Pro
             15                  20                  25 aag gcc agg cga acg gcg aga cgc cgc cgc gcg gag acc ctg acg gcg       147
Lys Ala Arg Arg Thr Ala Arg Arg Arg Ala Glu Thr Leu Thr Ala
         30                  35                  40 cga cgc tcg cgg ccg tct gcg ggc gag agg cgc gcc ggc tcc cag cga       195
Arg Arg Ser Arg Pro Ser Ala Gly Glu Arg Arg Ala Gly Ser Gln Arg
         45                  50                  55 gcg tgg tcc gga gct ccg cgg gcc gcg gtc ttt ggc gac gag tgt gca       243
Ala Trp Ser Gly Ala Pro Arg Ala Ala Val Phe Gly Asp Glu Cys Ala
 60              65                  70                  75 cga ggt gcc tta ttc aag gcc tgg tgt gtg cct tgc cta gtt tca ctt       291
Arg Gly Ala Leu Phe Lys Ala Trp Cys Val Pro Cys Leu Val Ser Leu
                 80                  85                  90 gat act ctc cag gaa tta tgt aga aaa gaa aag ctc aca tgt aaa tcg       339
Asp Thr Leu Gln Glu Leu Cys Arg Lys Glu Lys Leu Thr Cys Lys Ser
             95                 100                 105 att gga atc acc aaa agg aat cta aac aat tat gag gtg gag tac ttg       387
Ile Gly Ile Thr Lys Arg Asn Leu Asn Asn Tyr Glu Val Glu Tyr Leu
         110                 115                 120 tgt gac tac aag gta gca aag ggt gtg gaa tat tat ctt gta aaa tgg       435
Cys Asp Tyr Lys Val Ala Lys Gly Val Glu Tyr Tyr Leu Val Lys Trp
         125                 130                 135 aaa gga tgg cca gat tct aca aac acc tgg gag ccc ttg aga aac ctc       483
Lys Gly Trp Pro Asp Ser Thr Asn Thr Trp Glu Pro Leu Arg Asn Leu
140                 145                 150                 155 agg tgt cca cag ctc ctg cgg cag ttc tct gat gac aag aag act tac       531
Arg Cys Pro Gln Leu Leu Arg Gln Phe Ser Asp Asp Lys Lys Thr Tyr
                 160                 165                 170 tta gct cag gaa agg aaa tgc aag gct gtc aat tca aaa tcc ttg caa       579
Leu Ala Gln Glu Arg Lys Cys Lys Ala Val Asn Ser Lys Ser Leu Gln
             175                 180                 185 cct gca att gct gag tat att gta cag aaa gct aag caa aga ata gct       627
Pro Ala Ile Ala Glu Tyr Ile Val Gln Lys Ala Lys Gln Arg Ile Ala
         190                 195                 200 ctg cag aga tgg caa gat tac ctc aac aga aga aag aac cat aag ggg       675
Leu Gln Arg Trp Gln Asp Tyr Leu Asn Arg Arg Lys Asn His Lys Gly
         205                 210                 215 atg ata ttt gtt gaa aac act gtt gac ttg gag ggc cca cct tta gac       723
Met Ile Phe Val Glu Asn Thr Val Asp Leu Glu Gly Pro Pro Leu Asp
220                 225                 230                 235 ttc tac tac att aac gag tac agg cca gct ccc ggg atc agc ata aac       771
Phe Tyr Tyr Ile Asn Glu Tyr Arg Pro Ala Pro Gly Ile Ser Ile Asn
                 240                 245                 250 agt gaa gcc acc ttt gga tgt tca tgt aca gac tgc ttc ttt gac aag       819
Ser Glu Ala Thr Phe Gly Cys Ser Cys Thr Asp Cys Phe Phe Asp Lys
             255                 260                 265 tgt tgt cct gct gaa gct gga gtt gtg ttg gct tat aat aag aag caa       867
Cys Cys Pro Ala Glu Ala Gly Val Val Leu Ala Tyr Asn Lys Lys Gln
```

-continued

```
                 270                 275                 280
caa att aaa atc caa cca ggc act ccc atc tac gaa tgc aac tca agg      915
Gln Ile Lys Ile Gln Pro Gly Thr Pro Ile Tyr Glu Cys Asn Ser Arg
    285                 290                 295 tgt cga tgt gga cct gaa tgt ccc aat agg att gta caa aaa ggc aca      963
Cys Arg Cys Gly Pro Glu Cys Pro Asn Arg Ile Val Gln Lys Gly Thr
300                 305                 310                 315 caa tat tca ctg tgc atc ttt aaa act agc aat ggc tgt ggt tgg ggt     1011
Gln Tyr Ser Leu Cys Ile Phe Lys Thr Ser Asn Gly Cys Gly Trp Gly
                320                 325                 330 gta aaa acc ctt gtg aag att aaa aga atg agt ttt gtc atg gaa tat     1059
Val Lys Thr Leu Val Lys Ile Lys Arg Met Ser Phe Val Met Glu Tyr
335                 340                 345 gtt gga gag gtg atc aca agt gaa gag gcc gag aga cgg gga cag ttc     1107
Val Gly Glu Val Ile Thr Ser Glu Glu Ala Glu Arg Arg Gly Gln Phe
    350                 355                 360 tat gac aac aaa ggg atc acc tac ctc ttt gac ctg gac tac gag tct     1155
Tyr Asp Asn Lys Gly Ile Thr Tyr Leu Phe Asp Leu Asp Tyr Glu Ser
365                 370                 375 gat gag ttc aca gtg gat gca gct cga tat gga aac gta tcc cat ttt     1203
Asp Glu Phe Thr Val Asp Ala Ala Arg Tyr Gly Asn Val Ser His Phe
380                 385                 390                 395 gtg aat cat agt tgt gac cca aat ctt cag gtg ttt agt gtt ttc atc     1251
Val Asn His Ser Cys Asp Pro Asn Leu Gln Val Phe Ser Val Phe Ile
                400                 405                 410 gat aac ctt gat act cgg ctg ccc agg ata gca ttg ttc tct aca aga     1299
Asp Asn Leu Asp Thr Arg Leu Pro Arg Ile Ala Leu Phe Ser Thr Arg
            415                 420                 425 acc ata aac gct gga gaa gag ctg act ttt gac tat caa atg aaa ggt     1347
Thr Ile Asn Ala Gly Glu Glu Leu Thr Phe Asp Tyr Gln Met Lys Gly
        430                 435                 440 tct gga gaa gca tct tca gac tcc att gac cac agc cct gcc aaa aaa     1395
Ser Gly Glu Ala Ser Ser Asp Ser Ile Asp His Ser Pro Ala Lys Lys
    445                 450                 455 agg gtc aga acc caa tgt aaa tgt gga gcc gag act tgc aga ggt tac     1443
Arg Val Arg Thr Gln Cys Lys Cys Gly Ala Glu Thr Cys Arg Gly Tyr
460                 465                 470                 475 ctc aac tga                                                          1452
Leu Asn
```

<210> SEQ ID NO 2
<211> LENGTH: 477
<212> TYPE: PRT
<213> ORGANISM: Mus musculus

<400> SEQUENCE: 2

```
Met Ala Thr Ala Arg Ala Lys Ala Arg Gly Ser Glu Ala Gly Ala Arg
  1               5                  10                  15

Cys His Arg Ala Pro Gly Pro Pro Arg Pro Lys Ala Arg Arg Thr
                 20                  25                  30

Ala Arg Arg Arg Ala Glu Thr Leu Thr Ala Arg Arg Ser Arg Pro
             35                  40                  45

Ser Ala Gly Glu Arg Arg Ala Gly Ser Gln Arg Ala Trp Ser Gly Ala
         50                  55                  60

Pro Arg Ala Ala Val Phe Gly Asp Glu Cys Ala Arg Gly Ala Leu Phe
 65                  70                  75                  80

Lys Ala Trp Cys Val Pro Cys Leu Val Ser Leu Asp Thr Leu Gln Glu
                 85                  90                  95
```

```
Leu Cys Arg Lys Glu Lys Leu Thr Cys Lys Ser Ile Gly Ile Thr Lys
            100                 105                 110

Arg Asn Leu Asn Asn Tyr Glu Val Glu Tyr Leu Cys Asp Tyr Lys Val
        115                 120                 125

Ala Lys Gly Val Glu Tyr Tyr Leu Val Lys Trp Lys Gly Trp Pro Asp
    130                 135                 140

Ser Thr Asn Thr Trp Glu Pro Leu Arg Asn Leu Arg Cys Pro Gln Leu
145                 150                 155                 160

Leu Arg Gln Phe Ser Asp Asp Lys Lys Thr Tyr Leu Ala Gln Glu Arg
                165                 170                 175

Lys Cys Lys Ala Val Asn Ser Lys Ser Leu Gln Pro Ala Ile Ala Glu
            180                 185                 190

Tyr Ile Val Gln Lys Ala Lys Gln Arg Ile Ala Leu Gln Arg Trp Gln
        195                 200                 205

Asp Tyr Leu Asn Arg Arg Lys Asn His Lys Gly Met Ile Phe Val Glu
    210                 215                 220

Asn Thr Val Asp Leu Glu Gly Pro Pro Leu Asp Phe Tyr Tyr Ile Asn
225                 230                 235                 240

Glu Tyr Arg Pro Ala Pro Gly Ile Ser Ile Asn Ser Glu Ala Thr Phe
                245                 250                 255

Gly Cys Ser Cys Thr Asp Cys Phe Phe Asp Lys Cys Cys Pro Ala Glu
            260                 265                 270

Ala Gly Val Val Leu Ala Tyr Asn Lys Lys Gln Gln Ile Lys Ile Gln
        275                 280                 285

Pro Gly Thr Pro Ile Tyr Glu Cys Asn Ser Arg Cys Arg Cys Gly Pro
    290                 295                 300

Glu Cys Pro Asn Arg Ile Val Gln Lys Gly Thr Gln Tyr Ser Leu Cys
305                 310                 315                 320

Ile Phe Lys Thr Ser Asn Gly Cys Gly Trp Gly Val Lys Thr Leu Val
                325                 330                 335

Lys Ile Lys Arg Met Ser Phe Val Met Glu Tyr Val Gly Glu Val Ile
            340                 345                 350

Thr Ser Glu Glu Ala Glu Arg Arg Gly Gln Phe Tyr Asp Asn Lys Gly
        355                 360                 365

Ile Thr Tyr Leu Phe Asp Leu Asp Tyr Glu Ser Asp Glu Phe Thr Val
    370                 375                 380

Asp Ala Ala Arg Tyr Gly Asn Val Ser His Phe Val Asn His Ser Cys
385                 390                 395                 400

Asp Pro Asn Leu Gln Val Phe Ser Val Phe Ile Asp Asn Leu Asp Thr
                405                 410                 415

Arg Leu Pro Arg Ile Ala Leu Phe Ser Thr Arg Thr Ile Asn Ala Gly
            420                 425                 430

Glu Glu Leu Thr Phe Asp Tyr Gln Met Lys Gly Ser Gly Glu Ala Ser
        435                 440                 445

Ser Asp Ser Ile Asp His Ser Pro Ala Lys Lys Arg Val Arg Thr Gln
    450                 455                 460

Cys Lys Cys Gly Ala Glu Thr Cys Arg Gly Tyr Leu Asn
465                 470                 475
```

<210> SEQ ID NO 3
<211> LENGTH: 543
<212> TYPE: DNA
<213> ORGANISM: Homo sapiens
<220> FEATURE:
<221> NAME/KEY: misc_feature
<222> LOCATION: (1)..(543)
<223> OTHER INFORMATION: EST Acc. No.173625
<221> NAME/KEY: unsure
<222> LOCATION: (15)
<223> OTHER INFORMATION: May be any nucleic acid.
<221> NAME/KEY: unsure
<222> LOCATION: (23)
<223> OTHER INFORMATION: May be any nucleic acid.
<221> NAME/KEY: unsure
<222> LOCATION: (30)
<223> OTHER INFORMATION: May be any nucleic acid.
<221> NAME/KEY: unsure
<222> LOCATION: (31)..(32)
<223> OTHER INFORMATION: May be any nucleic acid.
<221> NAME/KEY: unsure
<222> LOCATION: (35)
<223> OTHER INFORMATION: May be any nucleic acid.
<221> NAME/KEY: unsure
<222> LOCATION: (39)..(40)
<223> OTHER INFORMATION: May be any nucleic acid.
<221> NAME/KEY: unsure
<222> LOCATION: (43)..(44)
<223> OTHER INFORMATION: May be any nucleic acid.
<221> NAME/KEY: unsure
<222> LOCATION: (49)..(50)
<223> OTHER INFORMATION: May be any nucleic acid.
<221> NAME/KEY: unsure
<222> LOCATION: (505)
<223> OTHER INFORMATION: May be any nucleic acid.

<400> SEQUENCE: 3

```
ggccatgtgg ttgancccct ggntttaccn nnccntggnn ggnnttgann cccctttagat      60
tatagtccag aatcattgtt gtcatataac tgccctcatc tttcagcttc gtcacttgtg     120
attacctttc caacttattc catgacaaaa cttattcttt taatcttcac atgggttttt     180
acaccccagc catggtcatt gatactgtga aagatgcaaa gtgaattact gtgtgccttt     240
ttgtacaatc ctattggtac agtgaggtcc acattgacag attgagatgc atttatagat     300
gggagtaaca ggtgggattt taatttgttg gtttttacta taagccaaaa gaattccagc     360
ttcaccaaga caacattttt catagaagca atctgtgcat gaacaacaaa aggtagcttc     420
atttactaag ctgattccag gagctggttt gtattcatca atatagcaga agtctgaagg     480
tgggccttct aagtgaaccc tattntcaac aaatatcact cctttattat tctgtcttct     540
gcg                                                                   543
```

<210> SEQ ID NO 4
<211> LENGTH: 579
<212> TYPE: DNA
<213> ORGANISM: Homo sapiens
<220> FEATURE:
<221> NAME/KEY: misc_feature
<222> LOCATION: (1)..(579)
<223> OTHER INFORMATION: EST Acc. No. AQ494637
<221> NAME/KEY: unsure
<222> LOCATION: (25)
<223> OTHER INFORMATION: May be any nucleic acid.
<221> NAME/KEY: unsure
<222> LOCATION: (32)..(33)
<223> OTHER INFORMATION: May be any nucleic acid.
<221> NAME/KEY: unsure
<222> LOCATION: (36)
<223> OTHER INFORMATION: May be any nucleic acid.
<221> NAME/KEY: unsure
<222> LOCATION: (38)
<223> OTHER INFORMATION: May be any nucleic acid.
<221> NAME/KEY: unsure
<222> LOCATION: (39)
<223> OTHER INFORMATION: May be any nucleic acid.
<221> NAME/KEY: unsure
<222> LOCATION: (45)
<223> OTHER INFORMATION: May be any nucleic acid.

<221> NAME/KEY: unsure
<222> LOCATION: (51)
<223> OTHER INFORMATION: May be any nucleic acid.
<221> NAME/KEY: unsure
<222> LOCATION: (58)
<223> OTHER INFORMATION: May be any nucleic acid.
<221> NAME/KEY: unsure
<222> LOCATION: (66)
<223> OTHER INFORMATION: May be any nucleic acid.
<221> NAME/KEY: unsure
<222> LOCATION: (71)
<223> OTHER INFORMATION: May be any nucleic acid.
<221> NAME/KEY: unsure
<222> LOCATION: (73)
<223> OTHER INFORMATION: May be any nucleic acid.
<221> NAME/KEY: unsure
<222> LOCATION: (75)
<223> OTHER INFORMATION: May be any nucleic acid.
<221> NAME/KEY: unsure
<222> LOCATION: (126)
<223> OTHER INFORMATION: May be any nucleic acid.
<221> NAME/KEY: unsure
<222> LOCATION: (168)
<223> OTHER INFORMATION: May be any nucleic acid.
<221> NAME/KEY: unsure
<222> LOCATION: (170)
<223> OTHER INFORMATION: May be any nucleic acid.
<221> NAME/KEY: unsure
<222> LOCATION: (502)
<223> OTHER INFORMATION: May be any nucleic acid.
<221> NAME/KEY: unsure
<222> LOCATION: (524)
<223> OTHER INFORMATION: May be any nucleic acid.

<400> SEQUENCE: 4

```
gcttctcata catgatacgt gttcngctct gnngtntnng tttangaata cntaaaanaa      60
aaggnagggg ngncntttga ttcgtgtgat tccatagatg cactcatatg gaactgtatt     120
tcattntgtg aatcatagta gtgacccaaa tcttcatatg ttctatgntn tcactgataa     180
cttgacactg gccttcccta tatagctctg tgttccatga gaactataaa tgctggagaa     240
gagttgattt tgacaatca acaaaaagt tctggggata tatcttcaga gtttattgac       300
cacagctcag ccaaaaagag ggtcagaact gtatgtaaat gtggagctgt gacttgcaga     360
ggttgcctca aatgaatttt caggaaatag aaatgatgat aattggtagt tgtttctttt     420
ttctaatgtt atcattctaa aaataagtat ttggaactct cttttcatat tatcaagatt     480
attactatgt taaattgaca tncatggttc aaggcattta ccanatgcat tactgatgcc     540
tcttgagaga gggccactgt gttgcataga ctgatctga                            579
```

<210> SEQ ID NO 5
<211> LENGTH: 565
<212> TYPE: DNA
<213> ORGANISM: Homo sapiens
<220> FEATURE:
<221> NAME/KEY: misc_feature
<222> LOCATION: (1)..(565)
<223> OTHER INFORMATION: EST Acc. No. AQ691972
<221> NAME/KEY: unsure
<222> LOCATION: (19)
<223> OTHER INFORMATION: May be any nucleic acid.
<221> NAME/KEY: unsure
<222> LOCATION: (38)
<223> OTHER INFORMATION: May be any nucleic acid.
<221> NAME/KEY: unsure
<222> LOCATION: (42)
<223> OTHER INFORMATION: May be any nucleic acid.
<221> NAME/KEY: unsure
<222> LOCATION: (353)
<223> OTHER INFORMATION: May be any nucleic acid.
<221> NAME/KEY: unsure
<222> LOCATION: (397)

<223> OTHER INFORMATION: May be any nucleic acid.

<400> SEQUENCE: 5

```
agaggatgag catggatcnt cgctatagca aaccacanat anaatcccac ctgttactcc      60
catctataaa tgcatctcaa tctgtcaatg tggaccttac tgtaccaata ggattgtaca     120
aaaaggcaca cagtaattca ctttgcatct ttcacagtat caatgaccat ggctggggtg    180
taaaaaccca tgtgaagatt aaaagaataa gttttgtcat ggaataagtt ggaaaggtaa    240
tcacaagtga cgaagctgaa agatgagggc agttatatga caacaaatga tctggactat    300
gaatctgatg aattcacaga ggatgcagct caatatggaa ctgtatttca ttntgtgaat    360
cataagtagt gacccaaact tcatatgttc aatgttntca ttgataactt gacactggcc    420
tttccttaat agctctgtgt tccatgagaa ctataaatgc tggagaagaa gtgattttg    480
acatcaacaa aagttctggg attatcttca aagttattgc cacagttacc aaaagaaggc    540
aaactgttgt aatgtgagct gtact                                          565
```

<210> SEQ ID NO 6
<211> LENGTH: 535
<212> TYPE: DNA
<213> ORGANISM: Homo sapiens
<220> FEATURE:
<221> NAME/KEY: misc_feature
<222> LOCATION: (1)..(535)
<223> OTHER INFORMATION: EST Acc. No. AQ554070

<400> SEQUENCE: 6

```
tcagactcat agtccagatc aaagagattc tgtgattccc ttgttgtcat agaactgtcc      60
tcgtctttca gcttcttcac ttgtgattac ctaaacagaa aaaactgtaa gtatattacg    120
tagctactga accaaagaag cattcatcta cctatctact aatatgcgaa tacctacaaa    180
tatttaaaaa gtaagaaatt caggtgtcat caaagcaaac attcacacaa actaagactc    240
agatgcaaag aggtgggaaa atgagggaa gaaaatgat aatgcaaaag actgatgacc      300
tttttttttt aaacagggtc tcactctgtc actcaggcta gaatgcggtg gtgccatcat    360
gactccctgt atcctttaac tcctgggatc aagcgatctt cctgcctcag cctcctgact    420
agctggatca caggtgcata ccgccatgcc cagctaatga tttagttttt atagagatgt    480
ggggtctcac tatgttgccc acactggtct ggaactcctg ggctcaagtg agcct         535
```

<210> SEQ ID NO 7
<211> LENGTH: 20
<212> TYPE: PRT
<213> ORGANISM: Homo sapiens

<400> SEQUENCE: 7

Ala Arg Thr Lys Gln Thr Ala Arg Lys Ser Thr Gly Gly Lys Ala Pro
1               5                  10                  15

Arg Lys Gln Leu
            20

<210> SEQ ID NO 8
<211> LENGTH: 20
<212> TYPE: PRT
<213> ORGANISM: Homo sapiens

<400> SEQUENCE: 8

Met Gly Pro Arg Arg Arg Ser Arg Lys Pro Glu Ala Pro Arg Arg Arg
1               5                  10                  15

```
Arg Ser Pro Ser Pro
            20

<210> SEQ ID NO 9
<211> LENGTH: 22
<212> TYPE: PRT
<213> ORGANISM: Rattus rattus

<400> SEQUENCE: 9

Met Glu Thr Ser Ser Arg Gly Gly Lys Lys Ser Thr Lys Thr
 1               5                  10                  15

Ser Arg Ser Ala Lys Ala Gly
            20      22

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
atgggggcag ggttttcggg tagac                                        25

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 11
aaatggtatt tgcaggccac ttcttg                                       26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 12
aaatggtatt tgcaggccac ttcttg                                       26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13
ggatgggatg gtggaatggt ttttat                                       26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
aaatggtatt tgcaggccac ttcttg                                       26

<210> SEQ ID NO 15
```

-continued

```
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 15
aaatggtatt tgcaggccac ttcttg                                          26

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 16
gactgcctag tctggcactg aact                                            24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
gatcactgcg tacatataca ctgat                                           25

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 18
tagacttcta ctacattaac g                                               21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
gatgtcagtg gctatgaatg                                                 20
```